US007375082B2

(12) United States Patent
Mickle et al.

(10) Patent No.: US 7,375,082 B2
(45) Date of Patent: May 20, 2008

(54) ABUSE-RESISTANT HYDROCODONE COMPOUNDS

(75) Inventors: Travis Mickle, Charlottesville, VA (US); Suma Krishnan, Blacksburg, VA (US); James Scott Moncrief, Christiansburg, VA (US); Christal Mickle, Charlottesville, VA (US); Christopher Lauderback, Blacksburg, VA (US); Thomas Piccariello, Blacksburg, VA (US)

(73) Assignee: Shire LLC, Florence, KY (US)

( * ) Notice: Subject to any disclaimer, the term of this patent is extended or adjusted under 35 U.S.C. 154(b) by 301 days.

(21) Appl. No.: 10/953,116

(22) Filed: Sep. 30, 2004

(65) Prior Publication Data

US 2005/0176645 A1    Aug. 11, 2005

Related U.S. Application Data

(63) Continuation-in-part of application No. 10/923,257, filed on Aug. 23, 2004, which is a continuation-in-part of application No. PCT/US03/05525, filed on Feb. 24, 2003, which is a continuation-in-part of application No. 10/156,527, filed on May 29, 2002, now Pat. No. 7,060,708.

(60) Provisional application No. 60/568,011, filed on May 5, 2004, provisional application No. 60/567,800, filed on May 5, 2004, provisional application No. 60/507,012, filed on Sep. 30, 2003, provisional application No. 60/366,258, filed on Mar. 22, 2002, provisional application No. 60/362,082, filed on Mar. 7, 2002, provisional application No. 60/358,368, filed on Feb. 22, 2002.

(51) Int. Cl.
*A61K 38/00* (2006.01)
*A61K 38/04* (2006.01)
*A61K 38/06* (2006.01)
*A61K 31/00* (2006.01)

(52) U.S. Cl. .......................... 514/12; 514/14; 514/17; 530/330; 530/331; 424/78.13

(58) Field of Classification Search .................. 514/9
See application file for complete search history.

(56) References Cited

U.S. PATENT DOCUMENTS

| | | | |
|---|---|---|---|
| 3,843,696 A | 10/1974 | Wagner et al. |
| 3,846,399 A | 11/1974 | Hirschmann et al. |
| 3,878,187 A | 4/1975 | Schneider et al. |
| 3,884,898 A | 5/1975 | Schneider |
| 3,975,342 A | 8/1976 | Gross |
| 3,998,799 A | 12/1976 | Bodor et al. |
| 4,025,501 A | 5/1977 | Leute |
| 4,040,907 A | 8/1977 | Ullman et al. |
| 4,346,166 A | 8/1982 | Montag et al. |
| 4,356,166 A | 10/1982 | Peterson et al. |
| 4,399,121 A | 8/1983 | Albarella et al. |
| 4,427,660 A | 1/1984 | Schiffman et al. |
| 4,457,907 A | 7/1984 | Porter |
| 4,552,864 A | 11/1985 | Antoni et al. |
| 4,650,675 A | 3/1987 | Borel et al. |
| 4,801,575 A | 1/1989 | Pardridge |
| 4,863,735 A | 9/1989 | Kohn et al. |
| 4,902,505 A | 2/1990 | Pardridge et al. |
| 4,960,790 A | 10/1990 | Stella et al. |
| 4,976,962 A | 12/1990 | Bichon et al. |
| 5,026,827 A | 6/1991 | Miyazaki |
| 5,073,641 A | 12/1991 | Bundgaard et al. |
| 5,087,616 A | 2/1992 | Myers et al. |
| 5,169,933 A | 12/1992 | Anderson et al. |
| 5,183,883 A | 2/1993 | Tanaka et al. |
| 5,219,564 A | 6/1993 | Zalipsky et al. |
| 5,238,714 A | 8/1993 | Wallace et al. |
| 5,362,831 A | 11/1994 | Mongelli et al. |
| 5,534,496 A | 7/1996 | Lee et al. |
| 5,670,477 A | 9/1997 | Poduslo et al. |
| 5,762,909 A | 6/1998 | Uzgiris |
| 5,767,227 A | 6/1998 | Latham et al. |
| 5,846,743 A | 12/1998 | Janmey et al. |
| 5,851,536 A | 12/1998 | Yager et al. |
| 5,882,645 A | 3/1999 | Toth et al. |
| 5,891,459 A | 4/1999 | Cooke et al. |

(Continued)

FOREIGN PATENT DOCUMENTS

EP    0 187 547 A2    7/1987

(Continued)

OTHER PUBLICATIONS

Aggarwal, et al., "Synthesis and Biological Evaluation of Prodrugs of Zidovudine," *J. Med. Chem.*, 33(5):1505-1511 (1990).

(Continued)

*Primary Examiner*—Cecilia J. Tsang
*Assistant Examiner*—Maury Audet
(74) *Attorney, Agent, or Firm*—Darby & Darby P.C.

(57) ABSTRACT

The present invention decreases the potential for abuse of opioids, particularly hydrocodone, by covalent modification. The invention provides methods of delivering hydrocodone as conjugates that release the hydrocodone following oral administration while being resistant to abuse by circuitous routes such as intravenous ("shooting") injection and intranasal administration ("snorting"). Further, hydrocodone compositions of the invention are resistant to oral abuse as well, since release of the hydrocodone at suprapharmacological doses reaches saturation.

9 Claims, 99 Drawing Sheets

U.S. PATENT DOCUMENTS

| | | | |
|---|---|---|---|
| 5,898,033 | A | 4/1999 | Swadesh et al. |
| 5,910,569 | A | 6/1999 | Latham et al. |
| 5,948,750 | A | 9/1999 | Garsky et al. |
| 5,952,294 | A | 9/1999 | Lazo et al. |
| 5,977,163 | A | 11/1999 | Li et al. |
| 6,005,004 | A | 12/1999 | Katz et al. |
| 6,030,941 | A | 2/2000 | Summerton et al. |
| 6,043,230 | A | 3/2000 | Arimilli et al. |
| 6,048,736 | A | 4/2000 | Kosak |
| 6,074,659 | A | 6/2000 | Kunz et al. |
| 6,075,120 | A | 6/2000 | Cheronis et al. |
| 6,093,391 | A | 7/2000 | Kabanov et al. |
| 6,235,718 | B1 | 5/2001 | Balasubramanium et al. |
| 6,255,285 | B1 | 7/2001 | Kotake |
| 6,306,993 | B1 | 10/2001 | Rothbard et al. |
| 6,309,633 | B1 | 10/2001 | Ekwuribe et al. |
| 6,458,842 | B1 | 10/2002 | Dickinson et al. |
| 6,716,452 | B1 | 4/2004 | Piccariello et al. |
| 6,740,641 | B2 | 5/2004 | Gao |
| 6,784,186 | B1 | 8/2004 | Jackson |
| 7,060,708 | B2 | 6/2006 | Piccariello et al. |
| 2001/0031873 | A1 | 10/2001 | Greenwald et al. |
| 2002/0059013 | A1 | 5/2002 | Rajala et al. |
| 2002/0098999 | A1 | 7/2002 | Gallop et al. |
| 2002/0099013 | A1 | 7/2002 | Piccariello et al. |
| 2002/0151526 | A1 | 10/2002 | Gallop et al. |
| 2002/0151529 | A1 | 10/2002 | Cundy et al. |
| 2004/0204434 | A1 | 10/2004 | Shaler |
| 2005/0038121 | A1 | 2/2005 | Mickle et al. |
| 2005/0054561 | A1 | 3/2005 | Mickle et al. |
| 2005/0065086 | A1 | 3/2005 | Mickle et al. |
| 2005/0069550 | A1 | 3/2005 | Mickle et al. |
| 2005/0080012 | A1 | 4/2005 | Mickle et al. |
| 2005/0176644 | A1* | 8/2005 | Mickle et al. ............. 514/15 |
| 2005/0176645 | A1 | 8/2005 | Mickle et al. |
| 2005/0176646 | A1 | 8/2005 | Mickle et al. |
| 2005/0266070 | A1* | 12/2005 | Mickle et al. ............ 424/451 |
| 2006/0014697 | A1 | 1/2006 | Mickle et al. |

FOREIGN PATENT DOCUMENTS

| | | |
|---|---|---|
| WO | WO 94/11021 A | 5/1994 |
| WO | WO 95/12605 | 5/1995 |
| WO | WO 95/14033 | 5/1995 |
| WO | WO 97/36616 | 10/1997 |
| WO | WO 08/04277 | 2/1998 |
| WO | WO 98/04277 | 2/1998 |
| WO | WO 00/37103 A | 6/2000 |
| WO | WO 02/34237 A1 | 5/2002 |

OTHER PUBLICATIONS

Amidon, G. et al., "A Theoretical Basis for a Biopharmaceutic Drug Classification: The Correlation of in Vitro Drug Product Dissolution and in Vivo Bioavailability," *Pharmaceutical Research*, vol. 12, No. 3, (1995).
Amidon, G.L., et al., "5'-Amino Acid Esters of Antiviral Nucleosides, Acyclovir, and AZT are Absorbed by the Intestinal PEPT1 Peptide Transporter," *Pharm Res*, 15(2):175 (1999), Abstract.
Balimane, P., et al., "Effect of Ionization on the Variable Uptake of Valacyclovir via the Human Intestinal Peptide Transporter (hPepT1) in CHP cells," *Biopharm Drug Dispos*, 21(5):165-174 (2000), Abstract.
Balimane, P.V., et al., "Direct Evidence for Peptide Transporter (PepT1)-Mediated Uptake of a Nonpeptide Prodrug, Valacyclovir,"*Biochem Biophys Res Commun*, 250(2):246-251 (1998), Abstract.
Bunevicius, R., "Effects of Thyroxine as Compared with Thyroxine Plus Triiodothyronine in Patients with Hypothyroidism," *The New England Journal of Medicine*, vol. 340, No. 6 (1999).
Burnette, Thimysta C., et al., "Metabolic Disposition of the Acyclovir Prodrug Valaciclovir in the Rat," *Drug Metabolism and Disposition*, 22(1):60-64 (1994).
Canaris, G., "The Colorado Thyroid Disease Prevalence Study," Archives Internal Medicine Articles and Abstracts, vol. 160, No. 4 (2000).
De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).
Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.
Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448-454 (1999), Abstract.
Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998), Abstract.
Han, H.K., et al., "Cellular Uptake Mechanism of Amino Acid Ester prodrugs in Caco-2hPEPT1 Cells Overexpressing a Human Peptide Transporter," *Pharm Res.* 15(9):1382-1386 (1998), Abstract.
Han, Hyo-Kyung, et al., "Targeted Prodrug Design to Optimixe Drug Delivery," *AAPS PharmaSci*, 2(1): Article 6 (2000).
Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).
Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1):E9 (2001), Abstract.
Hosztafi, S. et al. "Synthesis and Analgetic Activity of Nicotinic Esters of Morphine Derivatives," Arzneim.-Forsch./Drug Res. 43(II), Nr. 11 (1993).
International Search Report, Dated Oct. 9, 2003, for PCT/US03/05525.
International Search Report, dated Sep. 3, 2003.
Knutter, I, et al., "A Novel Inhibitor of the Mammalian Peptide Transporter PEPT1," *Biochemistry*, 40(14):4454-4458 (2001), Abstract.
Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid,".
Kramer, Werner et al., "Intestinal Absorption of Peptides by Coupling to Bile Acids," *The Journal of Biochemistry*, 269(14):10621-10627 (1994).
Leibach, F.H, et al., "Peptide Transporters in the Intestine and the Kidney," *Annu Rev. Nutri*, 16:99-119 (1996), Abstract.
Li, Chun, et al., "Complete Regression of Well-Established Tumors Using a Novel Water-Soluble Poly(L-Glutamic Acid)-Paclitaxel Conjugate," *Caner Res*, 58:2404-2409 (1998).
Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).
Negishi, Naoki , et al., "Coupling of Naltrexone to Biodegradable Poly (α-Amino Acids)," *Pharmaceutical Research*, 4(4):305-310 (1987).
Nishida, Koyo, et al., "Pharmacokinetic Analysis of in Vivo Metabolism of Amino Acid or Dipeptide Conjugates of Salicylic Acid in Rabbit Intestinal Microorganisms," *Pharmaceutical Research*, 11(1):160-164 (1994).
Oh, D., et al., "Estimating the Fraction Dose Absorbed from Suspensions of Poorly Soluble Compounds in Humans: A Mathematical Model," *Pharmaceutical Research*, vol. 10, No. 2 (1993).
Oh, DM, et al., "Drug Transport and Targeting. Intestinal Transport," *Pharma Biotechnol*, 12:59-88 (1999), Abstract.
Okada, Masahiko, et al., "Synthesis of Glycopeptide-conjugates via Ring-Opening Polymerization of Sugar-Substituted α-Amino Acid N-Carboxyanhydrides (GlycoNCAs)," *Proc. Japan Acad.*, 73:205-209 (1997).

Orten, James M. et al., "Thyroxine," *Human Biochemistry*, 9th Ed., C.V. Mosby Company, St. Louis,pp. 401-405 (1975).

Pade, V., et al., "Link Between Drug Absorption Solubility and Permeability Measurements in Caco-2 Cells," *Journal of Pharmaceutical Sciences*, vol. 87, No. 12 (1998).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA*, 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Shen, H., et al., "Developmental Expression of PEPT1 and PEPT2 in Rat Small Intestine, Colon, and Kidney," *Pediatr Res*, 49(6):789-795 (2001), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Toft, A., "Thyroid Hormone Replacement—One Hormone or Two?," *The New England Journal of Medicine*, vol. 340, No. 6 (1999).

Toth, Istvan, "A Novel Chemical Approach to Drug Delivery: Lipidic Amino Acid Conjugates," *Journal of Drug Targeting*, 2:217-239 (1994).

Zunino, Franco, et al., "Anti-Tumor Activity of Daunorubicin Linked to Poly-L-Aspartic Acid," *International Journal of Cancer*, 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

Supplementary European Search Report for EP 01273387 dated Sep. 28, 2004.

U.S. Appl. No. 10/923,088, Entitled "Active Delivery Systems And Methods For Protecting And Administering Active Agents", Mickle et al., filed Aug. 23, 2004.

U.S. Appl. No. 10/953,111, Entitled "Compounds and Compositions for the Prevention of Overdose of Oxycodone", Mickle et al., filed Aug. 23, 2004.

U.S. Appl. No. 11/179,801, Entitled "Carbohydrate Conjugates to Prevent Abuse of Controlled Substances", Mickle et al., filed Jul. 13, 2005.

U.S. Appl. No. 11/392,878, Entitled "Pharmaceutical Compositions for Prevention of Overdose or Abuse", Mickle et al., filed Apr. 4, 2006.

U.S. Appl. No. 11/400,304, Entitled "Abuse Resistant Amphetamine Prodrugs", Mickle et al., filed Apr. 10, 2006.

Hughes, et al. Lipidic Peptides. III: Lipidic Amino Acid and Oligomer Conjugates of Morphine, Journal of Pharmaceutical Sciences, vol. 80, No. 12, Dec. 1991.

\* cited by examiner

Representative Nucleosides

Protected Thymidine

Site of Conjugation for Hydrocodone

US 7,375,082 B2

ABUSE-RESISTANT HYDROCODONE COMPOUNDS

CROSS REFERENCE RELATED APPLICATIONS

This application claims benefit under 35 U.S.C. 119(e) to U.S. Provisional application No. 60/567,800 filed May 5, 2004; U.S. Provisional application No. 60/507,012 filed Sep. 30, 2003; and U.S. Provisional application No. 60/568,011 filed on May 5, 2004. This application is also a continuation-in-part and claims benefit under 35 U.S.C. 120 to U.S. application Ser. No. 10/156,527 filed May 29, 2002 which claims the benefit under 35 U.S.C. 119(e) to U.S. Provisional application No. 60/366,258 filed Mar. 22, 2002. This application is also a continuation-in-part and claims benefit under 35 U.S.C. 120 to U.S. application Ser. No. 10/923,257 filed Aug. 23, 2004 which is a continuation-in-part and claims benefit under 35 U.S.C. 120 to PCT/US03/05525 filed Feb. 24, 2003 which claims benefit under 35 U.S.C. 119(e) to U.S. Provisional application 60/358,368 filed Feb. 22, 2002 and U.S. Provisional application 60/362,082 filed Mar. 7, 2002. Each of the above applications is hereby incorporated by reference in their entirety.

FIELD OF INVENTION

Opioids are highly effective as analgesics and are commonly prescribed for the treatment of acute and chronic pain. They are also commonly used as antitussives. The opioids, however, also produce euphoria and are highly addictive. As a result they are often abused with far reaching social and health related consequences. The present invention decreases the potential for abuse of opioids, particularly hydrocodone, by covalent modification. The invention provides methods of delivering hydrocodone as conjugates that release the hydrocodone following oral administration while being resistant to abuse by circuitous routes such as intravenous ("shooting") injection and intranasal administration ("snorting"). Further, hydrocodone compositions of the invention are resistant to oral abuse as well, since release of the hydrocodone at suprapharmacological doses reaches saturation. The invention also decreases the chances of dose escalation that often leads to accidental addiction.

BACKGROUND

The word opium is derived from the Greek name for juice as the drug is contained in the juice of the poppy, *Papaver somniferum*. Archeological digs in Switzerland uncovered opium poppy seeds and pods dating to the Neolithic age (8,000 B.C.-5,500 B.C.), suggesting opium was used before recorded history. The art of poppy-culling was established by the ancient Sumarians in Mesopotamia around 3500 B.C. They referred to it as hul gil, the "joy plant". The use of the plant and its euphoric effect was passed on to its trading partners and made its way westward to Egypt and eventually to Greece and Europe. The medicinal use of opium traces back centuries and its description was first recorded by Theophrastus in the third century B.C. Hippocrates, the father of medicine, mentioned opium's usefulness in curing a number of diseases and found it particularly effective for diarrhea. Opium has been used as a cure all to relieve pain and suffering in cultures around the world throughout history.

Around 1500 Portuguese sailors began mixing opium with tobacco and smoking it. The effects of smoking opium produced an instantaneous euphoria. The practice spread to China and lead to an increased demand for opium which greatly influenced both economics and politics worldwide. In 1803 Frederich Sertuerner discovered the principle active ingredient in opium: morphine, named after the Greek god of dreams. In 1827 E. Merck & Company of Darmstadt, Germany began commercial manufacturing of morphine. The medicinal and recreational use of morphine was prevalent through the rest of the $19^{th}$ century. Dr. Alexander Wood of Edingburg discovered a new method of administering morphine by injection with a syringe in 1843 and found the effects were instantaneous and that morphine was three times more potent by this route.

In 1890 the U.S. Congress imposed a tax on opium and morphine in its first act to address the growing problem of addiction. Heinrich Dreser, in 1895, produced acetylated morphine for The Bayer Company of Eberfield, Germany. Acetylated morphine was named heroin and marketed commercially three years later. Heroin was purported not to have some of the common side effects as morphine and at one point was supplied as free samples in the mail by the philanthropic Saint James Society to morphine addicts who wished to break their habits. By the early 1900s heroin addiction had risen to alarming rates. In 1906 congress passed the pure food and drug act requiring contents labeling of patented medicines. As a result the availability of opiates and opiate consumers significantly declined. In 1914, the Harrison Narcotics Act required doctors, pharmacists and others who prescribe narcotics to register and pay a tax. Congress banned the sale of narcotics altogether in 1923. In the wake of the federal ban on opium trade was driven under ground. Illicit use of heroin continued with varying degrees throughout the century, and remains an enormous social problem today.

The scourge of morphine and heroin abuse lead to the search for potent analgesics that would lack the potential for addiction. In the 1940's two synthetic compounds, meperidine and methadone, were produced and found to have morphine-like actions, unfortunately, including induction of tolerance and addiction. The term opioid was coined to refer to natural and synthetic drugs that are, to varying degrees, opium or morphine like in their properties. Opioids interact with several closely related receptors and share biological properties with three families of endogenous neuropeptides, endorphins, enkaphalins, and dynorphins. A number of additional opioids were produced with varying degrees of morphine-like activity. In general, the analgesic potency of synthetic morphine agonists produces corresponding levels of tolerance and addiction. Thus attempts to find an effective morphine-like analgesic that is free of the potential for addiction have fallen short to date.

Despite their addictive properties and the potential for abuse, morphine-like drugs, particularly, codeine, hydrocodone, and oxycodone have been routinely prescribed as treatment for severe acute and chronic pain in recent decades. This is, in part, because there are no alternatives to relieve severe pain that is resistant to other less potent analgesics such as non-steroidal anti-inflammatory drugs (NSAIDS). In this regard, others have attempted to decrease the abuse potential through formulations and the inclusion of morphine antagonists such as naltrexone. These approaches, unfortunately, can be circumvented and have not solved the problem.

In 1995, Purdue Frederich introduced a high oral dose oxycodone product in a time-release formula. Initially the product was marketed in doses as high as 160 mg. Subsequently, when a problem arose with people crushing the tablets to obtain the entire dose immediately, and in some cases snorting or shooting the ingredients, the high dose (160 mg) tablet was removed from the market. The 80 mg extended release oxycodone product (Oxycontin™) is still commercially available. Abuse of Oxycontin resulted in the FDA issuing a change to the Oxycontin approved label in 2001 which included the following warning:

OXYCONTIN TABLETS ARE TO BE SWALLOWED WHOLE AND ARE NOT TO BE BROKEN, CHEWED OR CRUSHED. TAKING BROKEN, CHEWED, OR CRUSHED OXYCONTIN TABLETS LEADS TO RAPID RELEASE AND ABSORPTION OF A POTENTIALLY FATAL DOSE OF OXYCODONE.

In recent years the misuse of opioid painkillers has nearly quadrupled. An estimated 2.4 million people in the U.S. began misusing prescription pain killers in 2001 as compared to 628,000 in 1990 according to the federal government's Survey on Drug Use and Health. An estimated 4.4 million patients take more pain medication than their prescribed amount. The rate of full blown addiction is 0.3 percent, however, any patient that does not follow their prescription is considered at risk. Pain medications prescribed for acute pain typically contain about 5 to 10 mg of hydrocodone, oxycodone, or codiene.

Hydrocodone is an opioid analgesic and antitussive and occurs as fine, white crystals or as crystalline powder. Hydrocodone is a semisynthetic narcotic analgesic prepared from codeine with multiple actions qualitatively similar to those of codeine. It is mainly used as an antitussive in cough syrups and tablets in sub-analgesic doses (2.5-5 mg). Additionally, it is used for the relief of moderate to moderately severe pain.

Patients taking opioid analgesics such as hydrocodone for pain relief can become accidentally addicted. As tolerance to the opioids develops more drug is needed to stop the pain and generate the sense of well being initially achieved with the prescribed dose. This leads to dose escalation, which if left unchecked can lead rapidly to addiction. In some cases patients have become full blown addicts in as little as thirty days.

As a result of their addictive properties and potential for abuse, opioids are scheduled controlled substances and are available only by prescription. It has been suggested that this precipitates under-utilization of opioids for pain relief. Although it is well known that opioids are the most effective treatment for severe pain, their abuse liability and the potential for fatal overdose provide a legitimate concern for any physician considering their use in pain management. According to Martino, over 125 journal and periodical articles and eighteen books have been written on the subject. There is a general consensus that inadequate treatment of chronic pain is the rule in the United states and most developed nations. It has been estimated that 75 percent of the 23 million people who have surgery each year, 60 percent of the 50 million persons living with chronic pain, and 70 percent of persons with cancer pain do not receive adequate pain management. In this regard, thirty-three states have enacted laws (intractable pain treatment acts (IPTAs)) designed to provide physicians with some measure of regulatory relief by reducing the real and perceived risks of being subjected to sanctions for treating pain with opioids.

There appears to be a direct correlation of diversion of prescribed opioids with the number of prescriptions per capita. As prescription numbers rise, the number of emergency room visits and deaths from overdose increase correspondingly. For example, the number of prescriptions for hydrocodone products rose from 56 million in 1998 to 89 million in 2000.

DETAILED DESCRIPTION OF THE INVENTION

Figure 1:
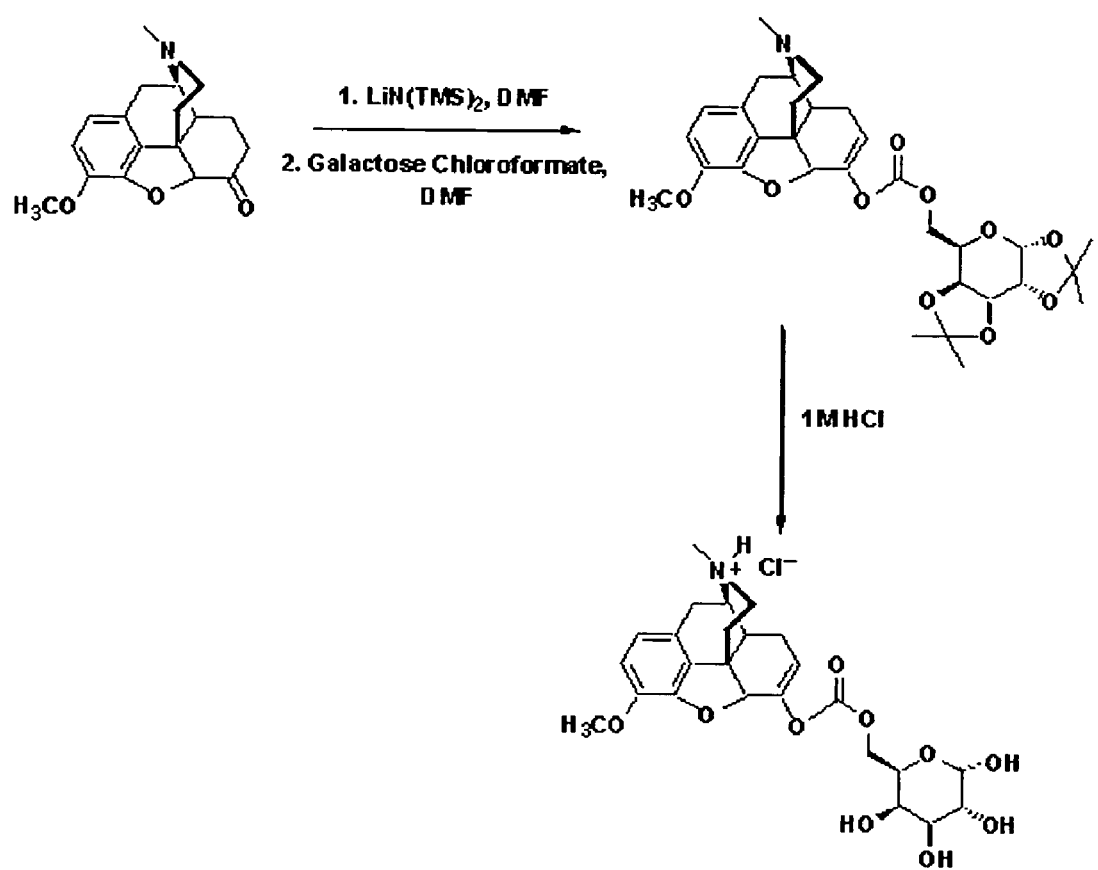
FIG. 1. illustrates preparation of Galacto-Hydrocodone.

The present invention relates to changing the pharmacokinetic and pharmacological properties of opioids, particularly hydrocodone and its derivatives, through covalent modification. Covalent attachment of a chemical moiety to an opioid can change the rate and extent of absorption, metabolism, distribution, and elimination of the drug. When administered at a normal therapeutic dose the bioavailability (the time-versus-concentration curve; area under the curve; AUC) of the opioid is similar to that of the parent opioid compound. As the oral dose is increased, however, the bioavailability of the covalently modified opioid relative to the parent opioid begins to decline. At a suprapharmacological doses the bioavailability of the opioid conjugate is substantially decreased as compared to the parent opioid. The relative decrease in bioavailability at higher doses abates the euphoria obtained when doses of the opioid conjugate are taken above those of the intended prescription. This in turn diminishes the abuse potential, whether unintended or intentionally sought.

Persons that abuse opioids such as hydrocodone commonly seek to increase their euphoria by snorting or injecting the drugs. These routes of administration increase the rate and extent of drug absorption and provide a faster, nearly instantaneous, effect. This increases the amount of drug that reaches the central nervous system where it has its effect. In a particular embodiment of the invention the bioavailability of the covalently modified opioid is substantially decreased by the intranasal and intravenous routes as compared to the parent opioid compound. Thus the illicit practice of snorting and shooting the drug loses its advantage.

In accordance with the present invention and as used herein, the following terms, are defined with the following meanings, unless explicitly stated otherwise. For additional methods of attaching opioids to carriers, see application number U.S. Ser. No. 10/156,527, and/or PCT/US03/05524 and/or PCT/US03/05525 each of which is hereby incorporated by reference in its entirety.

The invention utilizes covalent modification of the opioid hydrocodone to decrease its potential for causing overdose or abuse. The hydrocodone is covalently modified in a manner that decreases its pharmacological activity, as compared to the unmodified hydrocodone, at doses above those considered therapeutic. When given at lower doses, such as those intended for therapy, the covalently modified hydrocodone retains pharmacological activity similar to that of the unmodified hydrocodone. The covalent modification of hydrocodone may comprise the attachment of any chemical moiety through conventional chemistry.

Compounds, compositions and methods of the invention provide reduced potential for overdose, reduced potential for abuse or addiction and/or improve hydrocodone's characteristics with regard to high toxicities or suboptimal release profiles. Without wishing to be limited to the below theory, we believe that overdose protection results from a natural gating mechanism at the site of hydrolysis that limits the release of the active hydrocodone from the prodrug at greater than therapeutically prescribed amounts. Therefore, abuse resistance is provided by limiting the "rush" or "high" available from the active hydrocodone released by the prodrug and limiting the effectiveness of alternative routes of administration.

Throughout this application the use of "opioid" is meant to include any drug that activates the opioid receptors found in the brain, spinal cord and gut. There are three broad classes of opioids: naturally occurring opium alkaloids, such as morphine (the prototypical opioid) and codeine; semisynthetics such as heroine, oxycodone and hydrocodone that are produced by modifying natural opium alkaloids and have similar chemical structures; and pure synthetics such as fentanyl and methadone that are not produced from opium and may have very different chemical structures than the opium alkaloids. Other opioids include hydroxymorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

Throughout this application the use of "hydrocodone" is meant to include a semisynthetic narcotic analgesic and antitussive prepared from codeine with multiple actions qualitatively similar to those of codeine. It is commonly used for the relief of moderate to moderately severe pain. Trade names include Anexsia®, Hycodan®, Hycomine®, Lorcet®, Lortab®, Norco®, Tussionex®, Tylox®, and Vicodin®. Derivatives of hydrocodone, such as hydrocodone bitartrate and hydrocodone polistirex, are encompassed by the present invention.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein.

Throughout this application the use of "chemical moiety" is meant to include at least amino acids, peptides, glycopeptides, carbohydrates, lipids, nucleosides, or vitamins.

Carbohydrates includes sugars, starches, cellulose, and related compounds. e.g., $(CH_2O)_n$, wherein n is an integer larger than 2 or $C_n(H_2O)_{n-1}$, with n larger than 5. More specific examples include for instance, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A glycoprotein is a compound containing carbohydrate (or glycan) covalently linked to protein. The carbohydrate may be in the form of a monosaccharide, disaccharide(s), oligosaccharide(s), polysaccharide(s), or their derivatives (e.g. sulfo- or phospho-substituted).

A glycopeptide is a compound consisting of carbohydrate linked to an oligopeptide composed of L- and/or D-amino acids. A glyco-amino-acid is a saccharide attached to a single amino acid by any kind of covalent bond. A glycosyl-amino-acid is a compound consisting of saccharide linked through a glycosyl linkage (O-, N- or S-) to an amino acid.

A "composition" as used herein, refers broadly to any composition containing a described molecule conjugates. The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

Important note regarding stereochemistry: This patent is meant to cover all compounds discussed regardless of absolute configurations. Thus, natural, L-amino acids are discussed but the use of D-amino acids are also included.
BOC=t-butyloxycarbonyl
CMC=carboxymethylcellulose
DIPEA=di-isopropyl ethyl amine
mp=melting point
NMR=nuclear magnetic resonance
OSu=hydroxysuccinimido ester The attached chemical moiety may be any chemical substance that decreases the pharmacological activity until hydrocodone is released. Preferably the chemical moiety is a single amino acid, dipeptide or tripeptide. Hydrocodone binds to specific sites to produce various effects (Hoebel, et al., 1989). The attachment of certain chemical moieties can therefore diminish or prevent binding to these biological target sites. Preferably, absorption of the composition into the brain is prevented or substantially diminished and delayed when delivered by routes other than oral administration.

The attached chemical moiety may further comprise naturally occurring or synthetic substances. This would include but is not limited to the attachment of an hydrocodone to one or more amino acids, peptides, lipids, carbohydrates, glycopeptides, nucleic acids or vitamins. These chemical moieties could be expected to affect delayed release in the gastrointestinal tract and prevent rapid onset of the desired activity, particularly when delivered by parenteral routes. (Hoebel, B. G., L. Hernandez, et al. (1989). "Microdialysis studies of brain norepinephrine, serotonin, and dopamine release during ingestive behavior. Theoretical and clinical implications." *Ann NY Acad Sci* 575: 171-91).

For each of the recited embodiments the amino acid or peptide may comprise of one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more of the naturally occurring (D) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more unnatural, non-standard or synthetic amino acids such as, aminohexanoic acid, biphenylalanine, cyclohexylalanine, cyclohexylglycine, diethylglycine, dipropylglycine, 2,3-diaminoproprionic acid, homophenylalanine, homoserine, homotyrosine, naphthylalanine, norleucine, ornithine, pheylalanine(4-fluoro), phenylalanine(2,3,4,5,6 pentafluoro), phenylalanine(4-nitro), phenylglycine, pipecolic acid, sarcosine, tetrahydroisoquinoline-3-carboxylic acid, and tert-leucine. In another embodiment the amino acid or peptide comprises of one or more amino acid alcohols, for example, serine and threonine. In another embodiment the amino acid or peptide comprises of one or more N-methyl amino acids, for example, N-methyl aspartic acid.

The present invention provides covalent attachment of active agents to a peptide. The invention may be distinguished from the above mentioned technologies by virtue of covalently attaching the active agent directly, which includes, for example, pharmaceutical drugs and nutrients, to the N-terminus, the C-terminus or to the side chain of an amino acid, an oligopeptide or a polypeptide, also referred to herein as a carrier peptide. In another embodiment, when the active agent is itself an amino acid active agent, then the active agent may be part of the chain at either the C-terminus or N-terminus through a peptide bond, or interspersed in the polypeptide via peptide bonds on both sides of the active agent.

In another embodiment, the peptide stabilizes the active agent, primarily in the stomach, through conformational protection. In this application, delivery of the active agent is controlled, in part, by the kinetics of unfolding of the carrier peptide. Upon entry into the upper intestinal tract, endigenous enzymes release the active ingredient for absorption by the body by hydrolyzing the peptide bonds of the carrier peptide. This enzymatic action introduces the second phase of the sustained release mechanism.

In another embodiment, the invention provides a composition comprising a peptide and an active agent covalently attached to the peptide. Preferably, the peptide is (i) an oligopeptide, (ii) a homopolymer of one of the twenty naturally occurring amino acids (L or D isomers), or an isomer, analogue, or derivative thereof, (iii) a heteropolymer of two or more naturally occurring amino acids (L or D isomers), or an isomer, analogue, or derivative thereof, (iv) a homopolymer of a synthetic amino acid, (v) a heteropolymer of two or more synthetic amino acids or (vi) a heteropolymer of one or more naturally occurring amino acids and one or more synthetic amino acids.

The invention provides compositions comprising a carrier peptide and an active agent covalently attached to the carrier peptide. Preferably, the carrier peptide is (i) an amino acid, (ii) a dipeptide, (iii) a tripeptide, (iv) an oligopeptide, or (v) polypeptide. The carrier peptide may also be (i) a homopolymer of a naturally occurring amino acids, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids.

In another embodiment, the invention further provides a composition comprising an amino acid, a dipeptide or a tripeptide with an active agent covalently attached. Preferably, the amino acid, dipeptide or tripeptide are (i) one of the twenty naturally occurring amino acids (L or D isomers), or an isomer, analogue, or derivative thereof, (ii) two or more naturally occurring amino acids (L or D isomers), or an isomer, analogue, or derivative thereof, (iii) a synthetic amino acid, (iv) two or more synthetic amino acids or (v) one or more naturally occurring amino acids and one or more synthetic amino acids.

In another embodiment, the specific carriers are utilized as a base short chain amino acid sequence and additional amino acids are added to the terminus or side chain. In another embodiment, the above amino acid sequence may have one more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E], whereas histidine (His)[H] is similar to proline (Pro)[P], and glycine (Gly)[G] is similar to tryptophan (Trp)[W]. In the alternative the preferred amino acid substitutions may be selected according to hydrophilic properties (i.e. polarity) or other common characteristics associated with the 20 essential amino acids. While preferred embodiments utilize the 20 natural amino acids for their GRAS characteristics, it is recognized that minor substitutions along the amino acid chain which do not effect the essential characteristics of the amino are also contemplated.

In one embodiment the carrier range is between one to 12 chemical moieties with one to 8 moieties being preferred. In another embodiment the number of chemical moieties attached is selected from 1, 2, 3, 4, 5, 6, or 7. In another embodiment of the invention the molecular weight of the carrier portion of the conjugate is below about 2,500, more preferably below about 1,000 and most preferably below about 500.

In one embodiment the opioid is hydrocodone and the pharmaceutical carrier (chemical moiety) is comprised of a peptide of two or more amino acids. Preferred peptide chemical moieties include GluGluPhePheIle [SEQ ID NO: 5], TyrTyrIle, AspAspIle, TyrTyrPhePheIle [SEQ ID NO: 4].

In a preferred embodiment, the opioid is hydrocodone and the pharmaceutical carrier (chemical moiety) comprises a pentapeptide, such as TyrTyrPhePheIle [SEQ ID NO: 4], wherein the amino acids of the polypeptide are L-isomers. The compounds may designated by their generally accepted three or one-letter amino acid code followed by HC (for hydrocodone), such as TyrTyrPhePheIle[SEQ ID NO: 4]-HC or YYFFI[SEQ ID NO: 4]-HC. In another embodiment, the chemical moiety is a TyrTyrPhePheIle [SEQ ID NO: 4] bound to one or more additional amino acids. In another embodiment of the invention the molecular weight of the carrier portion of the conjugate is below about 2,500, more preferably below about 1,000 and most preferably below about 500.

Another embodiment of the invention is a composition for preventing overdose comprising an hydrocodone which has been covalently bound to a chemical moiety.

Another embodiment of the invention is a composition for safely delivering an hydrocodone comprising providing a therapeutically effective amount of said hydrocodone which has been covalently bound to a chemical moiety wherein said chemical moiety reduces the rate of absorption of the hydrocodone as compared to delivering the unbound hydrocodone.

Another embodiment of the invention is a composition for reducing drug toxicity comprising providing a patient with an hydrocodone which has been covalently bound to a chemical moiety wherein said chemical moiety increases the rate of clearance of a hydrocodone when given at doses exceeding those within the therapeutic range of said hydrocodone.

Another embodiment of the invention is a composition for reducing drug toxicity comprising providing a patient with an hydrocodone which has been covalently bound to a chemical moiety wherein said chemical moiety provides a serum release curve which does not increase above said hydrocodone toxicity level when given at doses exceeding those within the therapeutic range of said hydrocodone.

Another embodiment of the invention is a composition for reducing bioavailability of an hydrocodone comprising an hydrocodone covalently bound to a chemical moiety wherein said bound hydrocodone maintains a steady-state serum release curve which provides a therapeutically effective bioavailability but prevents spiking or increase blood serum concentrations compared to unbound hydrocodone when given at doses exceeding those within the therapeutic range of said hydrocodone.

Another embodiment of the invention is a composition for preventing a $C_{max}$ spike for an hydrocodone while still providing a therapeutically effective bioavailability curve comprising an hydrocodone which has been covalently bound to a chemical moiety.

Another embodiment of the invention is a composition for preventing a toxic release profile in a patient comprising hydrocodone covalently bound to a chemical moiety wherein said bound hydrocodone maintains a steady-state serum release curve which provides a therapeutically effective bioavailability but prevents spiking or increase blood serum concentrations compared to unbound hydrocodone.

Another embodiment of the invention is a compound of Formula I:

$$H\text{---}X_n\text{-}Z_m$$

wherein H is an hydrocodone as defined herein; X is a chemical moiety as defined herein and n is between 1 and 50 and increments thereof; and Z is a further chemical moiety different from X which acts as an adjuvant and m is between 1 and 50 and increments thereof. In another embodiment n is between 1 and 10 and m is 0. It should be recognized that the compounds of this formula may be used alone or in combination with any of the recited embodiments of the invention.

Embodiments of the invention provide hydrocodone compositions which allow the hydrocodone to be therapeutically effective when delivered at the proper dosage but reduces the rate of absorption or extent of bioavailability of the hydrocodone when given at doses exceeding those within the therapeutic range of the active agent. Embodiments of the invention also provide hydrocodone compositions wherein the covalently bound chemical moiety increases the rate of clearance of an hydrocodone when given at doses exceeding those within the therapeutic range of the hydrocodone.

In another embodiment the hydrocodone compositions have substantially lower toxicity compared to unbound active agent. In another embodiment the hydrocodone compositions reduce or eliminate the possibility of overdose by oral administration. In another embodiment the hydrocodone compositions reduce or eliminate the possibility of overdose by intranasal administration. In another embodiment the hydrocodone compositions reduce or eliminate the possibility of overdose by injection.

In another embodiment, the hydrocodone conjugates of the invention may further comprise a polymer blend which comprises at least one hydrophilic polymer and at least one water-insoluble polymer. The polymer may be used according to industry standard to further enhance the sustained release properties of the hydrocodone conjugate without reducing the abuse resistance. For instance, a composition might include: about 75% to about 95% hydrocodone conjugate by weight, from about 0.5% to about 10% of a hydrophilic polymer (e.g. hydroxypropyl methylcellulose), from about 0.5% to about 2.5% of a water-insoluble polymer (e.g. acrylic resin), from about 0.4% to about 1.5% of additives (e.g. magnesium stearate), and from about 0.01% to about 1% colorant by weight. Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and would dissolve slowly in aqueous acidic media thereby allowing the hydrocodone conjugate to diffuse from the gel in the stomach. When the gel reaches the intestines it would dissolve in controlled quantities in the higher pH medium to allow sustained release. Preferred hydrophilic polymers are the hydroxypropyl methylcelluloses such as those manufactured by The Dow Chemical Company and known as Methocel ethers, such as Methocel E10M.

Other formulations may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red No. 40, FD&C Yellow No. 6, D&C Yellow No. 10, or FD&C Blue No. 1 and other various certified color additives (See 21 CFR, Part 74). In one preferred embodiment, a sustained release formulation further comprises magnesium stearate and Emerald Green Lake.

An hydrocodone conjugate, which is further formulated with excipients may be manufactured according to any appropriate method known to those of skill in the art of pharmaceutical manufacture. For instance, the hydrocodone conjugate and a hydrophilic polymer may be mixed in a mixer with an aliquot of water to form a wet granulation. The granulation may be dried to obtain hydrophilic polymer encapsulated granules of hydrocodone-conjugate. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

However, it should be noted that the hydrocodone conjugate controls the release of hydrocodone into the digestive tract over an extended period of time resulting in an improved profile when compared to immediate release combinations and prevention of abuse without the addition of the above additives. In a preferred embodiment no further sustained release additives are required to achieve a blunted or reduced pharmacokinetic curve (e.g. reduced euphoric effect) while achieving therapeutically effective amounts of hydrocodone release.

The compounds of the invention can be administered by a variety of dosage forms. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, health bars, confections, animal feeds, cereals, yogurts, cereal coatings, foods, nutritive foods, functional foods and combinations thereof.

However, the most effective means for delivering the abuse-resistant compounds of the invention is orally, to permit maximum release of the hydrocodone to provide therapeutic effectiveness and/or sustained release while maintaining abuse resistance. When delivered by the oral route the hydrocodone is released into circulation, preferably over an extended period of time as compared to hydrocodone alone.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or lauryl-sulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient and the administration route. Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may further additionally include an indication of the above specified time periods for administering the compositions. For example the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the said pharmaceutical, particularly at doses above those intended for therapy. In another embodiment the decrease in bioavailability occurs upon oral administration. In another embodiment the decrease in bioavailability occurs upon intranasal administration. In another embodiment the decrease in bioavailability occurs upon intravenous administration.

Another particular embodiment of the invention provides that when the covalently modified hydrocodone is provided for oral dosing in the form (e.g., a tablet or capsule) it is resistant to manipulation. Crushing of the tablet or disruption of the capsule does not substantially increase the rate and amount of hydrocodone absorbed when compositions of the invention are ingested.

For each of the described embodiments one or more of the following characteristics may be realized. The toxicity of the compound is substantially lower than that of the unbound hydrocodone. The covalently bound chemical moiety reduces or eliminates the possibility of overdose by oral administration. The covalently bound chemical moiety reduces or eliminates the possibility of overdose by intranasal administration. The covalently bound chemical moiety reduces or eliminates the possibility of overdose by injection.

The invention further provides methods for altering hydrocodones in a manner that decreases their potential for abuse. Methods of the invention provide various ways to regulate pharmaceutical dosage through covalent attachment of hydrocodone to different chemical moieties. One embodiment provides a method of preventing overdose comprising administering to an individual hydrocodone which has been covalently bound to a chemical moiety.

Another embodiment provides a method of safely delivering hydrocodone comprising providing a therapeutically effective amount of a hydrocodone which has been covalently bound to a chemical moiety wherein the chemical moiety reduces the rate of absorption of hydrocodone as compared to delivering the unbound hydrocodone.

Another embodiment provides a method of reducing drug toxicity comprising providing a patient with hydrocodone which has been covalently bound to a chemical moiety wherein the chemical moiety increases the rate of clearance of a pharmacologically active hydrocodone when given at doses exceeding those within the therapeutic range of hydrocodone.

Another embodiment provides a method of reducing drug toxicity comprising providing a patient with hydrocodone which has been covalently bound to a chemical moiety wherein the chemical moiety provides a serum release curve which does not increase above the hydrocodone's toxicity level when given at doses exceeding those within the therapeutic range for the unbound hydrocodone.

Another embodiment provides a method of reducing bioavailability of a hydrocodone comprising providing hydrocodone covalently bound to a chemical moiety wherein the bound hydrocodone maintains a steady-state serum release curve which provides a therapeutically effective bioavailability but prevents spiking or increase blood serum concentrations compared to unbound hydrocodone when given at doses exceeding those within the therapeutic range for the unbound hydrocodone. Another embodiment provides a method of preventing a $C_{max}$ spike for hydrocodone while still providing a therapeutically effective bioavailability curve comprising providing hydrocodone which has been covalently bound to a chemical moiety. In another embodiment, methods of the invention provide bioavailability curves similar to those in the Figures, individually.

Another embodiment provides a method for preventing a toxic release profile in a patient comprising administering to a patient hydrocodone covalently bound to a chemical moiety wherein said bound hydrocodone maintains a steady-state serum release curve which provides a therapeutically effective bioavailability but prevents spiking or increase blood serum concentrations compared to unbound hydrocodone.

Another embodiment of the invention is a method for reducing or preventing abuse of a pharmaceutical composition, comprising providing, administering, or prescribing said composition to a human in need thereof, wherein said composition comprises a chemical moiety covalently attached to hydrocodone such that the pharmacological activity of hydrocodone is substantially decreased when the composition is used in a manner inconsistent with the manufacturer's instructions. Another embodiment of the invention is a method for reducing or preventing abuse of a pharmaceutical composition, comprising consuming said composition, wherein said composition comprises a chemical moiety covalently attached to hydrocodone such that the pharmacological activity of hydrocodone is substantially decreased when the composition is used in a manner inconsistent with the manufacturer's instructions.

Another embodiment of the invention is a method of preventing overdose of a pharmaceutical composition, comprising providing, administering, or prescribing said pharmaceutical composition to a human in need thereof, wherein said composition comprises a chemical moiety covalently attached to hydrocodone in a manner that substantially decreases the potential of overdose from hydrocodone. Another embodiment of the invention is a method of preventing overdose of a pharmaceutical composition, comprising consuming said pharmaceutical composition, wherein said composition comprises a chemical moiety covalently attached to hydrocodone in a manner that substantially decreases the potential of overdose from hydrocodone.

Another embodiment of the invention is a method for reducing or preventing the euphoric effect of a pharmaceutical composition, comprising providing, administering, or prescribing said composition to a human in need thereof, wherein said composition comprises a chemical moiety covalently attached to hydrocodone such that the pharmacological activity of hydrocodone is substantially decreased when the composition is used in a manner inconsistent with the manufacturer's instructions. Another embodiment of the invention is a method for reducing or preventing the euphoric effect of a pharmaceutical composition, comprising consuming said composition, wherein said composition comprises a chemical moiety covalently attached to hydrocodone such that the pharmacological activity of hydrocodone is substantially decreased when the composition is used in a manner inconsistent with the manufacturer's instructions.

Another embodiment of the invention is any of the preceding methods wherein said pharmaceutical composition is adapted for oral administration, and wherein said hydrocodone is resistant to release from said chemical moiety when the composition is administered parenterally, such as intranasally or intravenously. Preferably, said hydrocodone may be released from said chemical moiety in the presence of acid and/or enzymes present in the stomach, intestinal tract, or blood serum. Optionally, said composition may be in the form of a tablet, capsule, oral solution, or oral suspension.

Another embodiment of the invention is any of the preceding methods wherein said chemical moiety is an amino acid, oligopeptide, polypeptide, carbohydrate, glycopeptide, nucleic acid, or vitamin. Preferably, said chemical moiety is an amino acid, oligopeptide, or polypeptide. Where the chemical moiety is a polypeptide, preferably said polypeptide comprises fewer than 70 amino acids, fewer than 50 amino acids, fewer than 10 amino acids, or fewer than 6 amino acids. Where the chemical moiety is a polypeptide, preferably said polypeptide is TyrTyrPhePheIle [SEQ ID NO: 4].

Another embodiment of the invention is any of the preceding methods wherein said covalent attachment comprises an ester or carbonate bond. Another embodiment of the invention is any of the preceding methods wherein said hydrocodone covalently attaches to a chemical moiety through a ketone and/or hydroxyl in a pharmaceutically acceptable oral dosage form.

Another embodiment of the invention is any of the preceding methods wherein said composition yields a therapeutic effect without substantial euphoria. Preferably, said hydrocodone provides a therapeutically bioequivalent AUC when compared to active agent alone but does provide a $C_{max}$ which results in euphoria.

Another embodiment of the invention is a method for reducing or preventing abuse of a pharmaceutical composition, comprising orally administering said composition to a human in need thereof, wherein said composition comprises an amino acid or peptide (e.g., TyrTyrPhePheIle [SEQ ID NO: 4]) covalently attached to hydrocodone such that the pharmacological activity of hydrocodone is substantially decreased when the composition is used in a manner inconsistent with the manufacturer's instructions.

Another embodiment is a method of preventing overdose of a pharmaceutical composition, comprising orally administering said pharmaceutical composition to a human in need thereof, wherein said composition comprises an amino acid or peptide (e.g., TyrTyrPhePheIle [SEQ ID NO: 4]) covalently attached to hydrocodone in a manner that substantially decreases the potential of hydrocodone to result in overdose.

Another embodiment is a method for reducing or preventing the euphoric effect of a pharmaceutical composition, comprising orally administering said composition to a human in need thereof, wherein said composition comprises an amino acid or peptide (e.g., TyrTyrPhePheIle [SEQ ID NO: 4]) covalently attached to hydrocodone such that the pharmacological activity of hydrocodone is substantially decreased when the composition is used in a manner inconsistent with the manufacturer's instructions.

For each of the recited methods of the invention the following properties may be achieved through bonding hydrocodone to the chemical moiety. In one embodiment, the toxicity of the compound may be substantially lower than that of the hydrocodone when delivered in its unbound state or as a salt thereof. In another embodiment, the possibility of overdose by oral administration is reduced or eliminated. In another embodiment, the possibility of overdose by intranasal administration is reduced or eliminated. In another embodiment, the possibility of overdose by injection administration is reduced or eliminated.

Another embodiment of the invention provides methods of treating various diseases or conditions comprising administering compounds or compositions of the invention which further comprise commonly prescribed active agents for the respective illness or diseases wherein the hydrocodone is covalently attached to a chemical moiety. For instance, one embodiment of the invention comprises a method of treating narcotic addiction comprising administering to a patient compounds or compositions of the invention. Another embodiment of the invention provides a method of providing analgesia comprising administering to a patient compounds or compositions of the invention.

In order to facilitate a more complete understanding of the invention, Examples are provided below. However, the scope of the invention is not limited to specific embodiments disclosed in these Examples, which are for purposes of illustration only.

EXAMPLES

The Examples illustrate the applicability of attaching various moieties to hydrocodone to reduce the potential for overdose while maintaining therapeutic value. The invention is illustrated by pharmacokinetic studies with various peptide opioid conjugates. The pharmacokinetics of the parent opioid (e.g. hydrocodone) and major active metabolites (e.g. hydromorphone and oxymorphone) following oral, intravenous, or intranasal administration of the peptide-opioid conjugate or the parent drug at equimolar amounts were determined in rats. Some exemplary compounds include EEFFI[SEQ ID NO: 5]-HC, EEFFF[SEQ ID NO: 3]-HC, YYI-HC and YYFFI [SEQ ID NO: 4]-HC.

Oral, intranasal, and intravenous bioavailability studies of hydrocodone and hydrocodone conjugates were conducted in male Sprague-Dawley rats. Doses of hydrocodone bitartrate and hydrocodone conjugates containing equivalent amounts of hydrocodone were administered in deionized water. Oral administration was in 0.5 ml by gavage needle (with the exception of YYI-HC, which was delivered as a solid in gelatin capsules). Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Hydrocodone and hydromorphone (major active metabolite) concentrations were determined by LC/MS/MS.

The below examples are illustrative only and the below amino acid sequences attached to hydrocodone is not meant to be limiting. As such, synthesis and attachment of hydrocodone may be accomplished for instance view the following exemplary methods.

Hydrocodone Synthetic Examples Carbohydrates

Example 1

Galacto-Hydrocodone

FIG. 1 illustrates preparation of Galacto-Hydrocodone.

| Reagents | MW | Weight | mmoles | Molar Equivalents |
| --- | --- | --- | --- | --- |
| 1. Hydrocodone | 299 | 0.223 g | 0.75 | 1.0 |
| 1. LiN(TMS)$_2$ in THF | 1M | 1.13 ml | 1.13 | 1.5 |
| 1. DMF | — | 5 ml | — | — |
| 2. Galactose Chloroformate | — | — | 1.49 | 2.0 |
| 2. DMF | — | 3 ml | — | — |
| 3. 1M HCl | 1M | 30 ml | — | — |
| 3. Acetone | — | 20 ml | — | — |

Galacto-Hydrocodone

To a solution of hydrocodone in DMF was added LiN(TMS)$_2$ in THF via syringe. The solution was stirred at ambient temperatures for 5 minutes then the chloroformate of galactose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 6M HCl. Solvent was removed. Final product was purified using preparative TLC (0-10% MeOH in CHCl$_3$). Solid was collected as a white powder (0.180 g, 41% yield): $^1$H NMR (DMSO-d$_6$) δ 1.28 (2 s, 6H), 1.37 (s, 3H), 1.44 (3, 3H), 1.49 (m, 2H), 1.88 (dt, 1H), 2.08 (m, 2H), 2.29 (s, 4H), 2.40 (m, 2H), 2.90 (d, 1H), 3.09 (s, 1H), 3.73 (s, 3H), 3.99 (dd, 1H), 4.14 (t, 1H), 4.26 (dt, 2H), 4.39 (d, 1H), 4.63 (d, 1H), 4.95 (s, 1H), 5.48 (d, 1H), 5.68 (d, 1H), 6.65 (d, 1H), 6.74 (d, 1H); MS Calculated mass=585.6. Found=586.4 (M+H).

To the protected galactose intermediate was added 30 ml of 1M HCl and 20 ml acetone. The resulting solution was stirred at ambient temperatures for 3 hours. Solvent was removed and final product dried under vacuum. Solid was collected as a white solid: MS Calculated mass=505.5. Found=506.4 (M+H).

Figure 2:
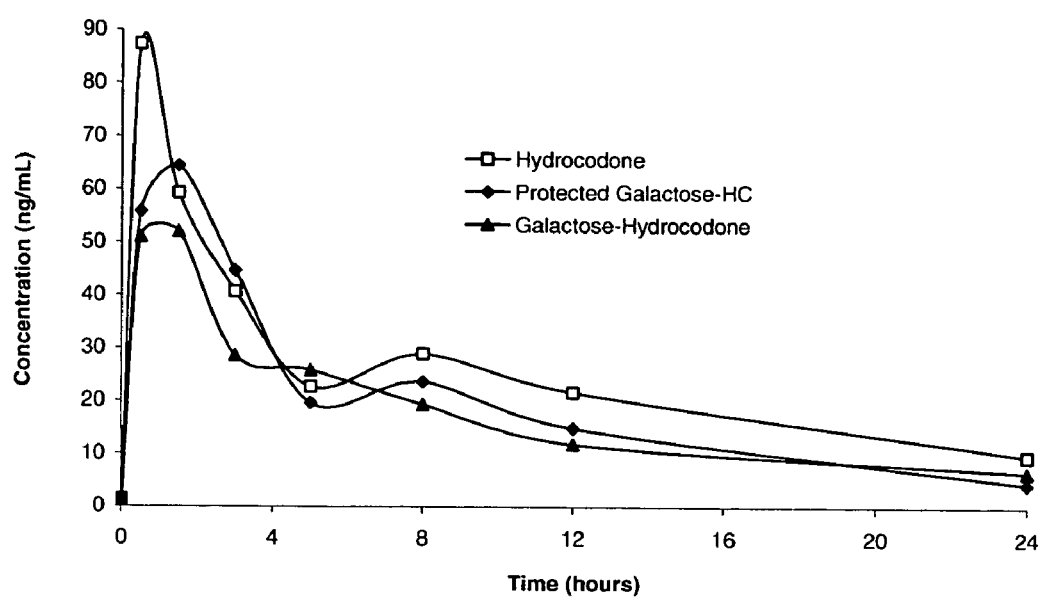
FIG. 2. Oral bioavailability of abuse-resistant hydrocodone carbohydrate conjugates, measured as free hydrocodone (with measured plasma levels by ELISA).

FIG. 2 depicts oral bioavailability of abuse-resistant hydrocodone carbohydrate conjugates, measured as free hydrocodone (with measured plasma levels by ELISA).

Example 2

Ribo-Hydrocodone

Figure 3:
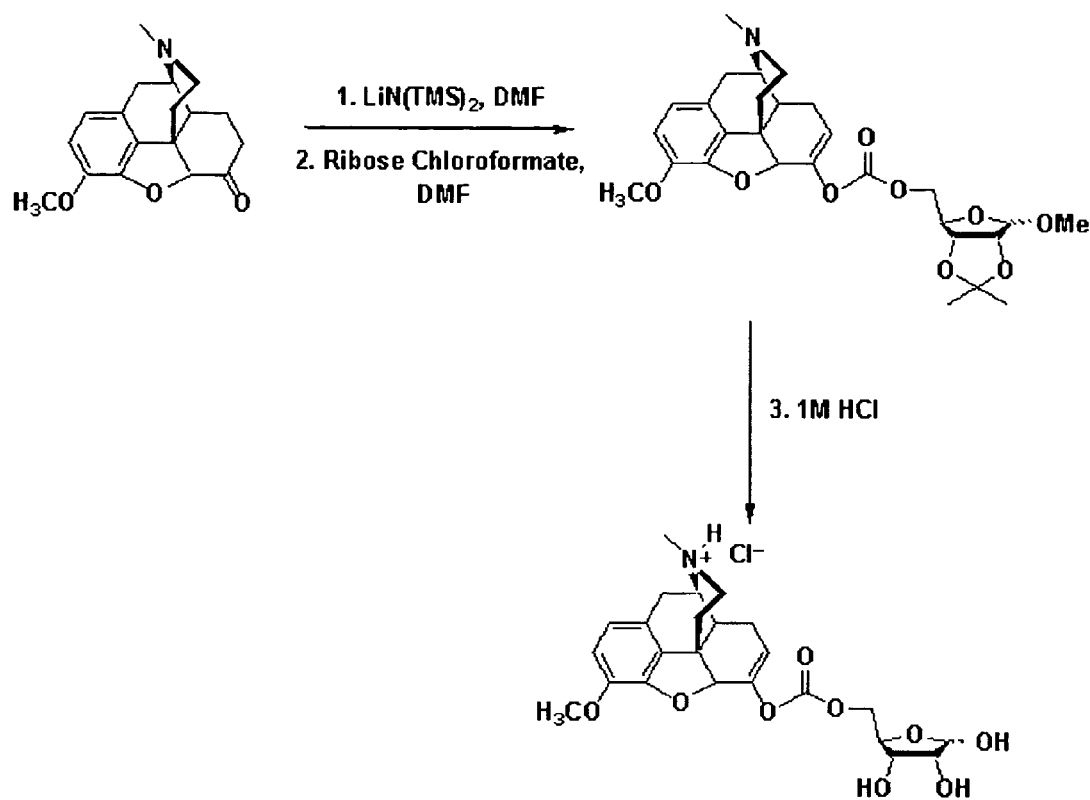
FIG. 3. illustrates preparation of Ribo-Hydrocodone.

FIG. 3 illustrates preparation of Ribo-Hydrocodone.

| Reagents | MW | Weight | mmoles | Molar Equivalents |
| --- | --- | --- | --- | --- |
| 1. Hydrocodone | 299 | 0.733 g | 2.45 | 1.0 |
| 1. LiN(TMS)$_2$ in THF | 1M | 3.68 ml | 3.68 | 1.5 |
| 1. DMF | — | 8 ml | — | — |
| 2. Ribose Chloroformate | — | — | 4.90 | 2.0 |
| 2. DMF | — | 3 ml | — | — |
| 3. 1M HCl | 1M | 10 ml | — | — |

Ribo-Hydrocodone

To a solution of hydrocodone in DMF was added LiN(TMS)$_2$ in THF via syringe. The solution was stirred at ambient temperatures for 5 minutes then the chloroformate of ribose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 1M HCl. Solvent was removed. Crude product was taken up in CHCl$_3$ (50 ml), washed with water (3×50 ml), dried over MgSO$_4$, filtered and solvent removed. Final product was purified using preparative HPLC (10 mM CH$_3$COONH$_4$/MeCN; 0-20 min: 80/20→0/100). Solid was collected as a clear, colorless glass (0.095 g, 7% yield): $^1$H NMR (DMSO-d$_6$) δ 1.26 (s, 3H), 1.39 (s, 3H), 1.50 (m, 2H), 1.89 (s, 4H), 2.08 (m, 2H), 2.29 (s, 4H), 2.40 (m, 2H), 2.88 (d, 1H), 3.08 (m, 1H), 3.25 (s, 3H), 3.73 (s, 3H), 4.12 (m, 2H), 4.28 (t, 1H), 4.58 (d, 1H), 4.72 (d, 1H), 4.97 (s, 1H), 4.98 (s, 1H), 5.70 (s, 1H), 6.66 (d, 1H), 6.75 (d, 1H). MS Calculated mass=529.2. Found=530.4 (M+H).

To the protected ribose intermediate was added 10 ml of 1M HCl. The resulting solution was stirred at ambient temperatures for 2 hours. Solvent was removed and final product dried under vacuum. Solid was collected as a waxy, slightly yellow solid (0.092 g, quant.): $^1$H NMR (DMSO-d$_6$)

δ 1.51 (t, 1H), 1.83 (d, 1H), 2.41 (dt, 1H), 2.27 (t, 1H), 2.63 (dd, 1H), 2.80 (s, 3H), 2.96 (m, 2H), 3.20 (m, 1H), 3.75 (s, 3H), 3.82-4.34 (br m, 12H), 5.15 (s, 1H), 5.72 (s, 1H), 6.75 (d, 1H), 6.88 (d, 1H), 11.37 (br s, 1H).

Figure 4:
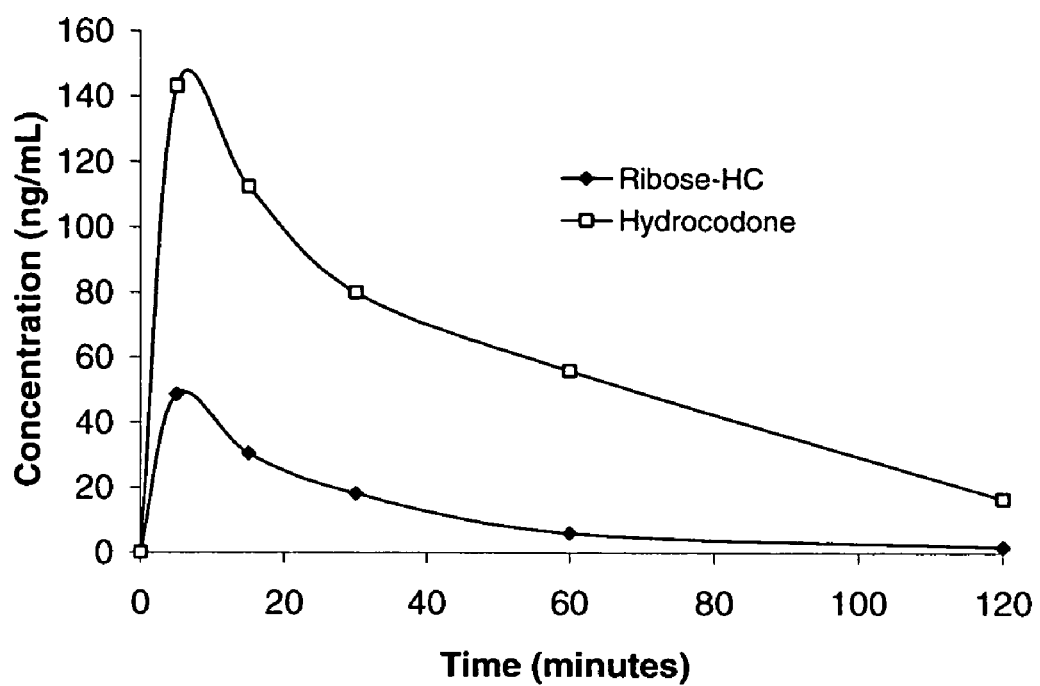
FIG. 4. Intranasal bioavailability of abuse-resistant hydrocodone carbohydrate conjugate, measured as free hydrocodone (with measured plasma levels by ELISA).

FIG. 4 illustrates intranasal bioavailability of abuse-resistant hydrocodone carbohydrate conjugate, measured as free hydrocodone (with measured plasma levels by ELISA).

Single Amino Acids

Example 3

Leu-Hydrocodone

Figure 5:
FIG. 5. illustrates preparation of Leu-Hydrocodone.

FIG. 5 illustrates preparation of Leu-Hydrocodone.

| Reagents | MW | Weight | mmoles | Molar Equivalents |
|---|---|---|---|---|
| 1. Hydrocodone | 299 | 1.00 g | 3.34 | 1.0 |
| 1. LiN(TMS)$_2$ in THF | 1M | 10.5 ml | 10.5 | 3.15 |
| 1. THF | — | 25 ml | — | — |
| 2. Boc-Leu-OSu | 328 | 3.28 g | 10.0 | 3.0 |

Leu-Hydrocodone

To a solution of hydrocodone in THF was added LiN(TMS)$_2$ in THF via syringe. The solution was stirred at ambient temperatures for 5 minutes then Boc-Leu-OSu was added. The resulting reaction mixture was stirred at ambient temperatures for 18 hours. Reaction was neutralized to pH 7 with 6M HCl. Solvent was removed. Crude material was taken up in CHCl$_3$ (100 ml), washed with sat. NaHCO$_3$ (3×100 ml), dried over MgSO$_4$, filtered, and solvent removed. Solid was collected as a yellow powder (1.98 g, 95% yield): $^1$H NMR (DMSO-d$_6$) δ 0.86 (dd, 6H), 1.31 (s, 9H), 1.46 (s, 2H), 1.55 (m, 2H), 1.69 (m, 1H), 1.87 (dt, 1H), 2.07 (dt, 2H), 2.29 (s, 3H), 2.43 (m, 2H), 2.93 (d, 1H), 3.11 (s, 1H), 3.72 (s, 3H), 3.88 (dt, 1H), 4.03 (dt, 1H), 4.87 (s, 1H), 5.51 (d, 1H), 6.65 (d, 1H), 6.73 (d, 1H), 6.90 (s, 1H).

To the Boc-Leu-Hydrocodone was added 25 ml of 4N HCl in dioxane. The resulting mixture was stirred at ambient temperatures for 18 hours. Solvent was removed and final product dried under vacuum. Solid was collected as a slightly yellow solid (1.96 g, 97% yield): $^1$H NMR (DMSO-d$_6$) δ 0.94 (d, 6H), 1.52 (m, 1H), 1.75-1.90 (m, 4H), 2.22 (dt, 1H), 2.34 (dt, 1H), 2.64 (q, 1H), 2.75 (s, 3H), 2.95-3.23 (m, 4H), 3.74 (s, 3H), 3.91 (d, 1H), 4.07 (s, 1H), 5.10 (s, 1H), 5.72 (d, 1H), 6.76 (d, 1H), 6.86 (d, 1H), 8.73 br s, 3H).

Example 4

Glu-Hydrocodone

Synthesis of Glu-Hydrocodone

Glu-Hydrocodone was prepared by a similar method to Example 3 except the amino acid starting material was Boc-Glu(OtBu)-OSu.

Example 5

Ile-Hydrocodone

Synthesis of Ile-Hydrocodone

Ile-Hydrocodone was prepared by a similar method to Example 3 except the amino acid starting material was Boc-Ile-OSu.

Dipeptides

Figure 6:
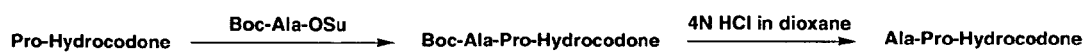
FIG. 6. illustrates preparation of Ala-Pro-Hydrocodone.

FIG. 6 illustrates preparation of Ala-Pro-Hydrocodone.

Example 6

Ala-Pro-Hydrocodone

| Reagents | MW | Weight | mmoles | Molar Equivalents |
|---|---|---|---|---|
| Pro-Hydrocodone | 468 | 0.25 g | 0.53 | 1.0 |
| Boc-Ala-OSu | 286 | 0.33 g | 1.2 | 2.26 |
| NMM | 101 | 0.50 ml | 5.38 | 10.2 |
| DMF | — | 10 ml | — | — |

Ala-Pro-Hydrocodone

To a solution of Pro-Hydrocodone in DMF was added NMM followed by Boc-Ala-OSu. The solution was stirred at ambient temperatures for 18 hours. Solvent was removed. Crude material was purified using preparative HPLC (Phenomenex Luna C18, 30×250 mm, 5 μM, 100 Å; Gradient: 100 water/0 0.1% TFA-MeCN→0/100; 30 ml/min.). Solid was collected as a slightly yellow powder (0.307 g, 85% yield): $^1$H NMR (DMSO-d$_6$) δ 1.16 (d, 3H), 1.35 (s, 9H), 1.51 (m, 2H), 1.86-2.10 (m, 6H), 2.50 (m, 1H), 2.54 (m, 1H), 2.69 (m, 1H), 2.88 (s, 3H), 3.02 (dd, 1H), 3.26 (d, 1H), 3.55 (m, 1H), 3.67 (m, 1H), 3.72 (s, 3H), 3.80 (s, 1H), 4.25 (m, 1H), 4.43 (d, 1H), 5.01 (s, 1H), 5.59 (d, 1H), 6.75 (d, 1H), 6.88 (d, 1H), 6.99 (t, 1H), 9.91 (br s, 1H).

To the Boc-Ala-Pro-Hydrocodone (0.100 g) was added 10 ml of 4N HCl in dioxane. The resulting mixture was stirred at ambient temperatures for 18 hours. Solvent was removed and final product dried under vacuum. Solid was collected as a slightly yellow solid (0.56 g, 71% yield): $^1$H NMR (DMSO-d$_6$) δ 1.38 (s, 3H), 1.48 (t, 1H), 1.80-2.29 (m, 8H), 2.65 (m, 1H), 2.80 (s, 3H), 2.96 (m, 3H), 3.23 (m, 2H), 3.76 (s, 3H), 3.92 (s, 1H), 4.22 (s, 1H), 4.53 (s, 1H), 5.00 (s, 1H), 5.84 (d, 1H), 6.77 (d, 1H), 6.86 (d, 1H), 8.25 (br s, 3H).

Example 7

Glu-Glu-Hydrocodone

Synthesis of Glu-Glu-Hydrocodone

Glu-Glu-Hydrocodone was prepared by a similar method to Example 6 except the amino acid starting material was Boc-Glu(OtBu)-OSu and the conjugate starting material was Glu-Hydrocodone.

Example 8

(pyro)Glu-Glu-Hydrocodone

Synthesis of (pyro)Glu-Glu-Hydrocodone

The compound (pyro)Glu-Glu-Hydrocodone was prepared by a similar method to Example 6 except the amino acid starting material was Boc-pyroglutamic acid-OSu and the conjugate starting material was Glu-Hydrocodone.

Tripeptides

Figure 7:
FIG. 7. illustrates the preparation of Gly-Gly-Leu-Hydrocodone.

FIG. 7 illustrates the preparation of Gly-Gly-Leu-Hydrocodone.

Example 9

Gly-Gly-Leu-Hydrocodone

| Reagents | MW | Weight | mmoles | Molar Equivalents |
|---|---|---|---|---|
| Leu-Hydrocodone | 484 | 2.21 g | 4.56 | 1.0 |
| Boc-Gly-Gly-OSu | 329 | 3.00 g | 9.12 | 2.0 |
| NMM | 101 | 5.0 ml | 45.6 | 10 |
| DMF | — | 100 ml | — | — |

Gly-Gly-Leu-Hydrocodone

To a solution of Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 µM, 100 Å; Gradient: 90 water/10 0.1% TFA-MeCN→0/100; 30 ml/min.). Solid was collected as a slightly yellow powder (2.08 g, 73% yield): $^1$H NMR (DMSO-$d_6$) δ 0.88 (dd, 6H), 1.38 (s, 9H), 1.53-1.72 (m, 5H), 1.89 (d, 1H), 2.15 (m, 1H), 2.67 (m, 2H), 2.94 (s, 3H), 3.05 (m, 2H), 3.25 (m, 2H), 3.56 (d, 3H), 3.76 (s, 6H), 3.98 (s, 1H), 4.35 (q, 1H), 5.04 (s, 1H), 5.59 (d, 1H), 6.77 (d, 1H), 6.85 (d, 1H), 7.04 (t, 1H), 8.01 (t, 1H), 8.30 (d, 1H), 9.99 (br s, 1H).

To the Boc-Gly-Gly-Leu-Hydrocodone (2.08 g) was added 50 ml of 4N HCl in dioxane. The resulting mixture was stirred at ambient temperatures for 18 hours. Solvent was removed and final product dried under vacuum. Solid was collected as a slightly yellow solid (1.72 g, 86% yield): $^1$H NMR (DMSO-$d_6$) δ 0.89 (dd, 6H), 1.50-1.87 (m, 5H), 2.26 (m, 2H), 2.66 (m, 2H), 2.82-2.97 (m, 5H), 3.21 (m, 2H), 3.60 (m, 4H), 3.88 (m, 5H), 4.37 (m, 1H), 5.04 (s, 1H), 5.60 (s, 1H), 6.79 (d, 2H), 8.07 (br s, 3H), 8.54 (br s, 1H), 8.66 (br s, 1H), 11.29 (br s, 1H).

Example 10

Glu-Glu-Glu-Hydrocodone

Synthesis of Glu-Glu-Glu-Hydrocodone

Glu-Glu-Glu-Hydrocodone was prepared by a similar method to Example 9 except the amino acid starting material was Boc-Glu(OtBu)-Glu(OtBu)-OSu and the conjugate starting material was Glu-Hydrocodone.

Example 11

Pro-Pro-Leu-Hydrocodone

Synthesis of Pro-Pro-Leu-Hydrocodone

Pro-Pro-Leu-Hydrocodone was prepared by a similar method to Example 9 except the amino acid starting material was Boc-Pro-Pro-OSu.

Example 12

Leu-Leu-Leu-Hydrocodone

Synthesis of Leu-Leu-Leu-Hydrocodone

Leu-Leu-Leu-Hydrocodone was prepared by a similar method to Example 9 except the amino acid starting material was Boc-Leu-Leu-OSu.

Example 13

Pro-Pro-Ile-Hydrocodone

Synthesis of Pro-Pro-Ile-Hydrocodone

Pro-Pro-Ile-Hydrocodone was prepared by a similar method to Example 9 except the amino acid starting material was Boc-Pro-Pro-OSu and the conjugate starting material was Ile-Hydrocodone.

Example 14

Leu-Pro-Leu-Hydrocodone

Synthesis of Leu-Pro-Leu-Hydrocodone

Leu-Pro-Leu-Hydrocodone was prepared by a similar method to Example 9 except the amino acid starting material was Boc-Leu-Pro-OSu.

Example 15

Lys-Lys-Ile-Hydrocodone

Synthesis of Lys-Lys-Ile-Hydrocodone

Lys-Lys-Ile-Hydrocodone was prepared by a similar method except the amino acid starting material was Boc-Lys(Boc)-Lys(Boc)-OSu and the conjugate starting material was Ile-Hydrocodone.

Example 16

Glu-Glu-Ile-Hydrocodone

Synthesis of Glu-Glu-Ile-Hydrocodone

Glu-Glu-Ile-Hydrocodone was prepared by a similar method to Example 9 except the amino acid starting material was Boc-Glu(OtBu)-Glu(OtBu)-OSu and the conjugate starting material was Ile-Hydrocodone.

Example 17

Tyr-Tyr-Ile-Hydrocodone

Synthesis of Tyr-Tyr-Ile-Hydrocodone

Tyr-Tyr-Ile-Hydrocodone was prepared by a similar method to Example 9 except the amino acid starting material was Boc-Tyr(tBu)-Tyr(tBu)-OSu and the conjugate starting material was Ile-Hydrocodone.

Pentapeptides

Example 18

Gly-Gly-Leu-Hydrocodone

Figure 8:
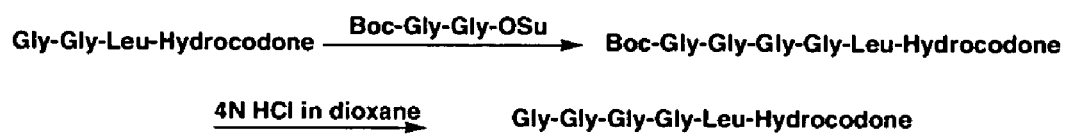
FIG. 8. illustrates preparation of Gly-Gly-Gly-Gly-Leu [SEQ ID NO: 1]-Hydrocodone.
Figure 9:
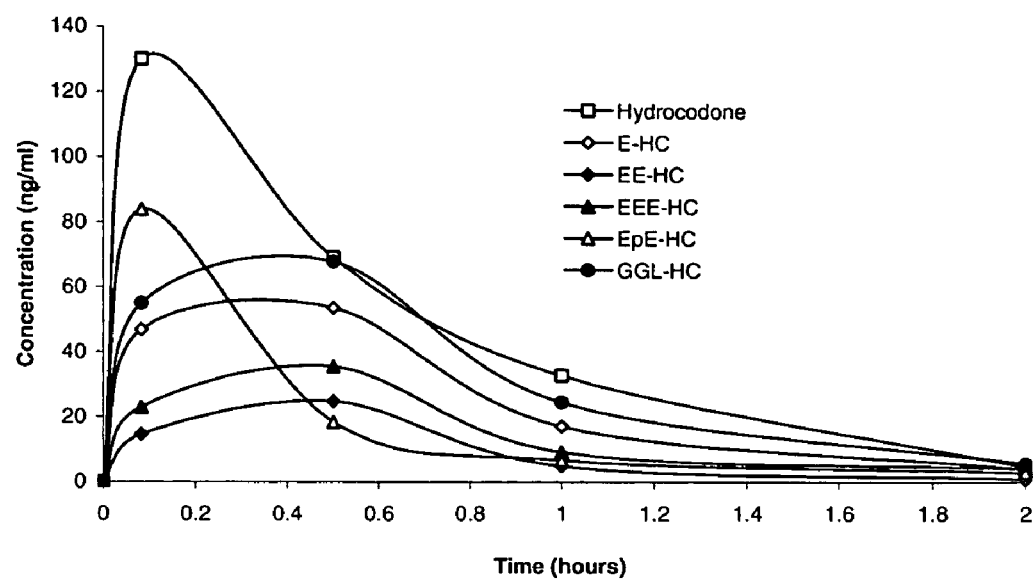
FIG. 9. Intranasal bioavailability of abuse-resistant hydrocodone amino acid, di- and tri-peptide conjugates, measured as free hydrocodone.
Figure 10:
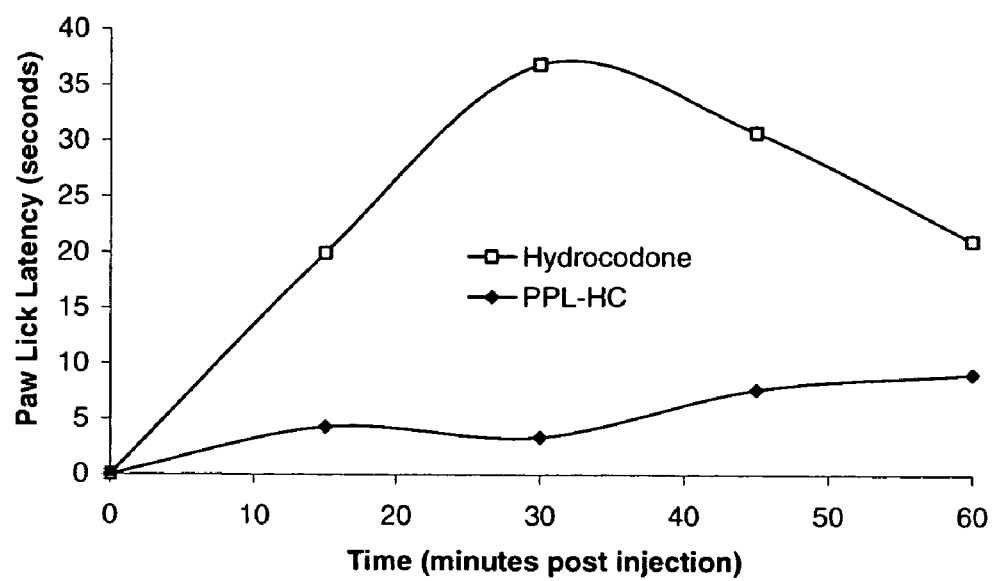
FIG. 10. Analgesic effect of abuse-resistant hydrocodone tri-peptide conjugate following intranasal administration, measured as free hydrocodone.
Figure 11:
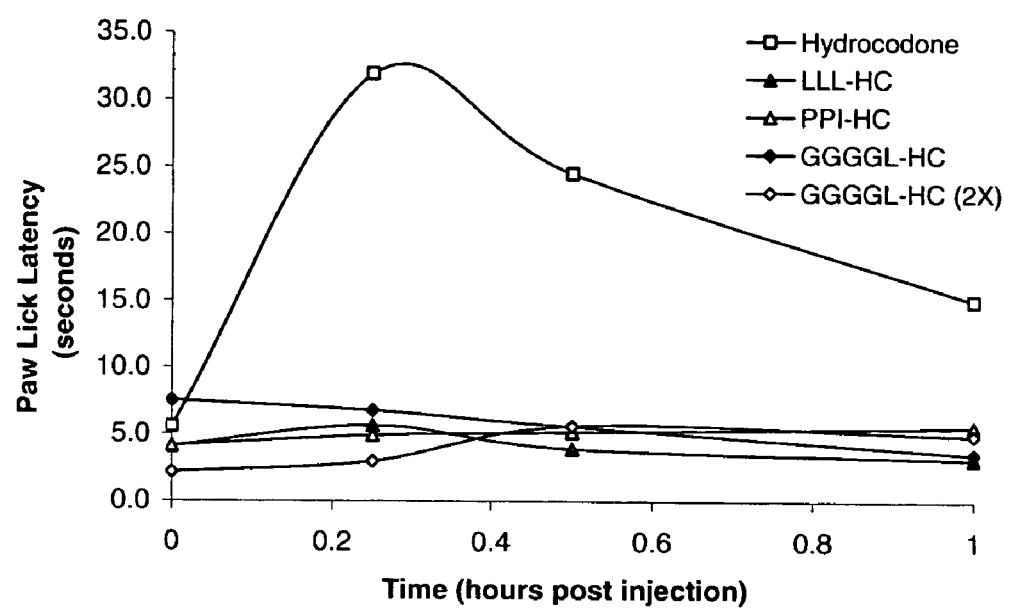
FIG. 11. Analgesic effect of abuse-resistant hydrocodone tri- and penta-peptide conjugates following subcutaneous administration, measured as free hydrocodone.
Figure 12:
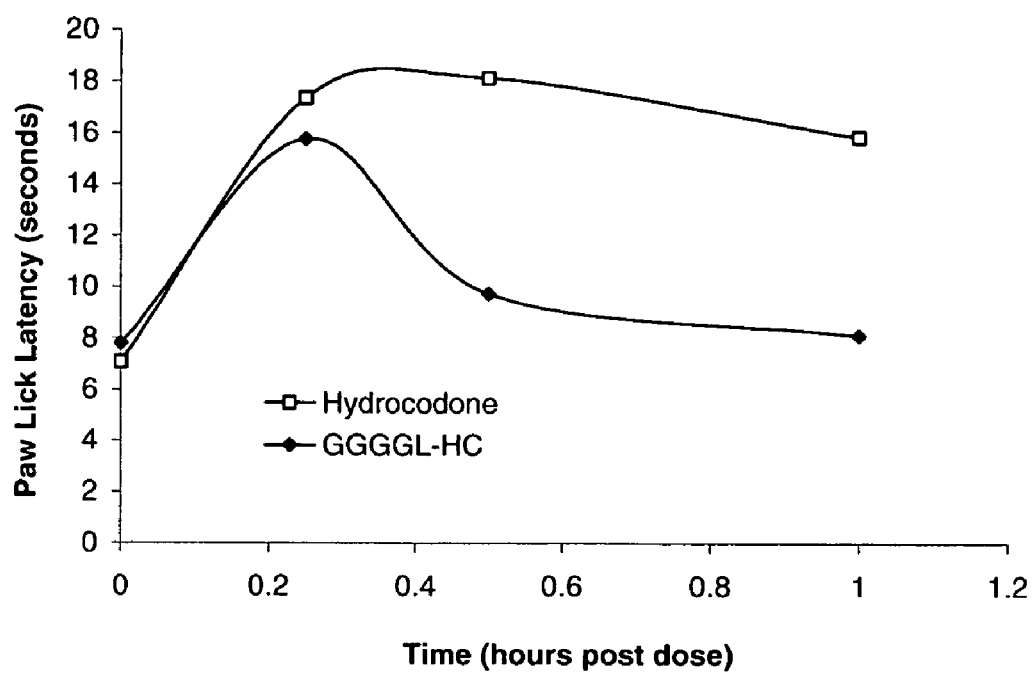
FIG. 12. Analgesic effect of abuse-resistant hydrocodone penta-peptide conjugate following intranasal administration, measured as free hydrocodone.
Figure 13:
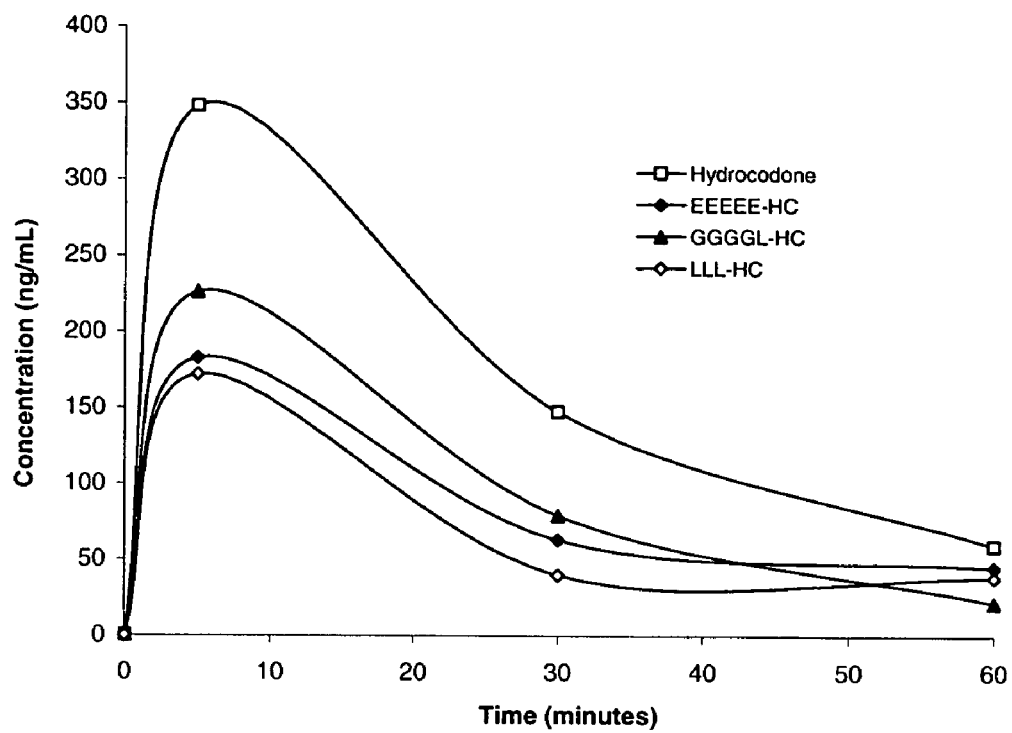
FIG. 13. Intranasal bioavailability of abuse-resistant hydrocodone tri- and penta-peptide conjugates, measured as free hydrocodone.
Figure 14:
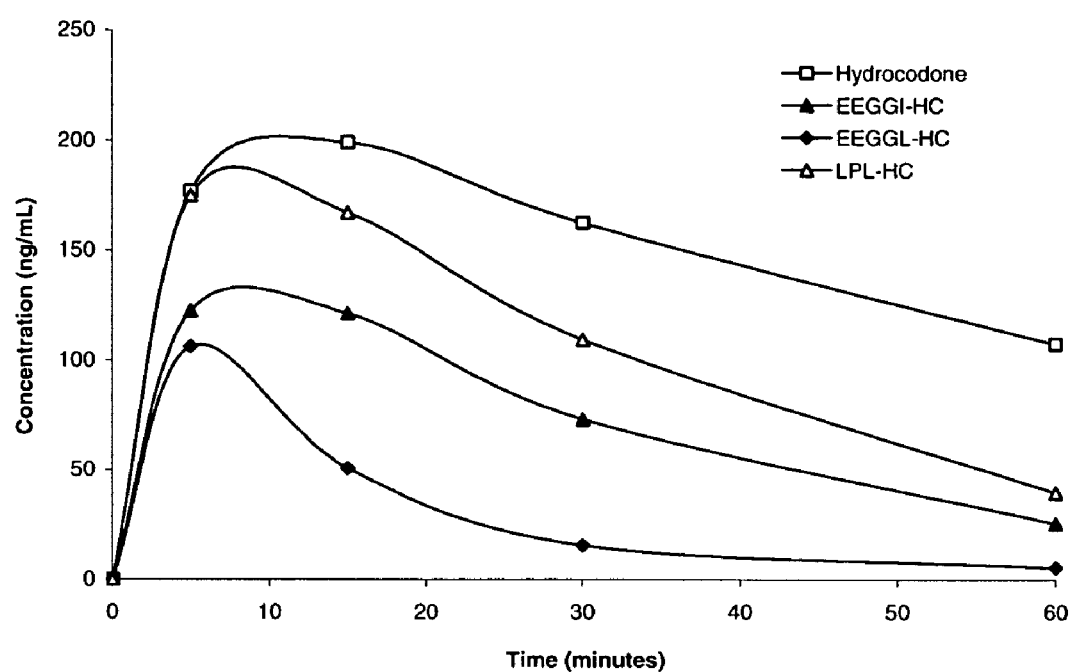
FIG. 14. Intranasal bioavailability of abuse-resistant hydrocodone tri- and penta-peptide conjugates, measured as free hydrocodone.
Figure 15:
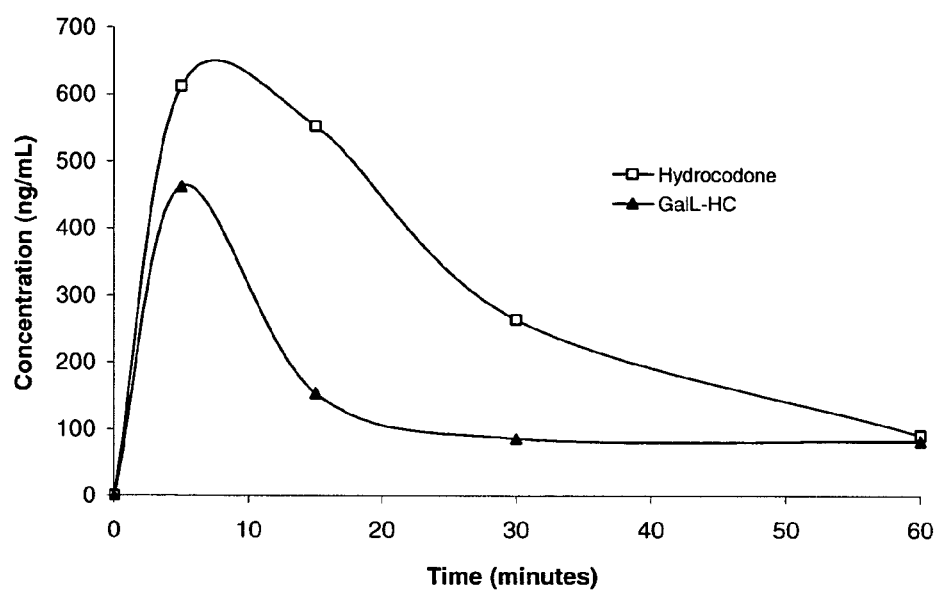
FIG. 15. Intranasal bioavailability of abuse-resistant hydrocodone an amino acid-carbohydrate peptide conjugate, measured as free hydrocodone.
Figure 16:
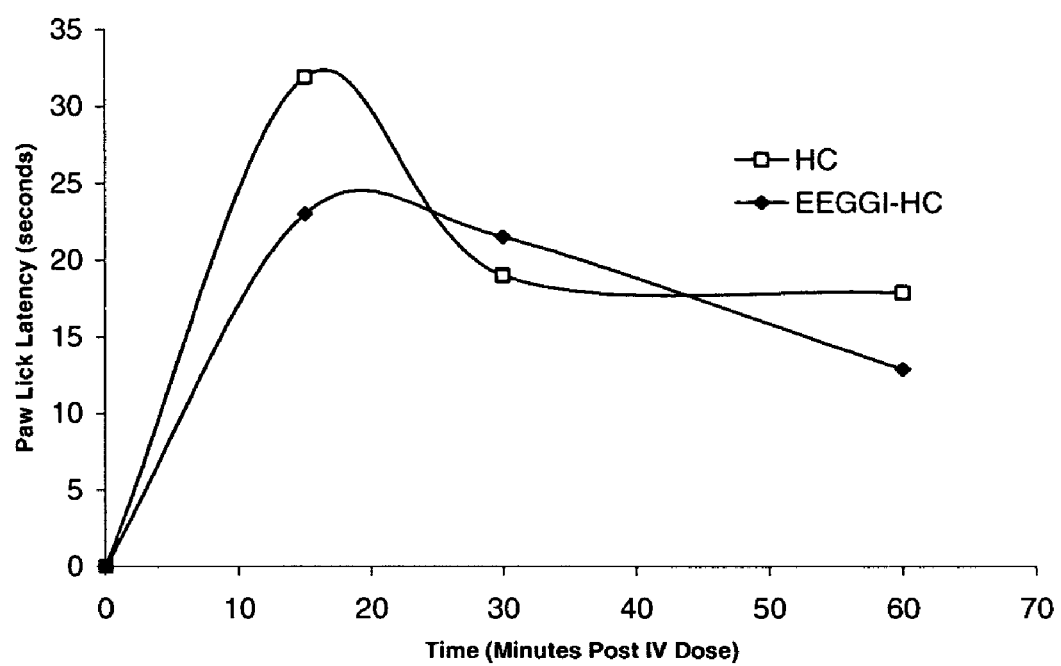
FIG. 16. Analgesic effect of abuse-resistant hydrocodone penta-peptide conjugate following intravenous administration, measured as free hydrocodone.

FIG. 8 illustrates preparation of Gly-Gly-Gly-Gly-Leu-Hydrocodone.

| Reagents | MW | Weight | mmoles | Molar Equivalents |
|---|---|---|---|---|
| Gly-Gly-Leu-Hydrocodone | 599 | 0.580 g | 0.970 | 1.0 |
| Boc-Gly-Gly-OSu | 329 | 0.638 g | 1.94 | 2.0 |

-continued

| Reagents | MW | Weight | mmoles | Molar Equivalents |
|---|---|---|---|---|
| NMM | 101 | 1.06 ml | 9.70 | 10 |
| DMF | — | 20 ml | — | — |

Gly-Gly-Gly-Gly-Leu[SEQ ID NO: 1]-Hydrocodone

To a solution of Gly-Gly-Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 85 water/15 0.1% TFA-MeCN→50/50; 30 ml/min.). Solid was collected as a slightly yellow powder (0.304 g, 37% yield).

To the Boc-Gly-Gly-Gly-Gly-Leu [SEQ ID NO: 8]-Hydrocodone (0.304 g) was added 25 ml of 4N HCl in dioxane. The resulting mixture was stirred at ambient temperatures for 18 hours. Solvent was removed and final product dried under vacuum. Solid was collected as a slightly yellow solid (0.247 g, 97% yield): $^1$H NMR (DMSO-$d_6$) δ 0.87 (m, 6H), 1.23 (s, 1H), 1.51-1.86 (m, 4H), 2.18 (m, 1H), 2.71 (m, 2H), 2.77 (s, 3H), 2.96 (m, 2H), 3.17 (m, 2H), 3.61 (s, 3H), 3.81-3.84 (m, 10H), 4.22 (m, 1H), 4.36 (m, 1H), 5.09 (m, 1H), 5.59 (d, 1H), 6.74 (dd, 2H), 8.16 (br s, 4H), 8.38 (br s, 1H), 8.74 (br s, 1H), 11.42 (br s, 1H).

Example 19

Glu-Glu-Glu-Glu-Glu [SEQ ID NO: 9]-Hydrocodone

Synthesis of Glu-Glu-Glu-Glu-Glu [SEQ ID NO: 9]-Hydrocodone

Glu-Glu-Glu-Glu-Glu [SEQ ID NO: 9]-Hydrocodone was prepared by a similar method to Example 18 except the amino acid starting material was Boc-Glu(OtBu)-Glu(OtBu)-OSu and the conjugate starting material was Glu-Glu-Glu-Hydrocodone.

Example 20

Glu-Glu-Gly-Gly-Ile [SEQ ID NO: 10]-Hydrocodone

Synthesis of Glu-Glu-Gly-Gly-Ile [SEQ ID NO: 10]-Hydrocodone

Glu-Glu-Gly-Gly-Ile [SEQ ID NO: 10]-Hydrocodone was prepared by a similar method to Example 18 except the amino acid starting material was Boc-Glu(OtBu)-Glu(OtBu)-OSu and the conjugate starting material was Gly-Gly-Ile-Hydrocodone.

Example 21

Glu-Glu-Gly-Gly-Leu [SEQ ID NO: 11]-Hydrocodone

Synthesis of Glu-Glu-Gly-Gly-Leu [SEQ ID NO: 11]-Hydrocodone

Glu-Glu-Gly-Gly-Leu [SEQ ID NO: 11]-Hydrocodone was prepared by a similar method to Example 18 except the amino acid starting material was Boc-Glu(OtBu)-Glu(OtBu)-OSu and the conjugate starting material was Gly-Gly-Leu-Hydrocodone.

Example 22

Gly-Gly-Gly-Gly-Ile [SEQ ID NO: 12]-Hydrocodone

Synthesis of Gly-Gly-Gly-Gly-Ile [SEQ ID NO: 12]-Hydrocodone

Gly-Gly-Gly-Gly-Ile [SEQ ID NO: 12]-Hydrocodone was prepared by a similar method to Example 18 except the amino acid starting material was Boc-Gly-Gly-OSu and the conjugate starting material was Gly-Gly-Ile-Hydrocodone.

Example 23

Glu-Glu-Phe-Phe-Phe [SEQ ID NO: 3]-Hydrocodone

Synthesis of Glu-Glu-Phe-Phe-Phe [SEQ ID NO: 3]-Hydrocodone

Glu-Glu-Phe-Phe-Phe [SEQ ID NO: 3]-Hydrocodone was prepared by a similar method to Example 18 except the amino acid starting material was Boc-Glu(OtBu)-Glu(OtBu)-OSu and the conjugate starting material was Phe-Phe-Phe-Hydrocodone.

Example 24

Lys-Lys-Gly-Gly-Ile [SEQ ID NO: 13]-Hydrocodone

Synthesis of Lys-Lys-Gly-Gly-Ile [SEQ ID NO: 13]-Hydrocodone

Lys-Lys-Gly-Gly-Ile [SEQ ID NO: 13]-Hydrocodone was prepared by a similar method to Example 18 except the amino acid starting material was Boc-Lys(Boc)-Lys(Boc)-OSu and the conjugate starting material was Gly-Gly-Ile-Hydrocodone.

Example 25

Lys-Lys-Pro-Pro-Ile [SEQ ID NO: 6]-Hydrocodone

Synthesis of Lys-Lys-Pro-Pro-Ile [SEQ ID NO: 6]-Hydrocodone

Lys-Lys-Pro-Pro-Ile [SEQ ID NO: 6]-Hydrocodone was prepared by a similar method to Example 18 except the amino acid starting material was Boc-Lys(Boc)-Lys(Boc)-OSu and the conjugate starting material was Pro-Pro-Ile-Hydrocodone.

Example 26

Tyr-Tyr-Gly-Gly-Ile [SEQ ID NO: 14]-Hydrocodone

Synthesis of Tyr-Tyr-Gly-Gly-Ile [SEQ ID NO: 14]-Hydrocodone

Tyr-Tyr-Gly-Gly-Ile [SEQ ID NO: 14]-Hydrocodone was prepared by a similar method to Example 18 except the amino acid starting material was Boc-Tyr(tBu)-Tyr(tBu)-OSu and the conjugate starting material was Gly-Gly-Ile-Hydrocodone.

Example 27

Gly-Gly-Pro-Pro-Ile [SEQ ID NO: 15]-Hydrocodone

Synthesis of Gly-Gly-Pro-Pro-Ile [SEQ ID NO: 15]-Hydrocodone

Gly-Gly-Pro-Pro-Ile [SEQ ID NO: 15]-Hydrocodone was prepared by a similar method to Example 18 except the amino acid starting material was Boc-Gly-Gly-OSu and the conjugate starting material was Pro-Pro-Ile-Hydrocodone.

Example 28

Asp-Asp-Phe-Phe-Ile [SEQ ID NO: 16]-Hydrocodone

Synthesis of Asp-Asp-Phe-Phe-Ile [SEQ ID NO: 16]-Hydrocodone

Asp-Asp-Phe-Phe-Ile [SEQ ID NO: 16]-Hydrocodone was prepared by a similar method to Example 18 except the amino acid starting material was Boc-Asp(OtBu)-Asp(OtBu)-OSu and the conjugate starting material was Phe-Phe-Ile-Hydrocodone.

Example 29

Glu-Glu-Asp-Asp-Ile [SEQ ID NO: 17]-Hydrocodone

Synthesis of Glu-Glu-Asp-Asp-Ile [SEQ ID NO: 17]-Hydrocodone

Glu-Glu-Asp-Asp-Ile [SEQ ID NO: 17]-Hydrocodone was prepared by a similar method to Example 18 except the amino acid starting material was Boc-Glu(OtBu)-Glu(OtBu)-OSu and the conjugate starting material was Asp-Asp-Ile-Hydrocodone.

Example 30

Lys-Lys-Asp-Asp-Ile [SEQ ID NO: 18]-Hydrocodone

Synthesis of Lys-Lys-Asp-Asp-Ile [SEQ ID NO: 18]-Hydrocodone

Lys-Lys-Asp-Asp-Ile [SEQ ID NO: 18]-Hydrocodone was prepared by a similar method to Example 18 except the amino acid starting material was Boc-Lys(Boc)-Lys(Boc)-OSu and the conjugate starting material was Asp-asp-Ile-Hydrocodone.

Example 31

Tyr-Tyr-Glu-Glu-Ile [SEQ ID NO: 19]-Hydrocodone

Synthesis of Tyr-Tyr-Glu-Glu-Ile [SEQ ID NO: 19]-Hydrocodone

Tyr-Tyr-Glu-Glu-Ile [SEQ ID NO: 19]-Hydrocodone was prepared by a similar method to Example 18 except the amino acid starting material was Boc-Tyr(tBu)-Tyr(tBu)-OSu and the conjugate starting material was Glu-Glu-Ile-Hydrocodone.

Example 32

Asp-Asp-Asp-Asp-Ile [SEQ ID NO: 20]-Hydrocodone

Synthesis of Asp-Asp-Asp-Asp-Ile [SEQ ID NO: 20]-Hydrocodone

Asp-Asp-Asp-Asp-Ile [SEQ ID NO: 20]-Hydrocodone was prepared by a similar method to Example 18 except the amino acid starting material was Boc-Asp(OtBu)-Asp(OtBu)-OSu and the conjugate starting material was Asp-Asp-Ile-Hydrocodone.

Example 33

Glu-Glu-Phe-Phe-Ile [SEQ ID NO: 5]-Hydrocodone

Synthesis of Glu-Glu-Phe-Phe-Ile [SEQ ID NO: 5]-Hydrocodone

Glu-Glu-Phe-Phe-Ile [SEQ ID NO: 5]-Hydrocodone was prepared by a similar method to Example 18 except the amino acid starting material was Boc-Glu(OtBu)-Glu(OtBu)-OSu and the conjugate starting material was Phe-Phe-Ile-Hydrocodone.

Example 34

Lys-Lys-Glu-Glu-Ile [SEQ ID NO: 21]-Hydrocodone

Synthesis of Lys-Lys-Glu-Glu-Ile [SEQ ID NO: 21]-Hydrocodone

Lys-Lys-Glu-Glu-Ile [SEQ ID NO: 21]-Hydrocodone was prepared by a similar method to Example 18 except the amino acid starting material was Boc-Lys(Boc)-Lys(Boc)-OSu and the conjugate starting material was Glu-Glu-Ile-Hydrocodone.

Example 35

Tyr-Tyr-Phe-Pro-Ile [SEQ ID NO: 7]-Hydrocodone

Synthesis of Tyr-Tyr-Phe-Pro-Ile [SEQ ID NO: 7]-Hydrocodone

Tyr-Tyr-Phe-Pro-Ile [SEQ ID NO: 7]-Hydrocodone was prepared by a similar method to Example 18 except the amino acid starting material was Boc-Tyr(tBu)-Tyr(tBu)-OSu and the conjugate starting material was Phe-Pro-Ile-Hydrocodone.

YYFFI[SEQ ID NO: 4]-HC

Example 1

Tyr-Tyr-Phe-Phe-Ile[SEQ ID NO: 4]-(6-O)-Hydrocodone

Preparation of Tyr-Tyr-Phe-Phe-Ile[SEQ ID NO: 4]-(6-O)-hydrocodone

Hydrocodone bitartrate (48.38 g) was stirred in 500 ml 1N NaOH for 5 minutes. Suspension was split into 2 batches and extracted using $CHCl_3$ (2×250 ml), organics were dried using $MgSO_4$ and filtered. Solvent was removed and product was obtained as a white powder (29.05 g).

To a solution of hydrocodone freebase (7.12 g) in tetrahydrofuran (THF) (300 ml) was added $LiN(TMS)_2$ in THF (1M, 36.0 ml) via syringe. The solution was stirred at ambient temperatures for 10 minutes then Boc-Ile-OSu (11.7 g) was added. The resulting reaction mixture was stirred at ambient temperatures for 3 hours. Reaction was neutralized to pH 7 with 1M HCl and stirred for 10 minutes. Solvent was removed. Crude material was taken up in diethyl ether (100 ml), washed with sat. $NaHCO_3$ (3×100 ml), dried over $MgSO_4$, filtered, and solvent was removed. Solid was collected as a yellow powder (11.1 g).

To the Boc-Ile-Hydrocodone (11.1 g) was added 125 ml of 4N HCl in dioxane. The resulting mixture was stirred at ambient temperatures for 1 hour. Solvent was removed and final product dried under vacuum. Solid was collected as a slightly yellow powder (10.43 g).

To a suspension of Boc-Phe-Phe-OH (10.0 g) and N-hydroxysuccinimide (NHS) (3.06 g) in acetone (300 ml) was added dicyclohexylcarbodiimide (DCC) (4.99 g). The solution was stirred at ambient temperatures under argon for 18 hrs. Solid dicyclohexylurea (DCU) was filtered away and washed with acetone. Solvent was removed from filtrate. Crude material was recrystallized using a system of acetone and hexane. Solvent was filtered off and the solid was collected as a white powder (12.2 g).

To a solution of Ile-HC.2HCl (6.00 g) in N,N-dimethylformamide (DMF) (150 ml) was added 4-methyl morpholine (NMM) (6.79 ml) followed by Boc-Phe-Phe-OSu (6.93 g). The solution was stirred at ambient temperatures for 18 hours. Solvent was reduced to approximately ¼ total volume, added to sat. $NaHCO_3$ (~100 ml), and stirred for 30 minutes. The precipitate was filtered and washed thoroughly with water. Solid material was dried in vacuum, dissolved in a small amount of ethyl acetate, and filtered. Product was obtained as a slightly yellow powder (8.39 g).

To Boc-Phe-Phe-Ile-HC (2.99 g) was added 50 ml 4N HCl in dioxane. The resulting suspension was stirred at ambient temperatures for 1 hour. Solvent was removed and product was dried. Product was obtained as a yellow solid (2.60 g).

To a solution of Boc-Tyr(tBu)-OH (1.00 g) in 15 ml DMF was added O-(N-succinimidyl)-1,1,3,3-tetramethyluronium tetrafluoroborate (TSTU) (0.892 g) and NMM (0.65 ml). After 10 minutes of activation, H-Tyr(tBu)-OH (0.844 g) in 40 ml DMF:dioxane:water (2:2:1) was added. The resulting suspension was stirred at ambient temperature for 4 hours. After this time, water (15 ml) was added and the resulting solution was stirred at ambient temperature for 30 minutes. The solvent volume was reduced to ¼ and extracted with ethyl acetate (250 ml), washed with 5% acetic acid in water (2×150 ml), water (3×150 ml), and brine (150 ml). The organic layer was dried over $MgSO_4$, filtered, and solvent removed. Crude product was purified using recrystallization with IPAC/hexane solvent system. Final product was isolated as a white solid (1.025 g).

To a suspension of Boc-Tyr(tBu)-Tyr(OtBu)-OH (7.32 g) and NHS (1.54 g) in acetone (150 ml) was added DCC (2.51 g). The solution was stirred at ambient temperatures under argon for 18 hrs. Solid DCU was filtered away and washed with acetone. Solvent was removed from filtrate. Crude material was washed with warm hexane. Solid was collected as a white powder (6.65 g).

To a solution of Phe-Phe-Ile-HC.2HCl (2.63 g) in DMF (100 ml) was added NMM (3.70 ml) followed by Boc-Tyr(tBu)-Tyr(tBu)-OSu (4.41 g). The solution was stirred at ambient temperatures for 18 hours. Solvent was reduced to approximately ¼ total volume, added to sat. $NaHCO_3$ (~100 ml), and stirred for 30 minutes. The precipitate was filtered and washed thoroughly with water. Solid material was dried in vacuum and purified by reverse phase HPLC (2.77 g). Product was deprotected using 4N HCl in dioxane (~50 ml).

To a solution of Phe-Phe-Ile-HC.2HCl (5.00 g) in DMF (250 ml) was added NMM (3.52 ml) followed by Boc-Tyr(tBu)-Tyr(tBu)-OSu (4.61 g). The solution was stirred at ambient temperatures for 6 hours. Solvent was reduced to approximately ¼ total volume, added to sat. $NaHCO_3$ (~500 ml), and stirred for 30 minutes. The precipitate was filtered and washed thoroughly with water. Solid material was dried in vacuum overnight, dissolved in methanol, and any remaining solid material was filtered. The solvent was evaporated from the filtrate and the product was recrystallized using ethanol (~60 ml). The precipitate was filtered and dried in vacuum overnight. Product was collected as a pale brown powder (4.57 g).

Boc-Tyr(OtBu)-Tyr(OtBu)-Phe-Phe-Ile-HC (3.53 g) was deprotected using 4N HCl in dioxane (~100 ml). This material was stirred at ambient temperatures for ~1 hour. The solvent was evaporated and the product was collected as a slightly yellow powder (3.64 g).

FIGS. 9 through 34 demonstrate plasma levels measured by ELISA of various compounds described in Examples 35 through 68.

Glycopeptides

Figure 35:
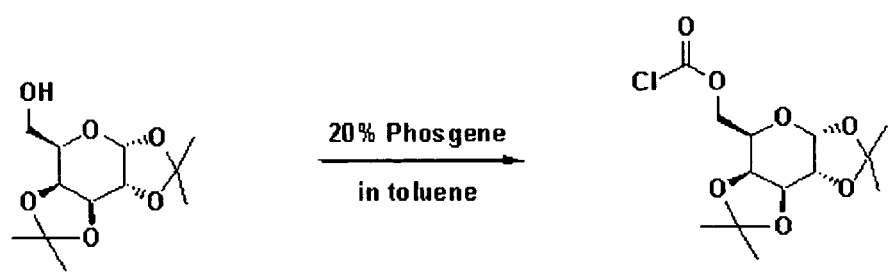
FIG. 35. illustrates preparation of 1,2:3,4-di-O-isopropylidene-D-galactopyranose.

FIG. 35 illustrates preparation of 1,2:3,4-di-O-isopropylidene-D-galactopyranose.

| Reagents | MW | Weight | mmoles | Molar Equivalents |
|---|---|---|---|---|
| 1,2:3,4-di-O-isopropylidene-D-galactopyranose | 260 | 1.00 g | 3.85 | 1 |
| 20% Phosgene in toluene | — | 20 ml | — | — |

Chloroformate of 1,2:3,4-di-O-isopropylidene-D-galactopyranose

To a stirring solution of 20% phosgene in toluene under an inert atmosphere was added 1,2:3,4-di-O-isopropylidene-D-galactopyranose via syringe. The resulting clear, colorless solution was stirred at ambient temperature for 30 minutes. After stirring, Ar(g) was bubbled through the solution for approximately 20 minutes to remove any excess phosgene.

Solvent was then removed and product dried under vacuum for 18 hours. Product was used without further purification or characterization.

Example 37

Galactose-CO-Leu-Hydrocodone

Synthesis of Galactose-CO-Leu-Hydrocodone

To the chloroformate of galactose (1.5 eq) in dimethylformamide (DMF) (2 ml/mmol) was added Leu-Hydrocodone (1 eq) and 4-methylmorpholine (NMM) (6 eq). The reaction was stirred at ambient temperatures for 18 hours. Reaction was quenched by the addition of water, solvents were removed and crude product was isolated by purification with reverse-phase HPLC.

Product was deprotected using 1:1 1M HCl:THF (1 ml/0.1 mmol) in 3 hours. Product was re-purified by reverse-phase HPLC.

Example 38

Galactose-CO-Pro-Pro-Ile-Hydrocodone

Synthesis of Galactose-CO-Pro-Pro-Ile-Hydrocodone

Galactose-CO-Pro-Pro-Ile-Hydrocodone was prepared in a manner similar to Example 37 except $Pro_2$-Ile-Hydrocodone was used as the conjugated starting material.

Example 39

Galactose-CO-Pro-Pro-Leu-Hydrocodone

Synthesis of Galactose-CO-Pro-Pro-Leu-Hydrocodone

Galactose-CO-Pro-Pro-Leu-Hydrocodone was prepared in a manner similar to Example 37 except $Pro_2$-Leu-Hydrocodone was used as the conjugated starting material.

Figure 36:
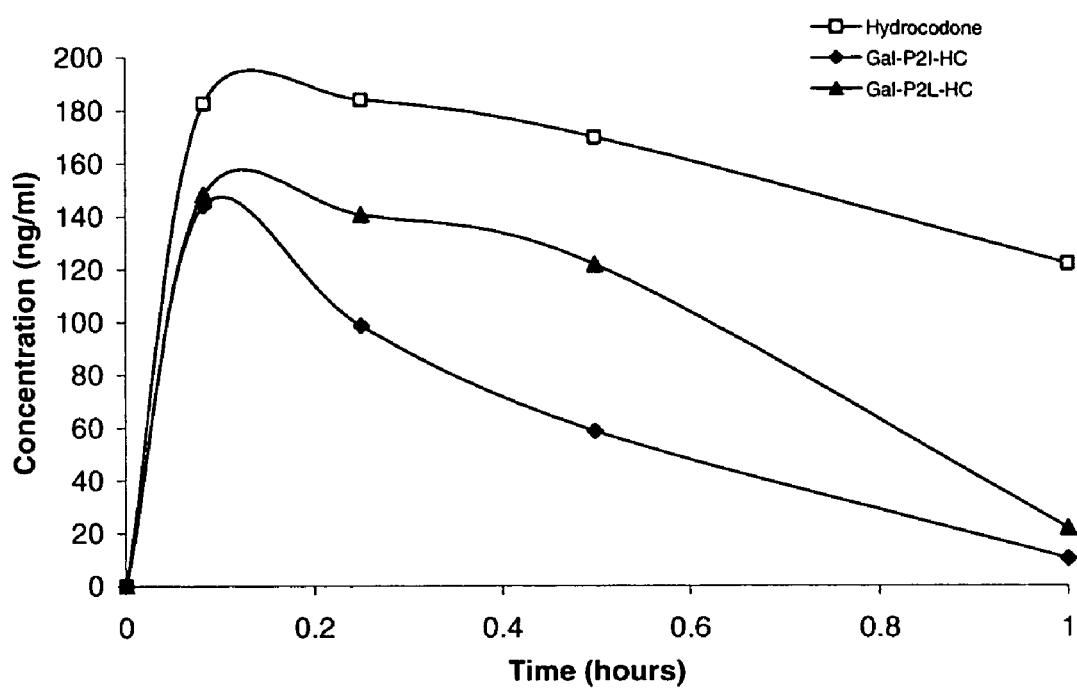
FIG. 36. Oral bioavailability of abuse-resistant hydrocodone glyco-peptide conjugates, measured as free hydrocodone.

FIG. 36 illustrates oral bioavailability of abuse-resistant hydrocodone glycopeptide conjugates, measured as free hydrocodone.

Example 40

Gulonic acid-Ile-Hydrocodone

Synthesis of Gulonic acid-Ile-Hydrocodone

Gulonic acid-Ile-Hydrocodone was prepared in a manner similar to Example 37 except Ile-Hydrocodone was used as the conjugated starting material and Gulonic acid-OSu was used as the carbohydrate starting material.

Figure 37:
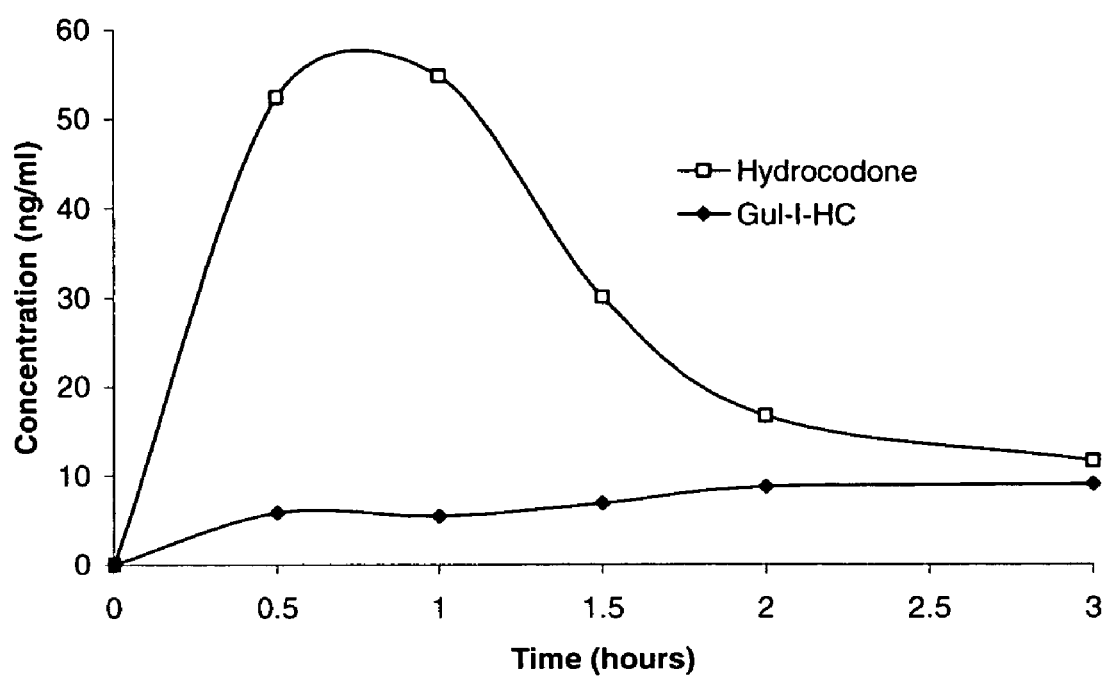
FIG. 37. Oral bioavailability of an abuse-resistant hydrocodone amino acid-carbohydrate conjugate, measured as free hydrocodone.

FIG. 37 illustrates Oral bioavailability of an abuse-resistant hydrocodone amino acid-carbohydrate conjugate, measured as free hydrocodone.

D-amino Acids

Example 41

(d)-Lys-(l)-Lys-Ile-Hydrocodone

Preparation of (d)-Lys-(l)-Lys-Ile-Hydrocodone

To a solution of Ile-Hydrocodone in DMF was added NMM followed by Boc-(d)-Lys(Boc)-(l)-Lys(Boc)-OSu. The solution was stirred at ambient temperatures for 18 hours. Solvent was removed. Crude material was purified using preparative HPLC (Phenomenex Luna C18, 30×250 mm, 5 µM, 100 Å; Gradient: 90 water/10 0.1% TFA-MeCN→0/100; 30 ml/min.). Solid was collected as a slightly yellow powder. To the Boc-(d)-Lys(Boc)-(l)-Lys (Boc)-Hydrocodone was added 4N HCl in dioxane. The resulting mixture was stirred at ambient temperatures for 18 hours. Solvent was removed and final product dried under vacuum. Solid was collected as a slightly yellow solid.

Nucleosides

Figure 38:
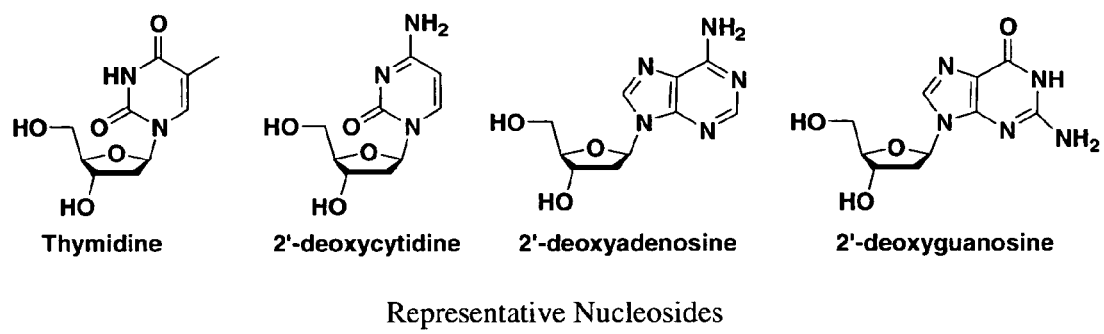
FIG. 38 illustrates nucleosides and conjugation sites.
Figure 38:
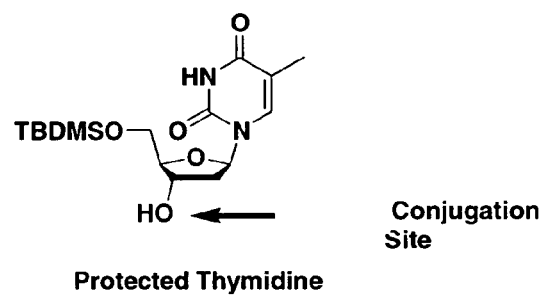
Figure 39:
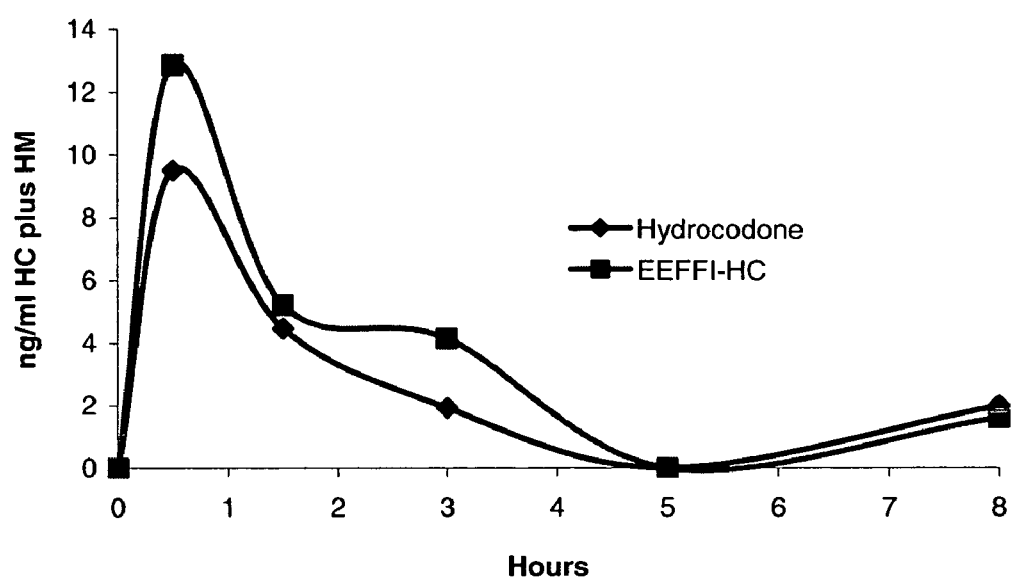
FIG. 39. Oral bioavailability in rats for hydrocodone vs. EEFFFI[SEQ ID NO: 2]-HC at a dose (1 mg/kg) approximating a therapeutic human dose equivalent measured as free hydrocodone.
Figure 40:
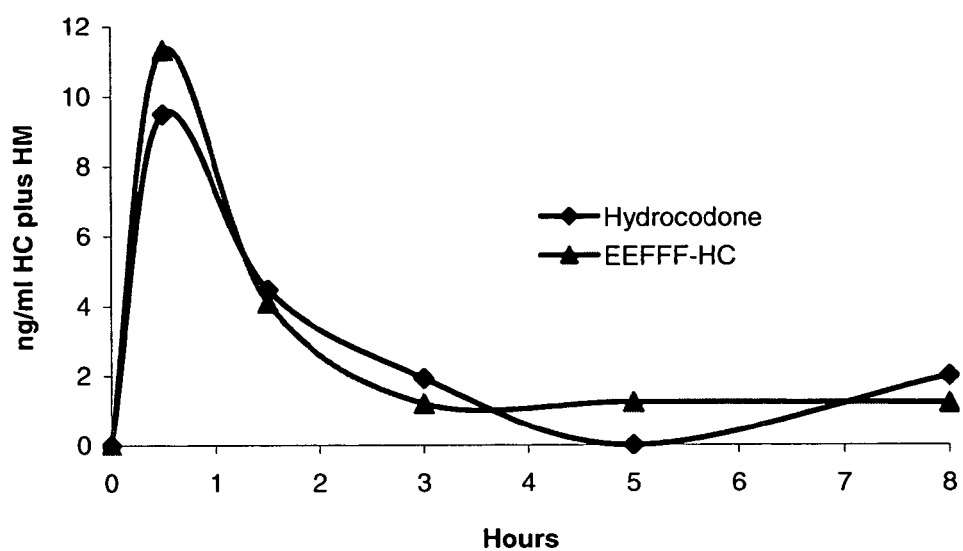
FIG. 40. Oral bioavailability in rats for hydrocodone vs. EEFFF[SEQ ID NO: 3]-HC at a dose (1 mg/kg) approximating a therapeutic human dose equivalent measured as free hydrocodone.
Figure 41:
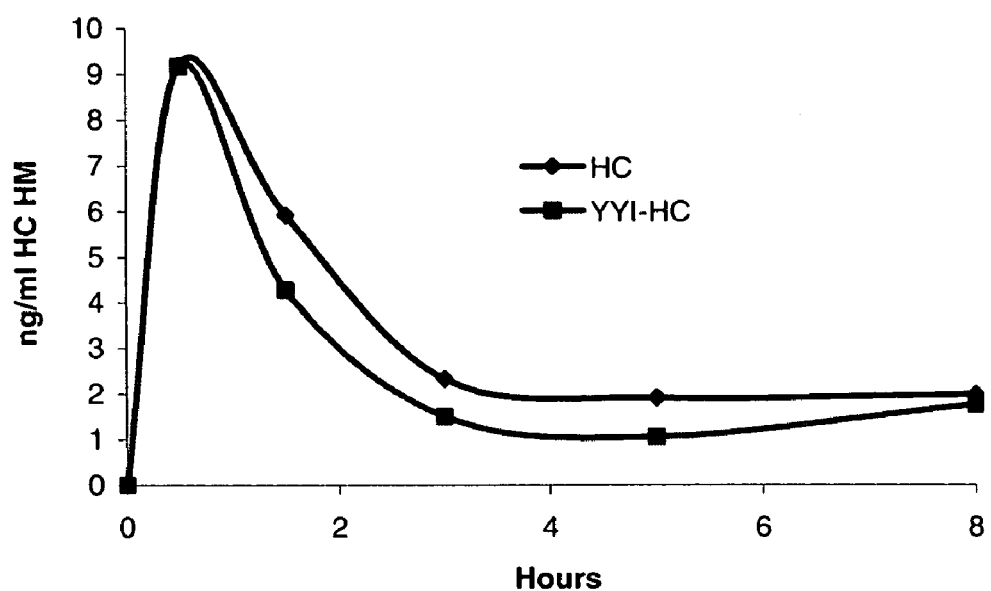
FIG. 41. Oral bioavailability in rats for hydrocodone vs. YYI-HC at a dose (1 mg/kg) approximating a therapeutic human dose equivalent measured as free hydrocodone.
Figure 42:
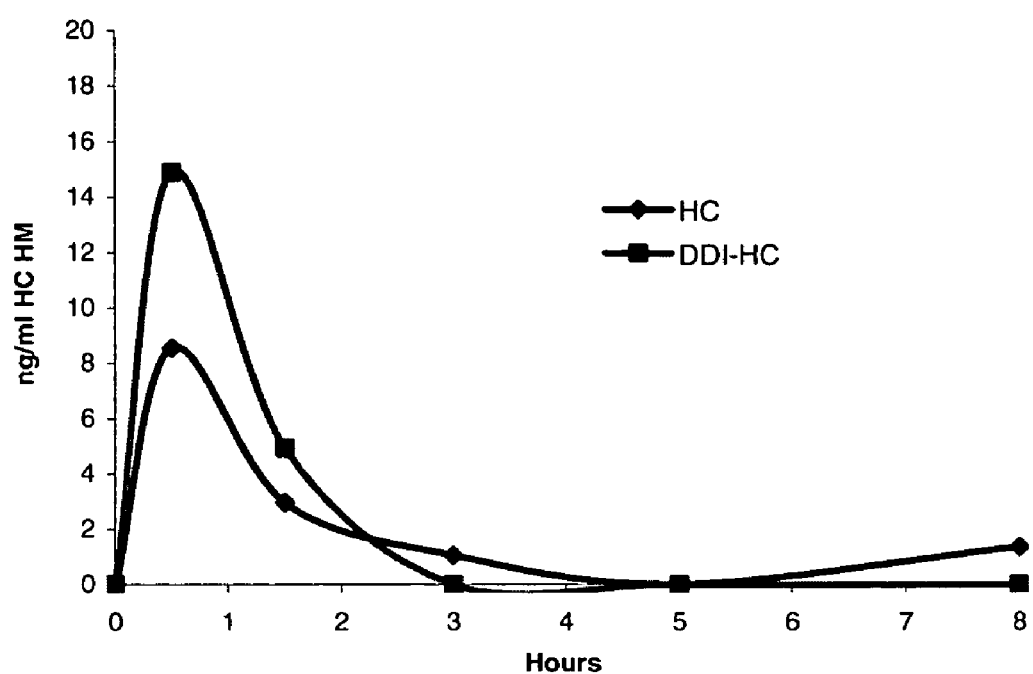
FIG. 42. Oral bioavailability in rats for hydrocodone vs. DDI-HC at a dose (1 mg/kg) approximating a therapeutic human dose equivalent measured as free hydrocodone.
Figure 43:
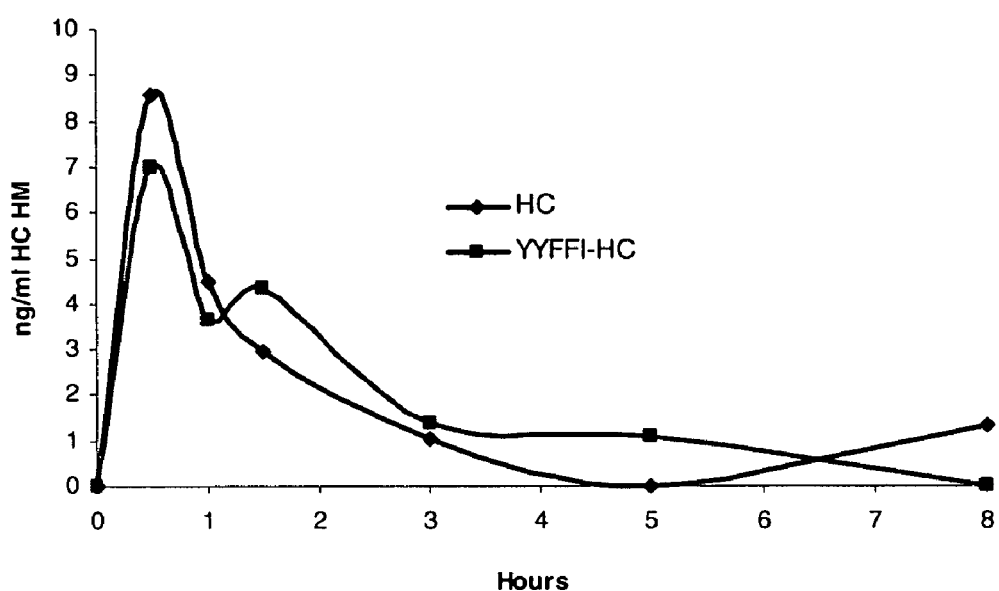
FIG. 43. Oral bioavailability in rats for hydrocodone vs. YYFFI[SEQ ID NO: 4]-HC at a dose (1 mg/kg) approximating a therapeutic human dose equivalent measured as free hydrocodone.
Figure 44:
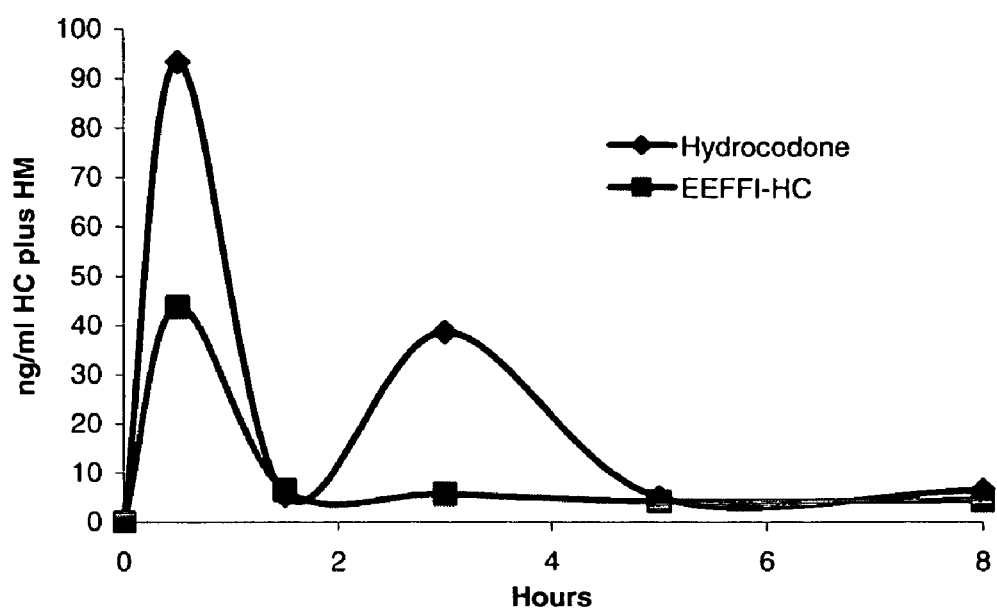
FIG. 44. Oral bioavailability in rats for hydrocodone vs. EEFFI[SEQ ID NO: 5]-HC at a dose (5 mg/kg) approaching a human overdose equivalent measured as free hydrocodone.
Figure 45:
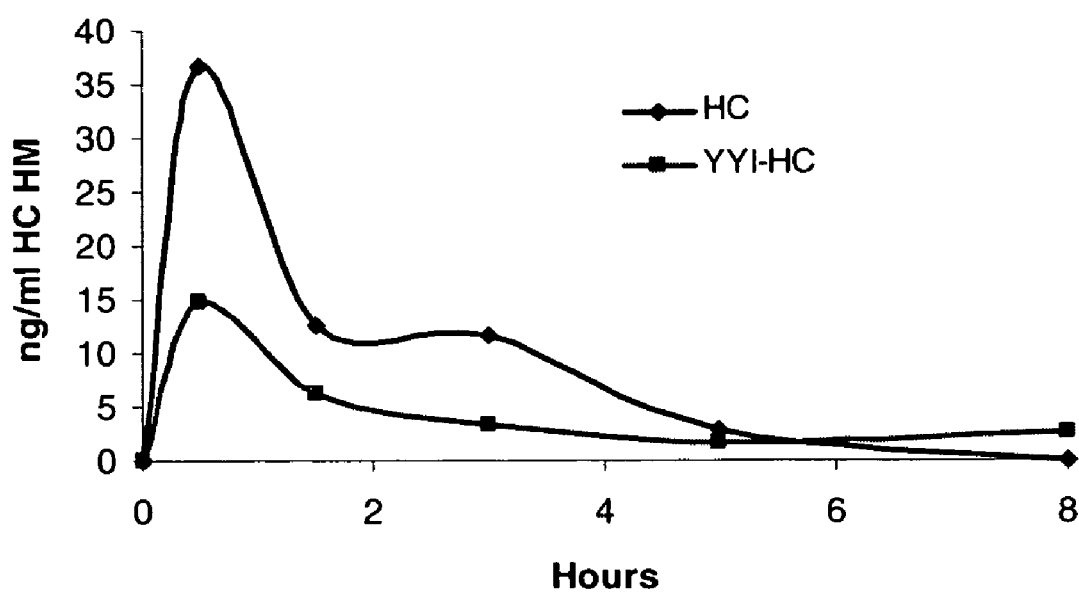
FIG. 45. Oral bioavailability in rats for hydrocodone vs. YYI-HC at a dose (5 mg/kg) approaching a human overdose equivalent measured as free hydrocodone.
Figure 46:
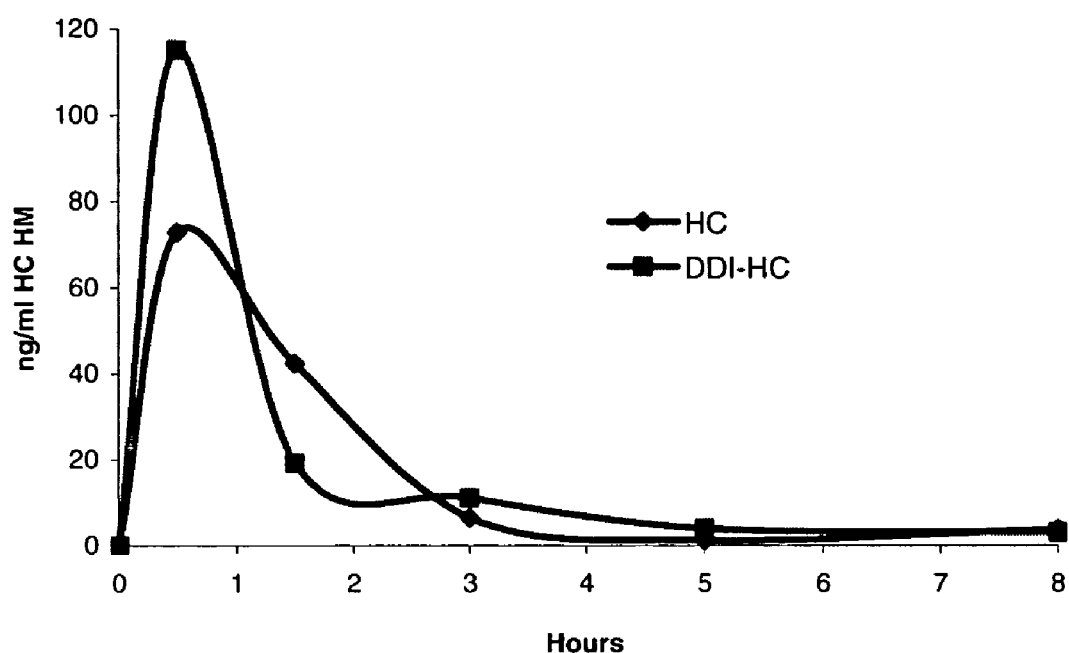
FIG. 46. Oral bioavailability in rats for hydrocodone vs. DDI-HC at a dose (5 mg/kg) approaching a human overdose equivalent measured as free hydrocodone.
Figure 47:
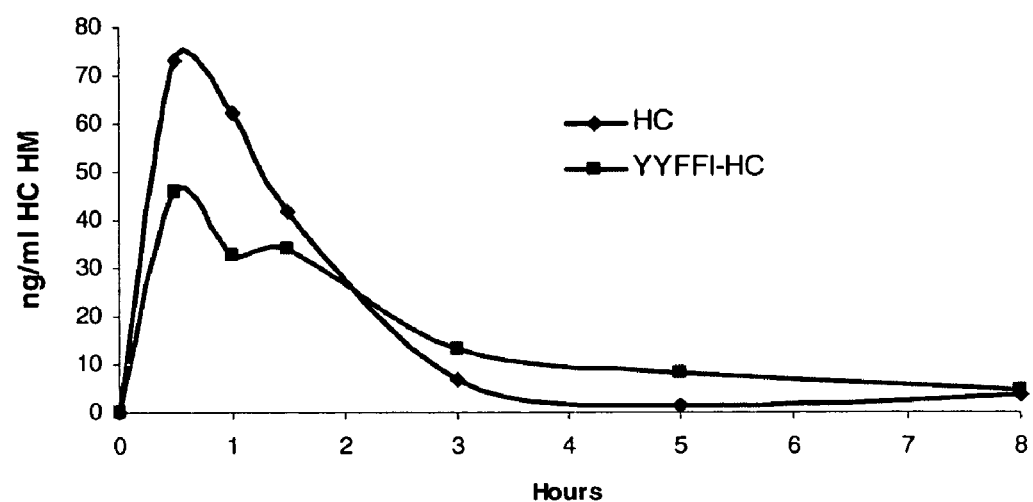
FIG. 47. Oral bioavailability in rats for hydrocodone vs. YYFFI[SEQ ID NO: 4]-HC at a dose (5 mg/kg) approaching a human overdose equivalent measured as free hydrocodone.
Figure 48:
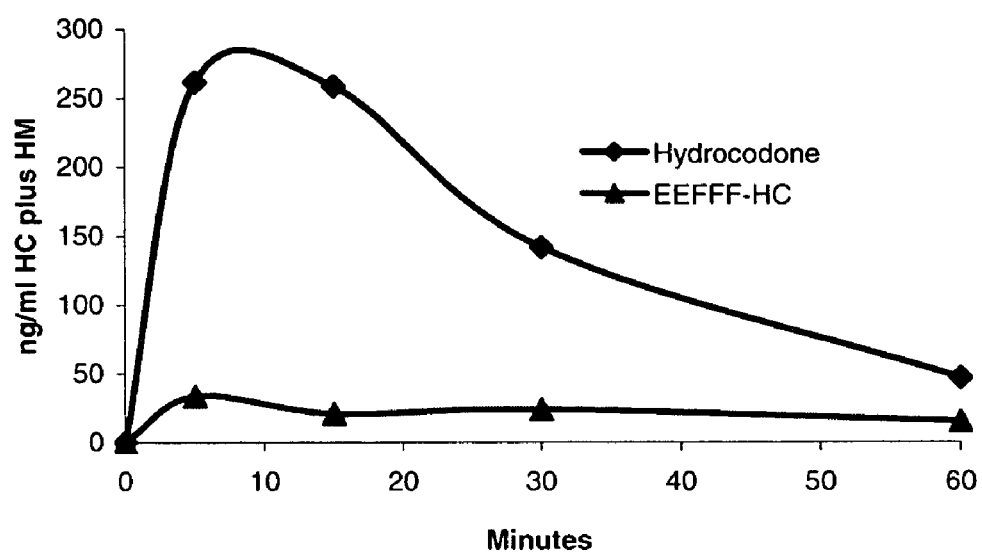
FIG. 48. Decrease in bioavailability of EEFFF[SEQ ID NO: 3]-HC as compared to hydrocodone by the intranasal route of administration measured as free hydrocodone.
Figure 49:
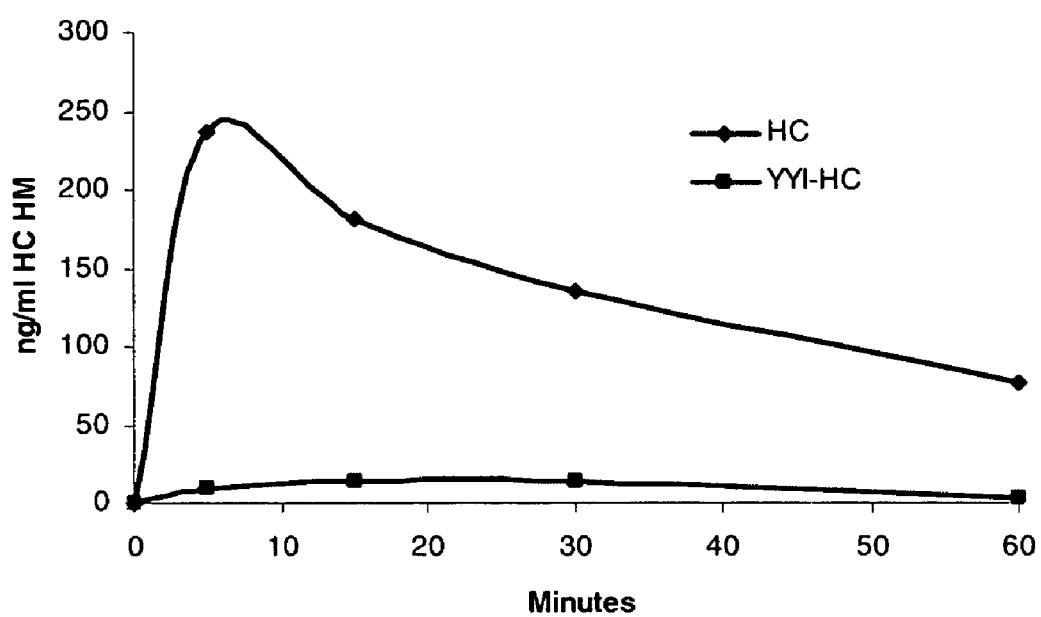
FIG. 49. Decrease in bioavailability of YYI-HC as compared to hydrocodone by the intranasal route of administration measured as free hydrocodone.
Figure 50:
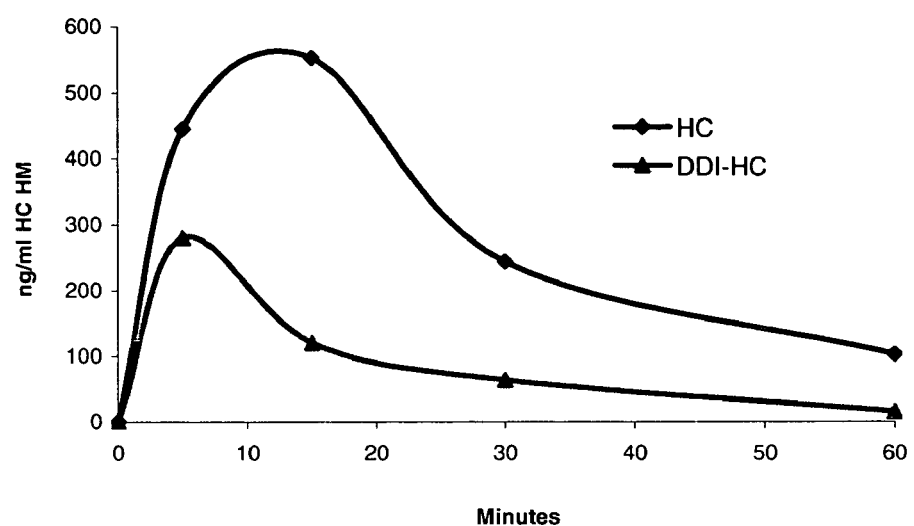
FIG. 50. Decrease in bioavailability of DDI-HC as compared to hydrocodone by the intranasal route of administration measured as free hydrocodone.
Figure 51:
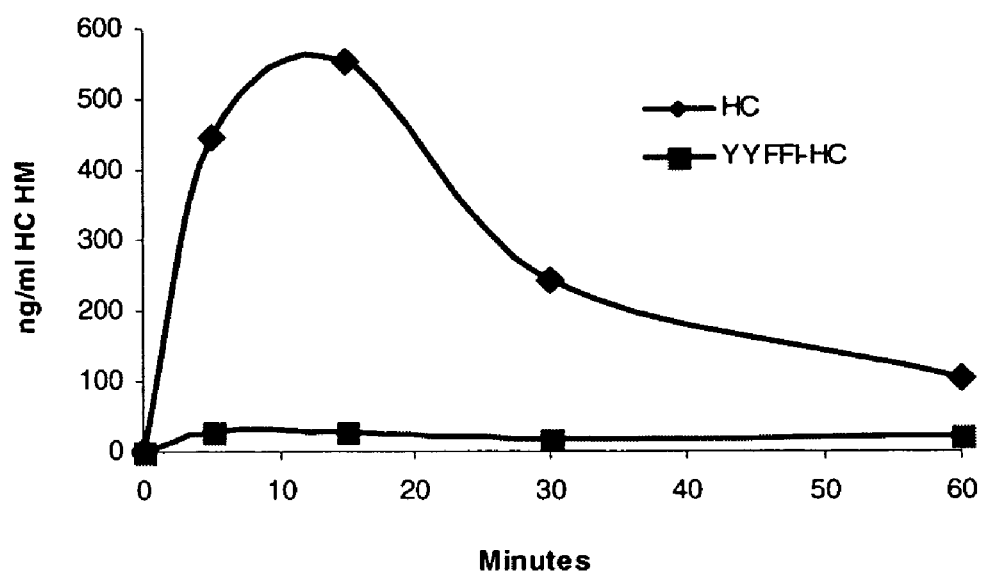
FIG. 51. Decrease in bioavailability of YYFFI[SEQ ID NO: 4]-HC as compared to hydrocodone by the intranasal route of administration measured as free hydrocodone.
Figure 52:
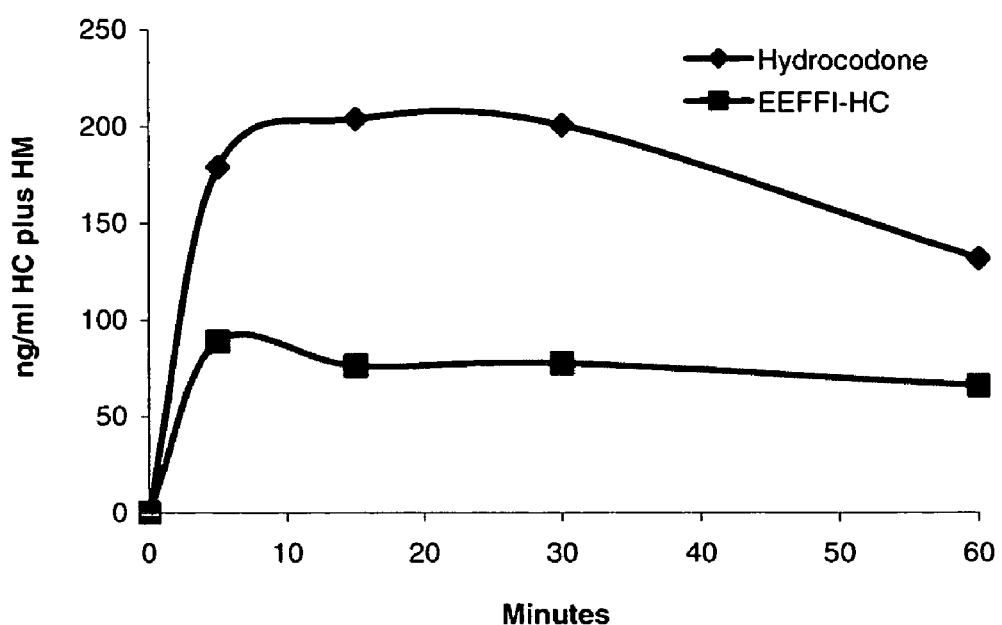
FIG. 52. Decrease in bioavailability of EEFFI[SEQ ID NO: 5]-HC as compared to hydrocodone by the intravenous route of administration measured as free hydrocodone.
Figure 53:
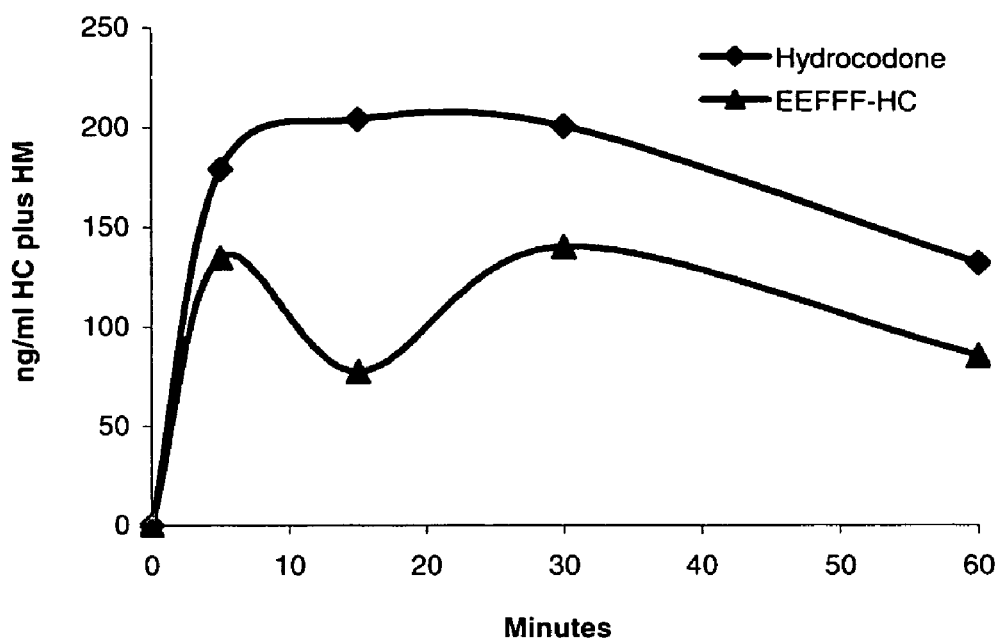
FIG. 53. Decrease in bioavailability of EEFFF[SEQ ID NO: 3]-HC as compared to hydrocodone by the intravenous route of administration measured as free hydrocodone.
Figure 54:
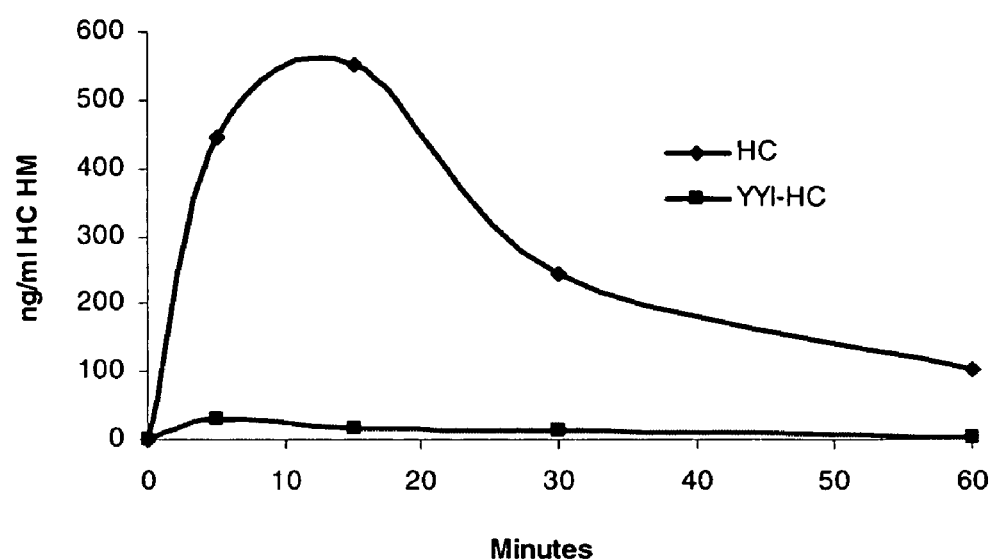
FIG. 54. Decrease in bioavailability of YYI-HC as compared to hydrocodone by the intravenous route of administration measured as free hydrocodone.
Figure 55:
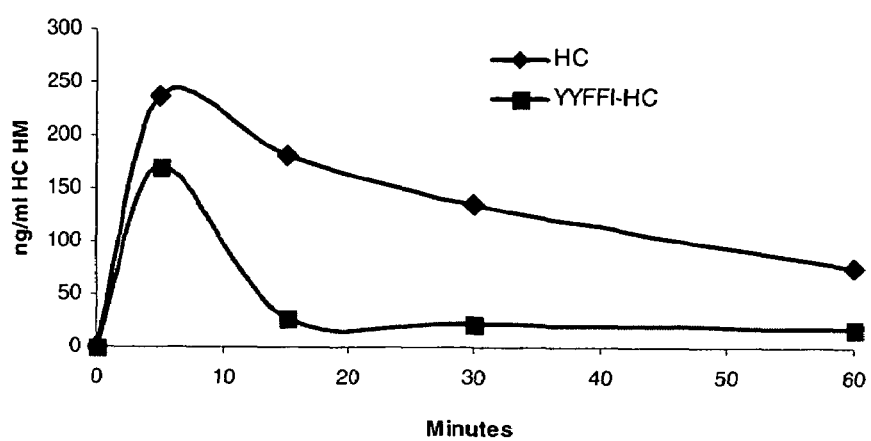
FIG. 55. Decrease in bioavailability of YYFFI[SEQ ID NO: 4]-HC as compared to hydrocodone by the intravenous route of administration measured as free hydrocodone.
Figure 56:
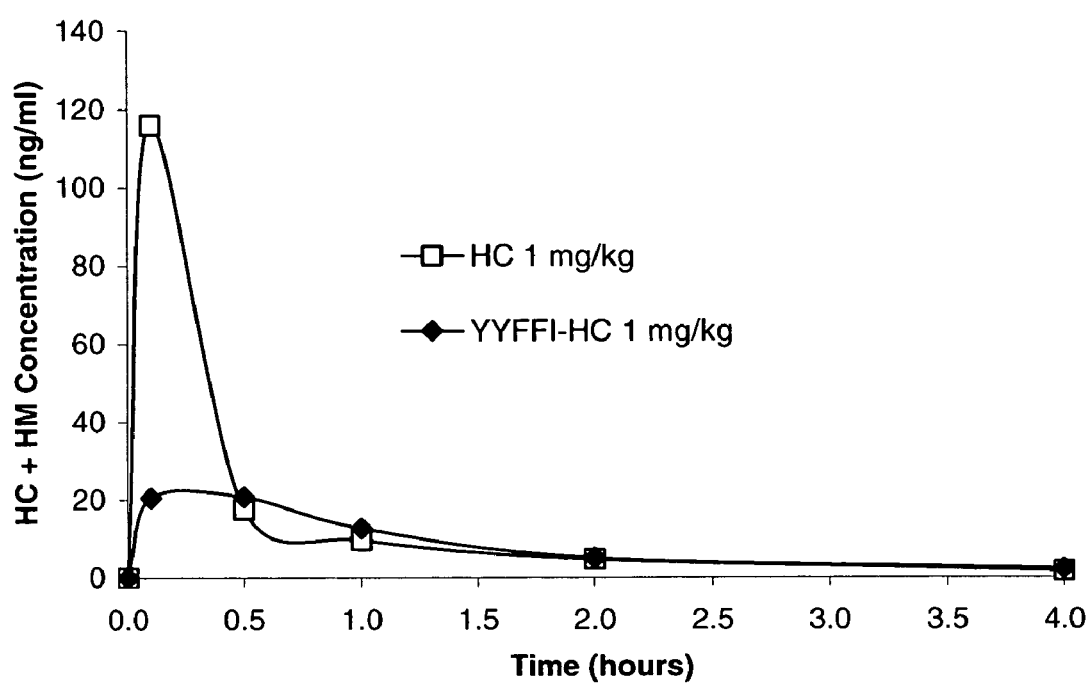
FIG. 56. Oral bioavailability of hydrocodone plus hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 57:
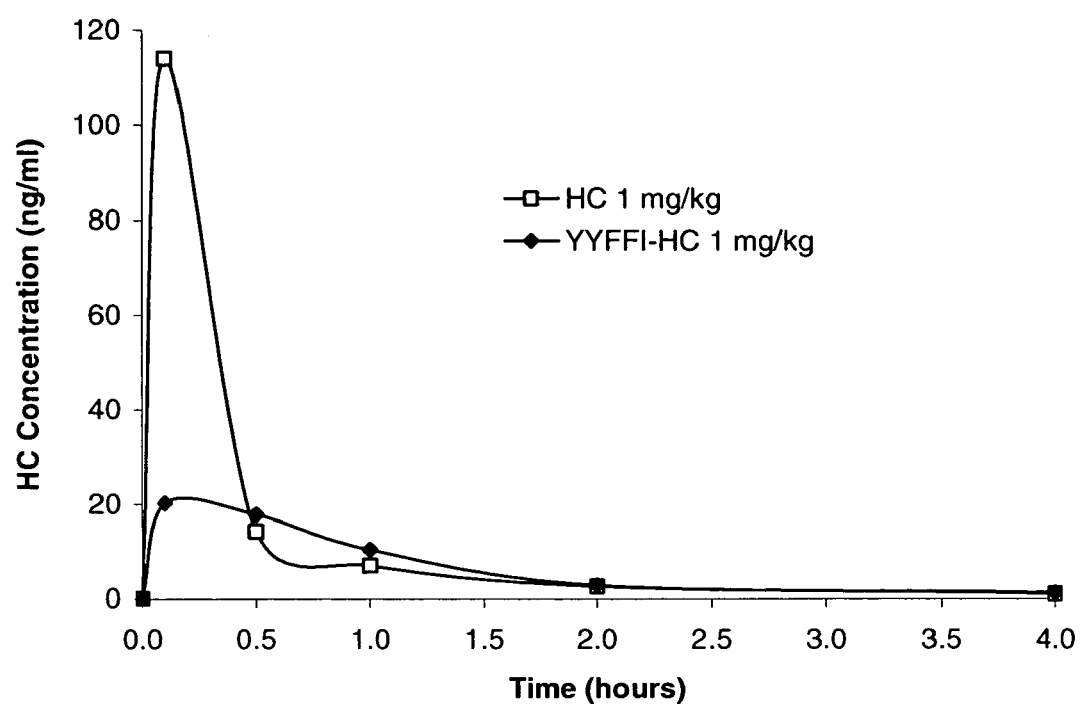
FIG. 57. Oral bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 58:
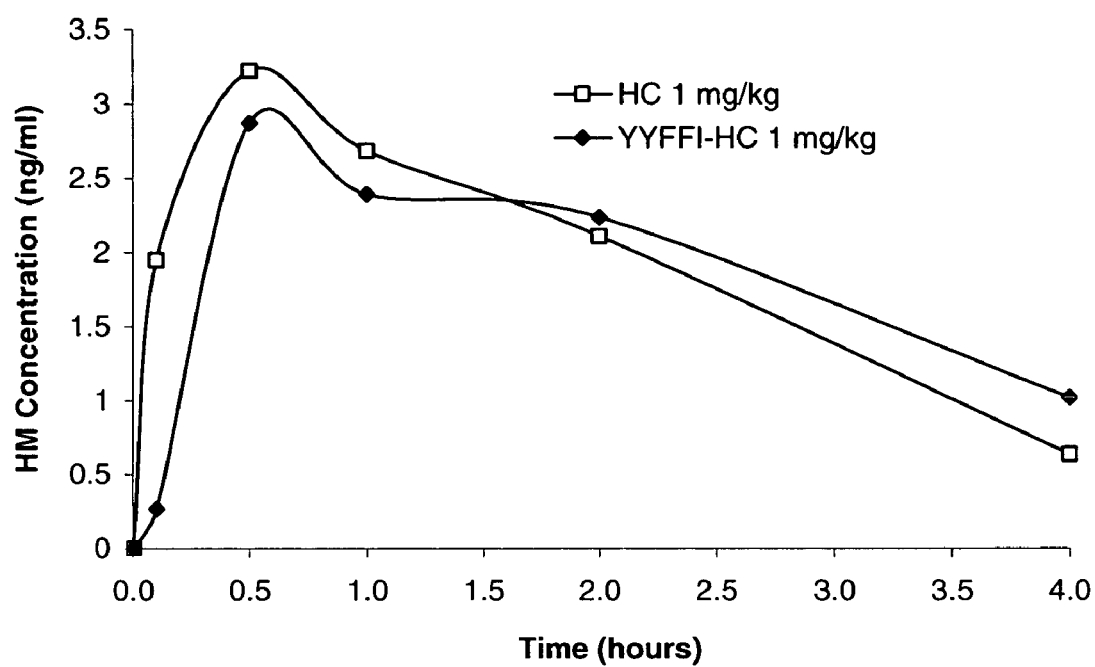
FIG. 58. Oral bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 59:
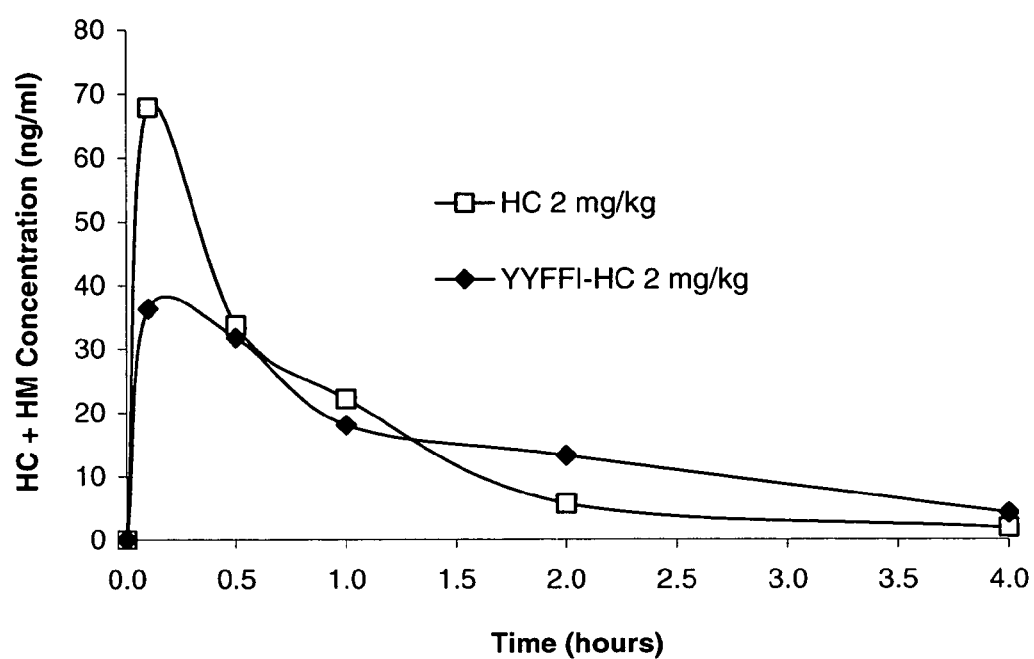
FIG. 59. Oral bioavailability of hydrocodone plus hydromorphone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 60:
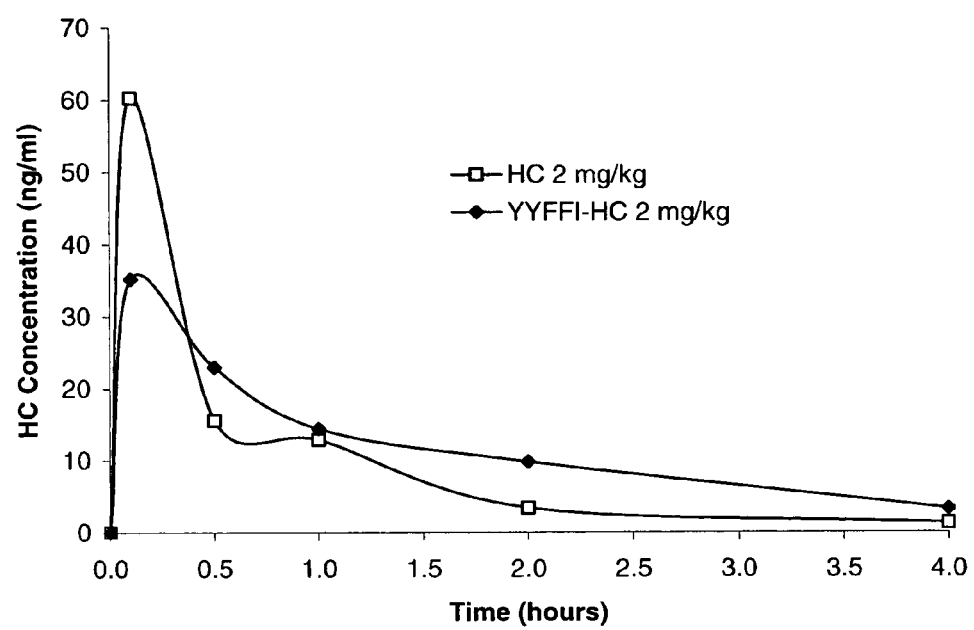
FIG. 60. Oral bioavailability of hydrocodone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 61:
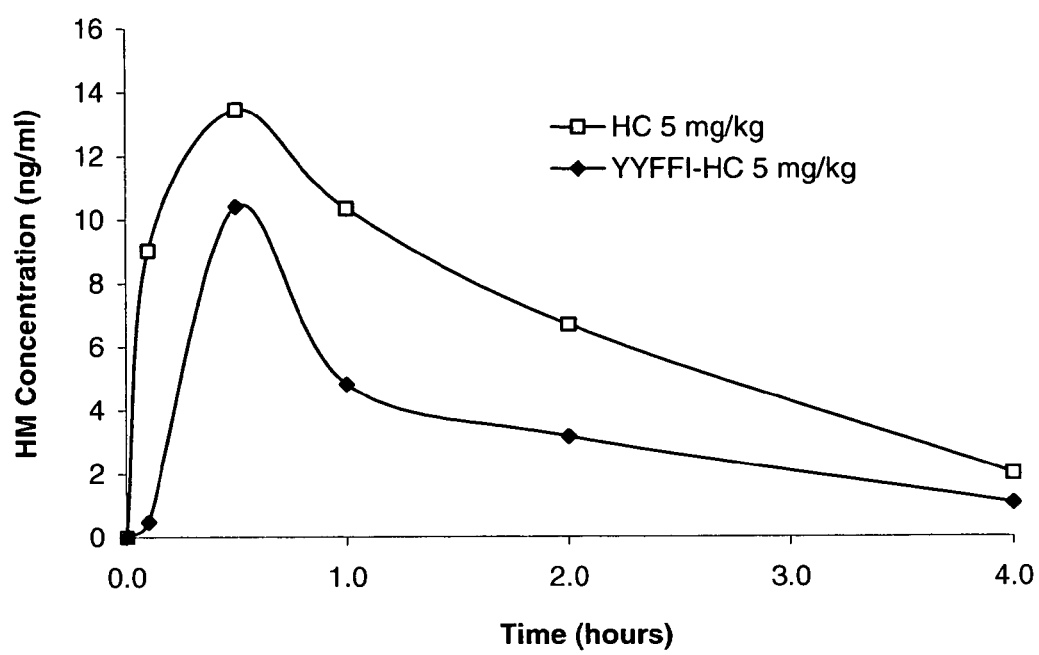
FIG. 61. Oral bioavailability of hydromorphone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 62:
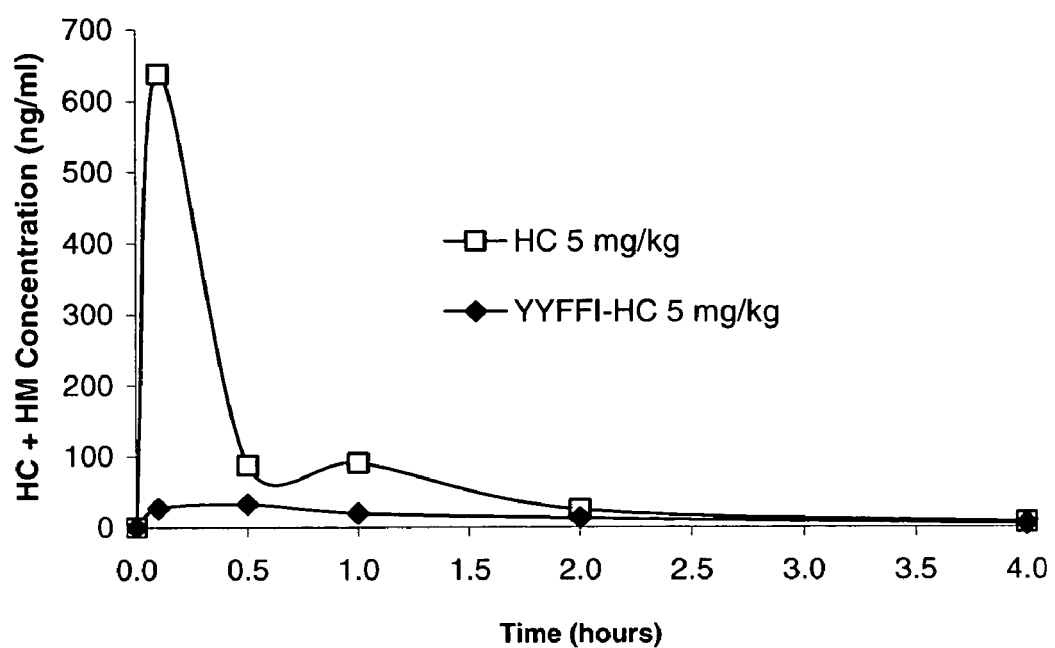
FIG. 62. Oral bioavailability of hydrocodone plus hydromorphone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 63:
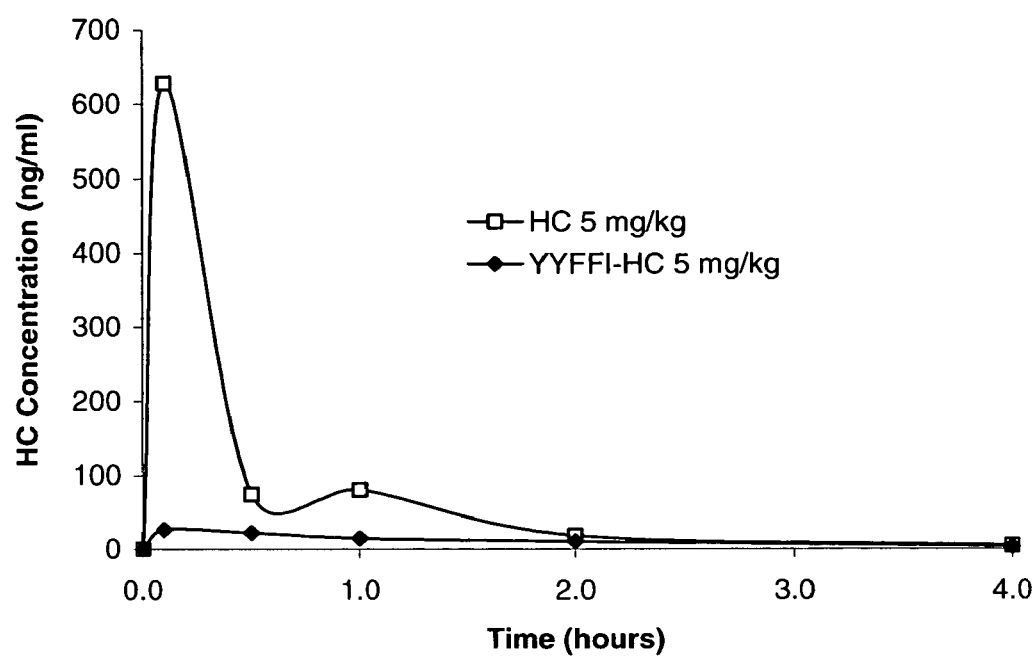
FIG. 63. Oral bioavailability of hydrocodone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 64:
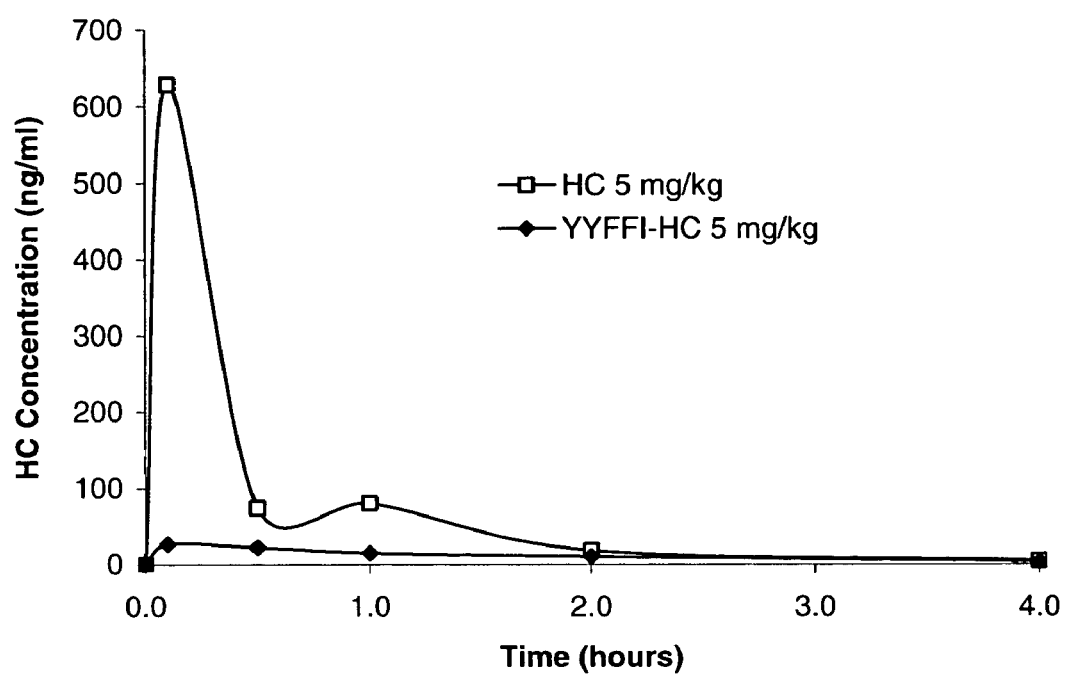
FIG. 64. Oral bioavailability of hydromorphone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 65:
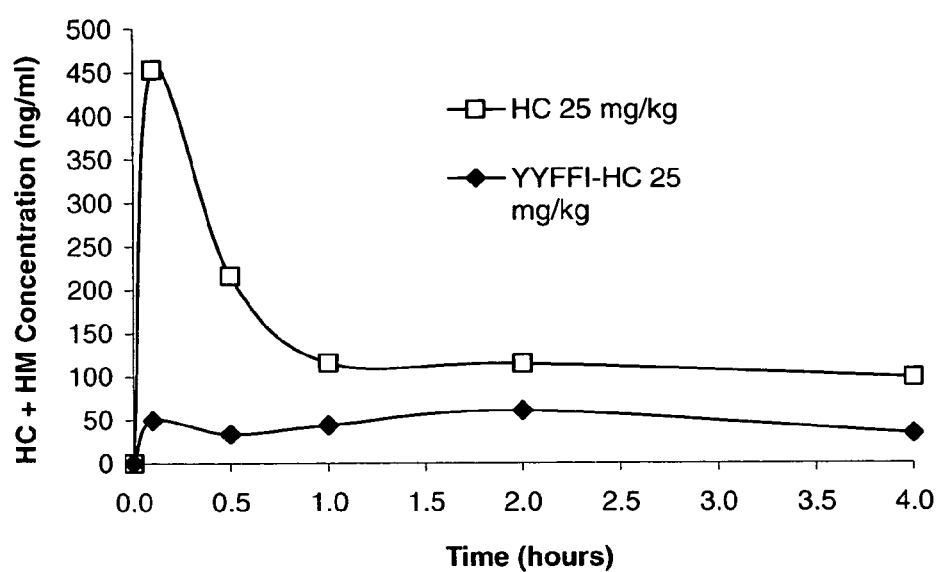
FIG. 65. Oral bioavailability of hydrocodone plus hydromorphone (concentration vs. time) following administration of hydrocodone bitratrate or YYFFI[SEQ ID NO: 4]-HC at 25 mg/kg (equimolar doses with equivalent content of hydrocodone base) in rats, measured as free hydrocodone.
Figure 66:
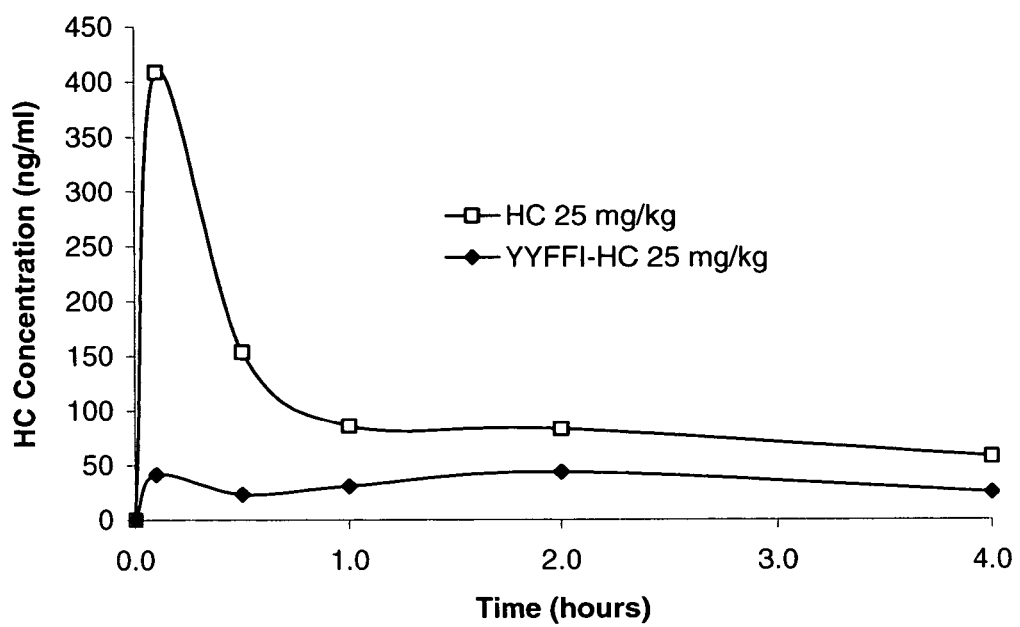
FIG. 66. Oral bioavailability of hydrocodone (concentration vs. time) following administration of hydrocodone bitratrate or YYFFI[SEQ ID NO: 4]-HC at 25 mg/kg (equimolar doses with equivalent content of hydrocodone base) in rats, measured as free hydrocodone.
Figure 67:
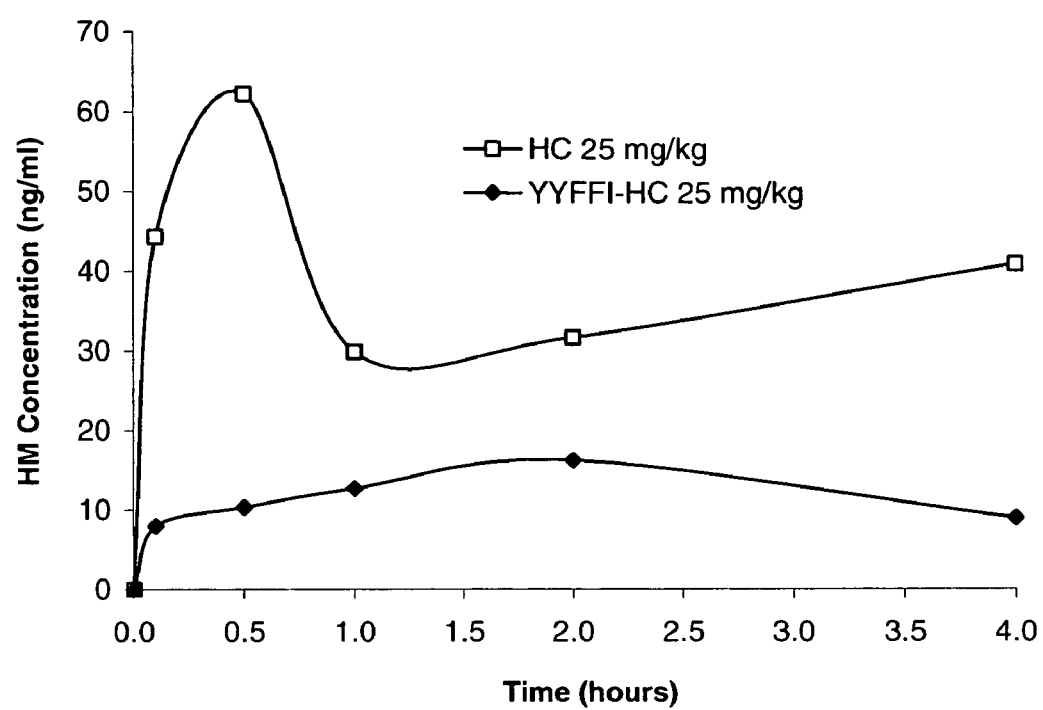
FIG. 67. Oral bioavailability of hydromorphone (concentration vs. time) following administration of hydrocodone bitratrate or YYFFI[SEQ ID NO: 4]-HC at 25 mg/kg (equimolar doses with equivalent content of hydrocodone base) in rats, measured as free hydrocodone.
Figure 68:
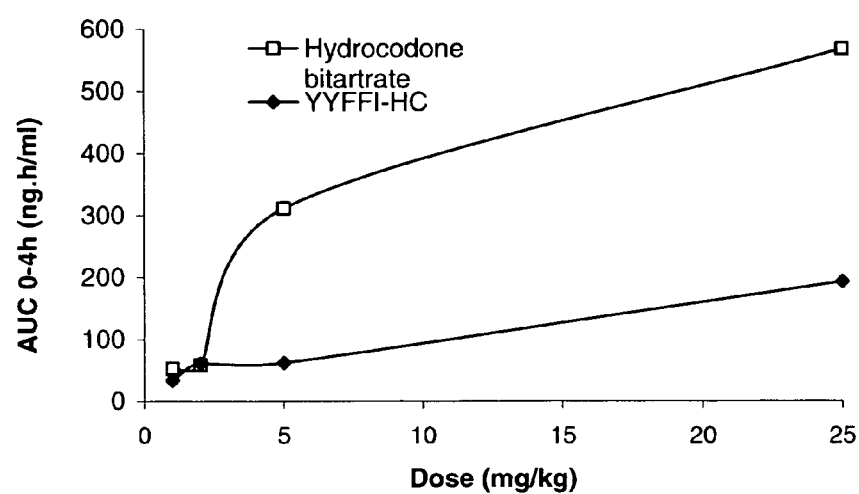
FIG. 68. Oral bioavailability ($AUC_{0-4h}$) of hydrocodone plus hydromorphone (concentration vs. dose) in proportion to dose following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 69:
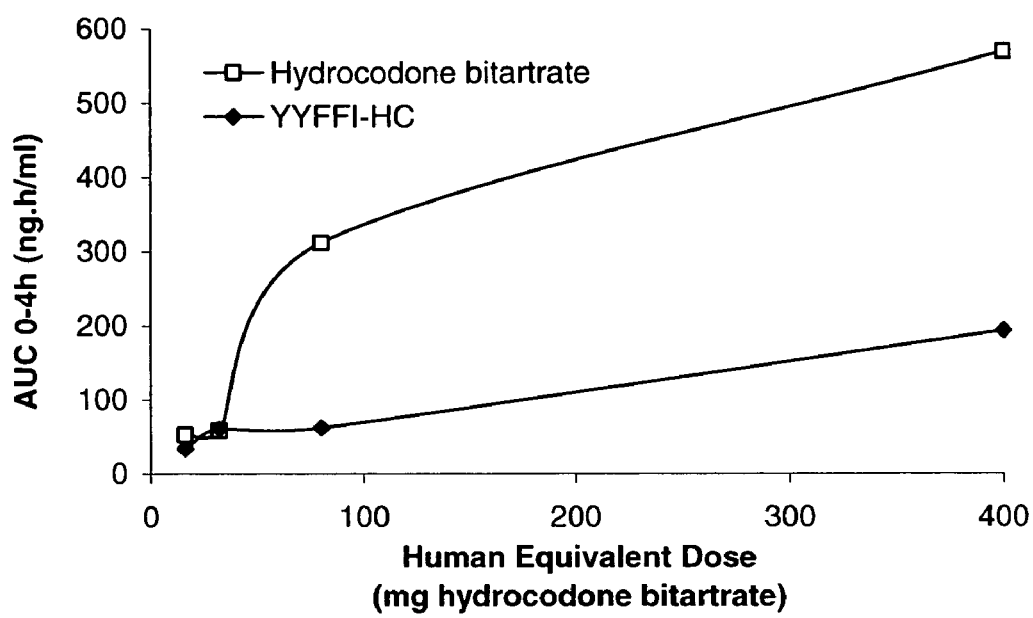
FIG. 69. Oral bioavailability ($AUC_{0-4h}$) of hydrocodone plus hydromorphone in proportion to human equivalent doses (HED) following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 70:
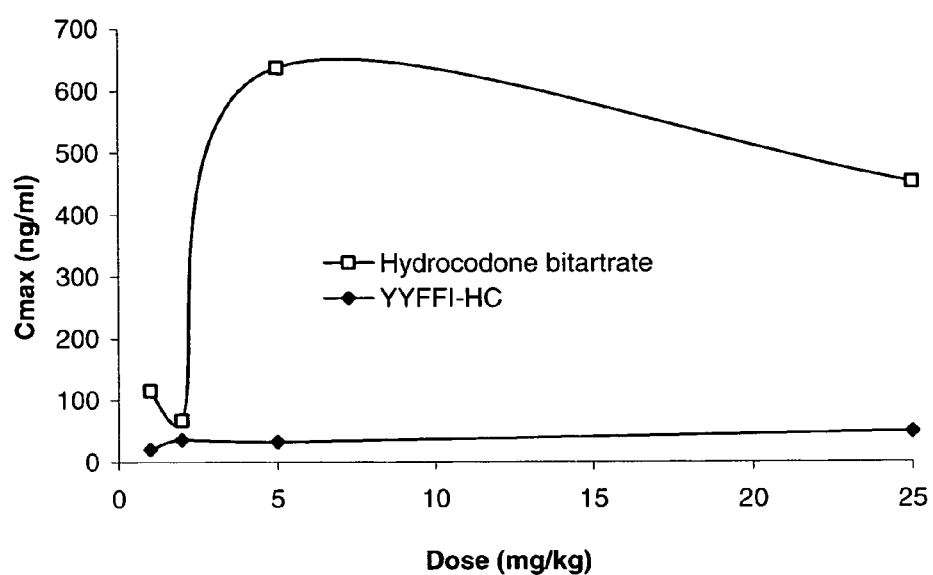
FIG. 70. Oral bioavailability ($C_{max}$) of hydrocodone plus hydromorphone (concentration vs. dose) in proportion to dose following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 71:
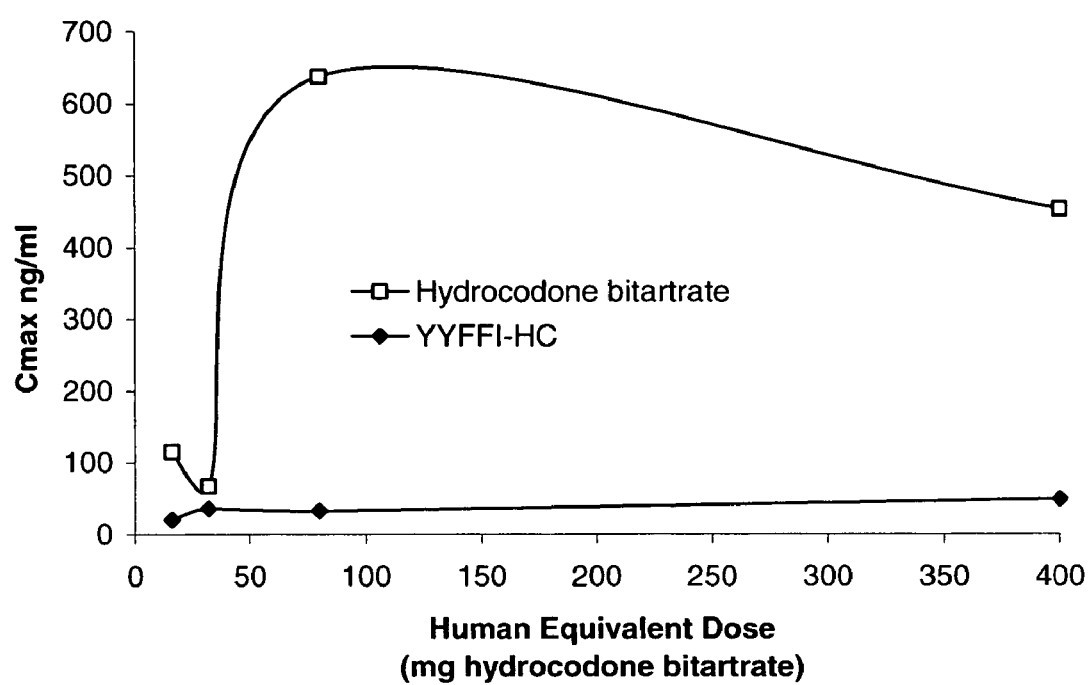
FIG. 71. Oral bioavailability ($C_{max}$) of hydrocodone plus hydromorphone in proportion to human equivalent doses (HED) following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 72:
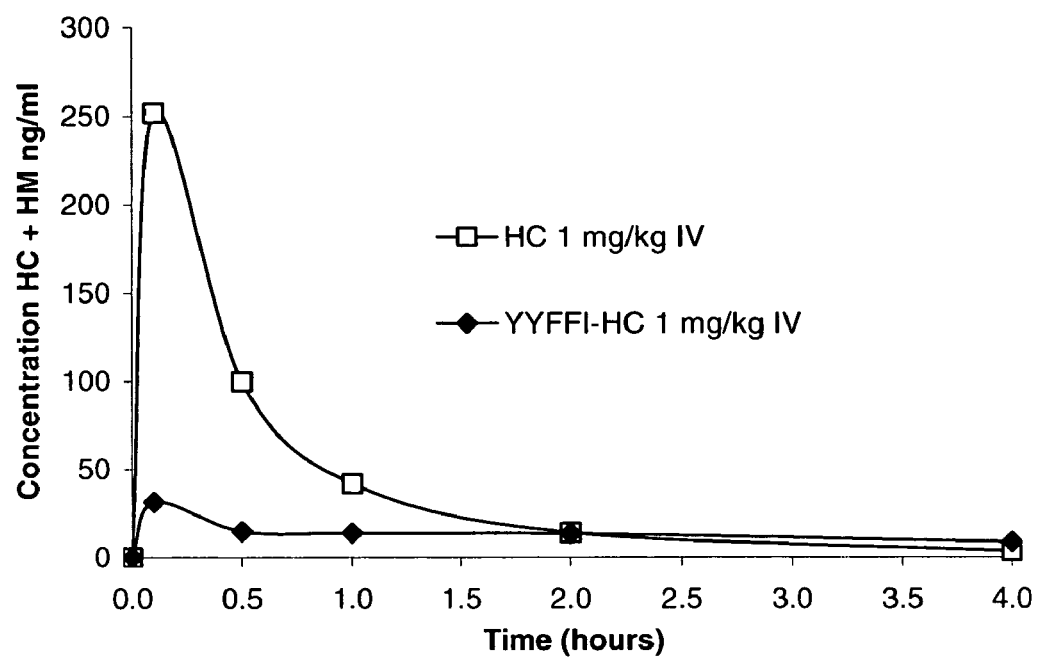
FIG. 72. Intravenous bioavailability of hydrocodone plus hydromorphone and YYFFI[SEQ ID NO: 4]-HC (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 73:
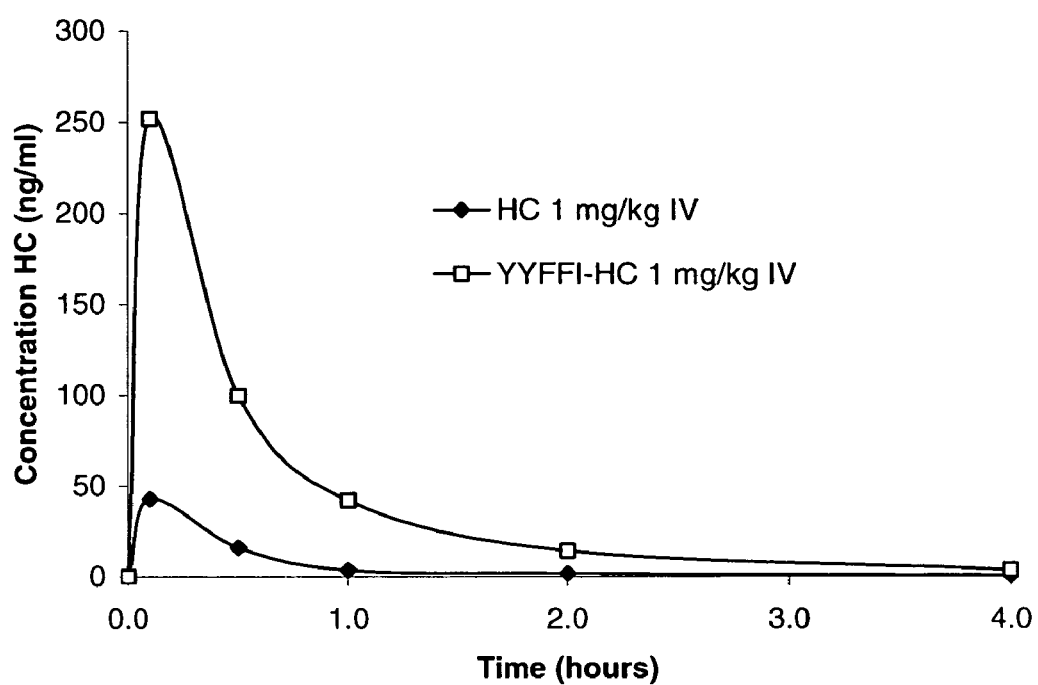
FIG. 73. Intravenous bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 74:
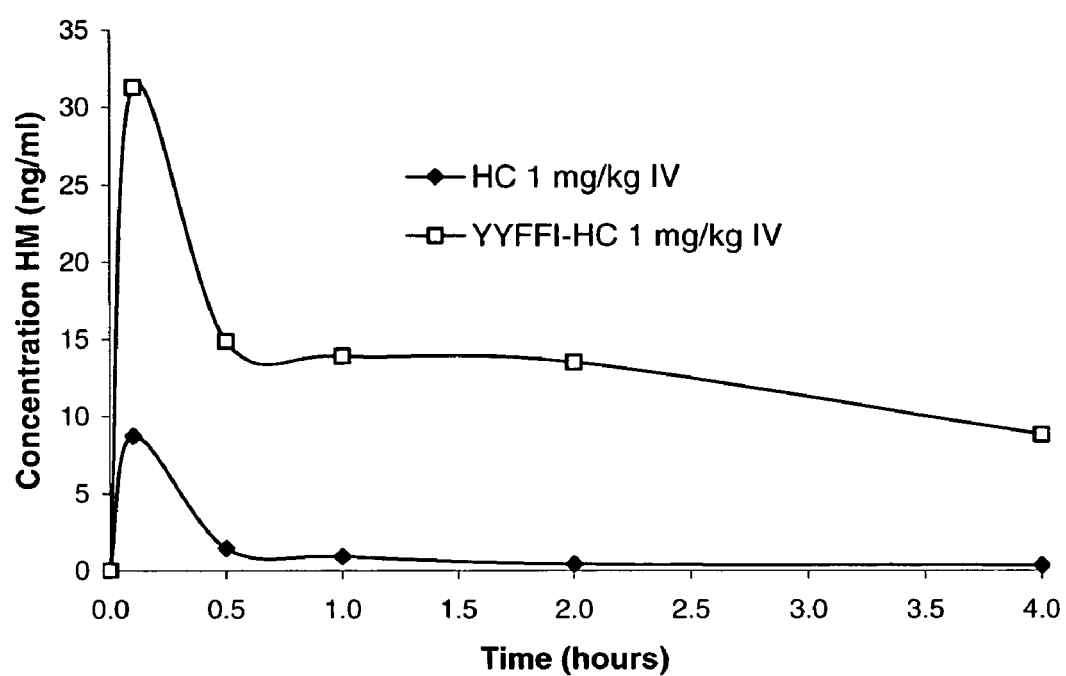
FIG. 74. Intravenous bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 75:
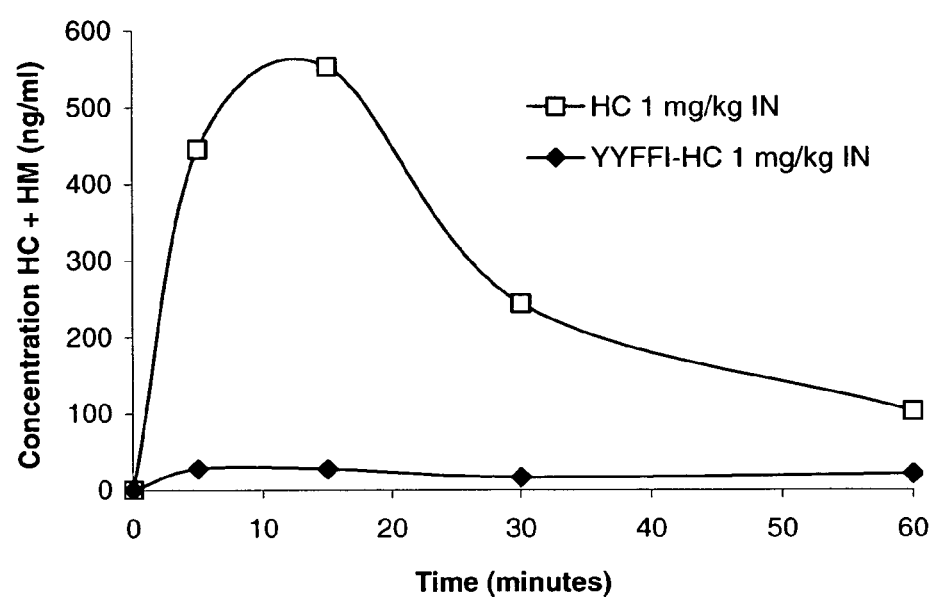
FIG. 75. Intranasal bioavailability of hydrocodone plus hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 76:
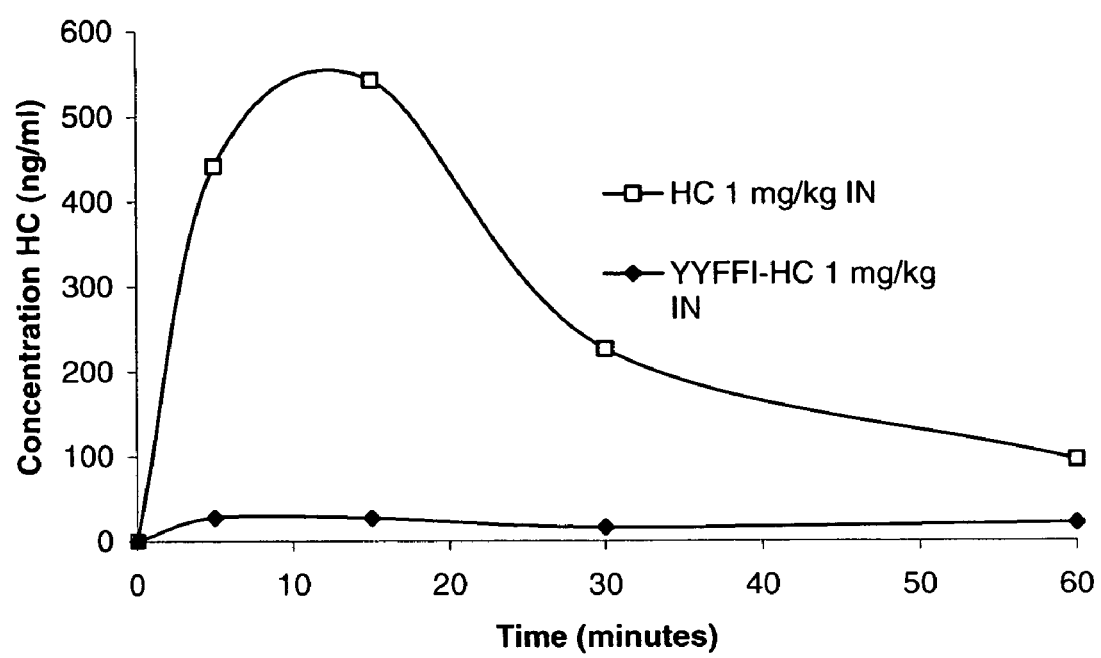
FIG. 76. Intranasal bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 77:
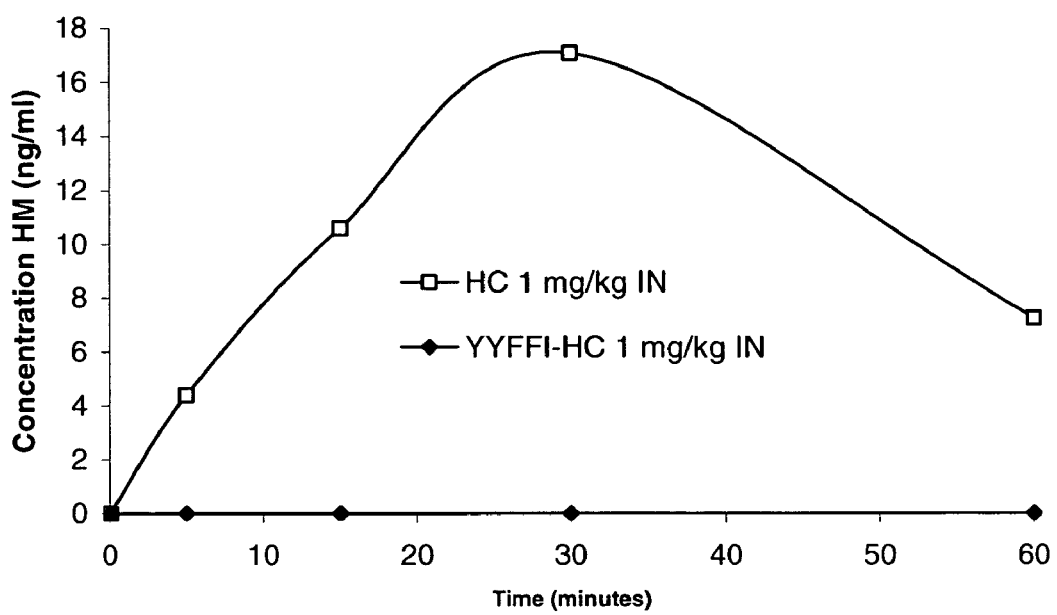
FIG. 77. Intranasal bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 78:
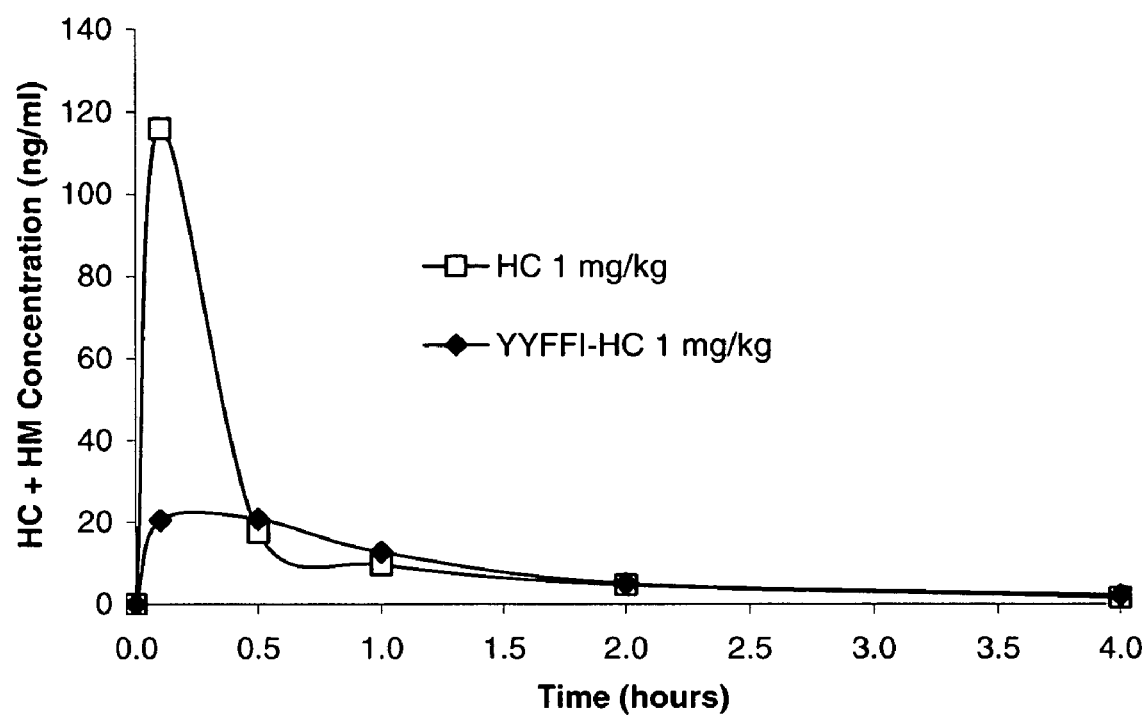
FIG. 78. Oral bioavailability of hydrocodone plus hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 79:
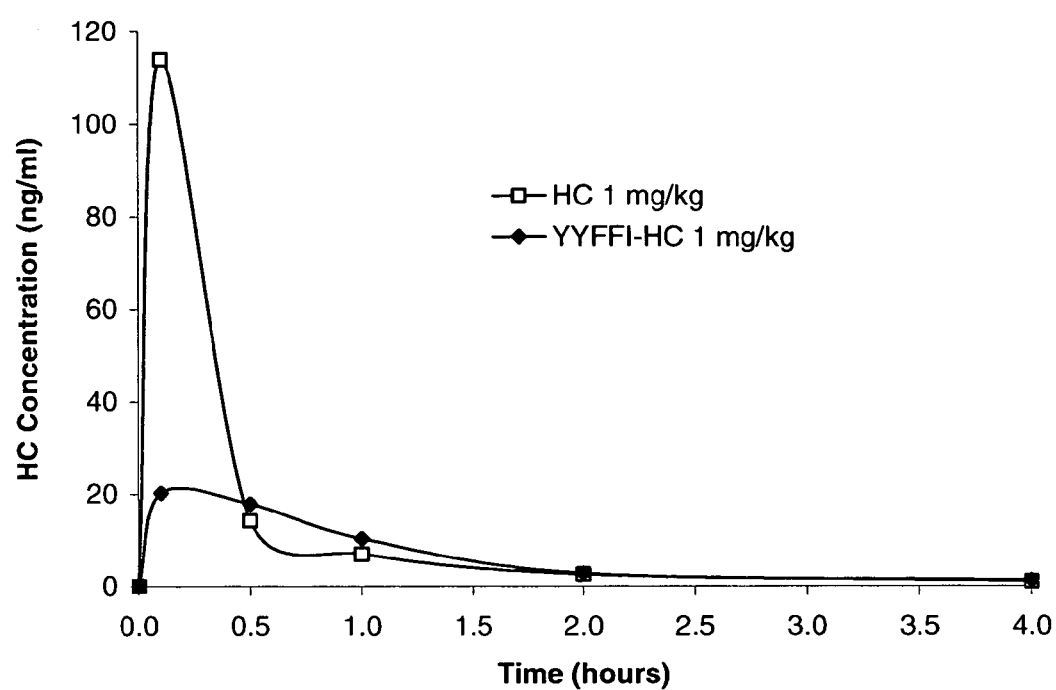
FIG. 79. Oral bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 80:
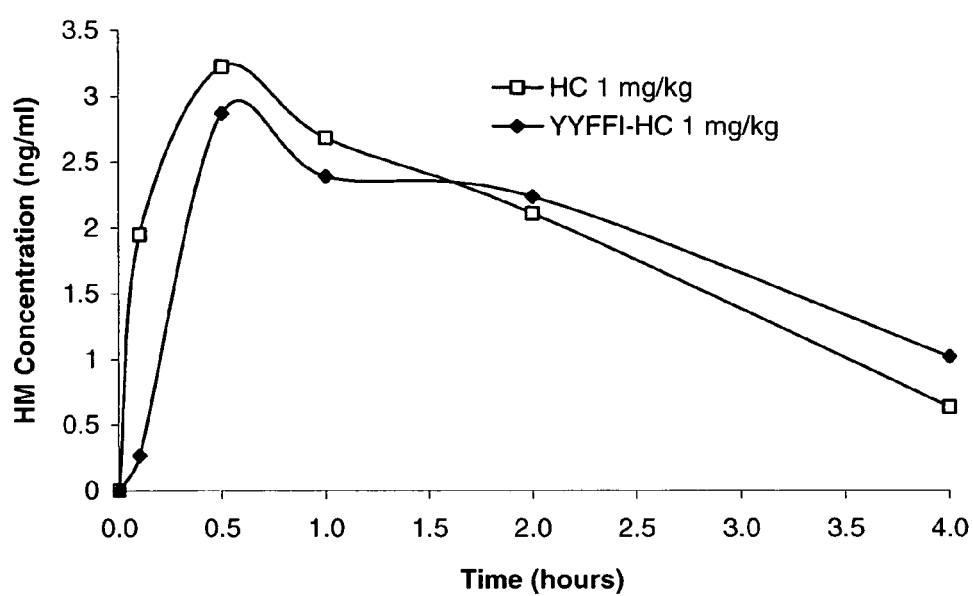
FIG. 80. Oral bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 81:
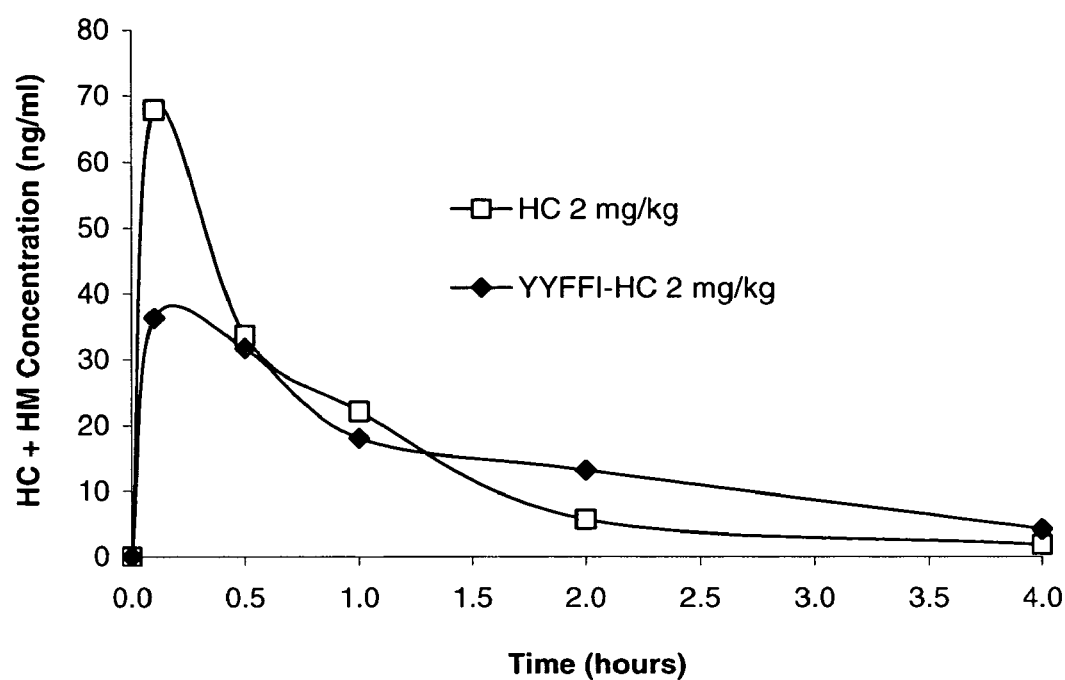
FIG. 81. Oral bioavailability of hydrocodone plus hydromorphone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 82:
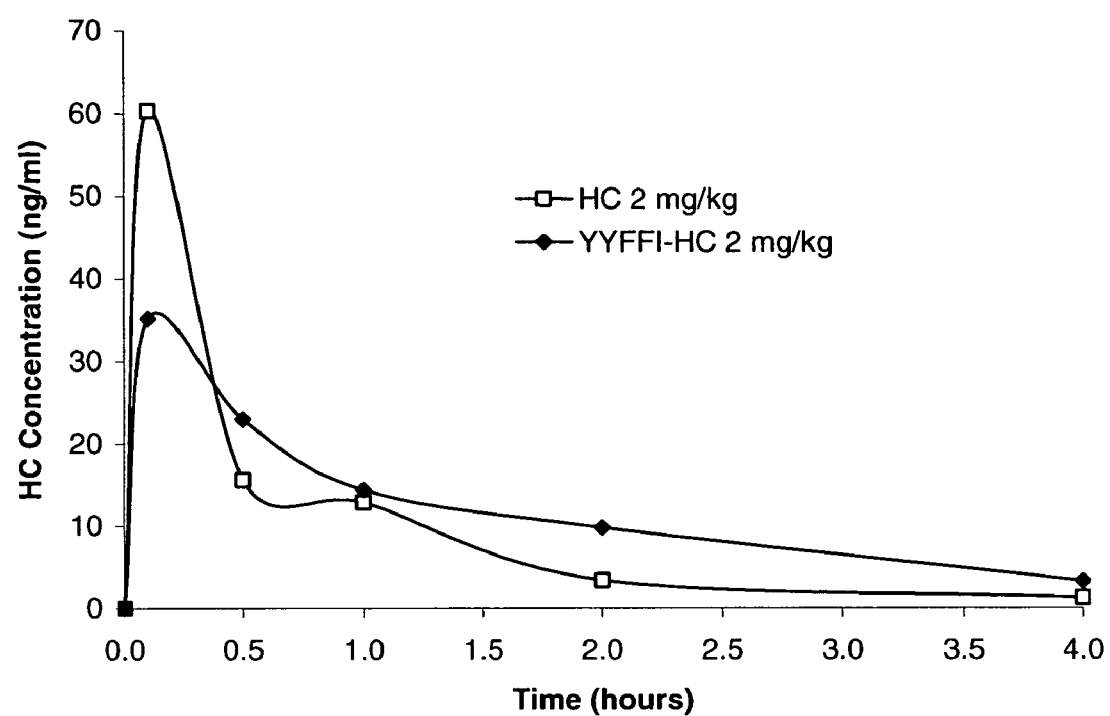
FIG. 82. Oral bioavailability of hydrocodone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 83:
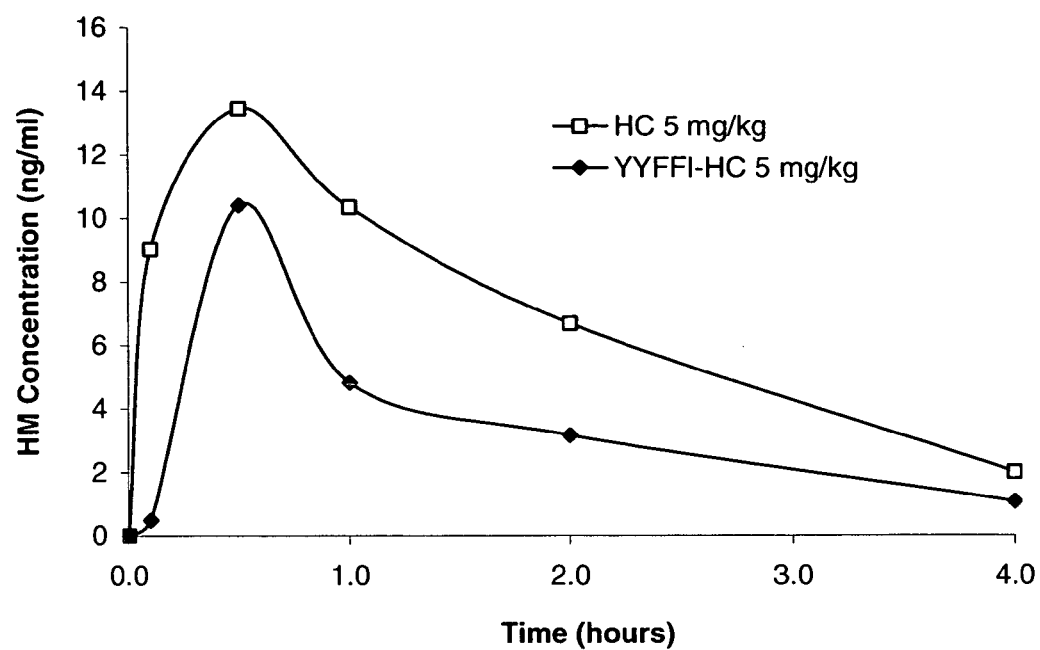
FIG. 83. Oral bioavailability of hydromorphone (concentration vs. time) following administration of hydrocodone bitratrate or YYFFI[SEQ ID NO: 4]-HC at 2 mg/kg (equimolar doses with equivalent content of hydrocodone base) in rats, measured as free hydrocodone.
Figure 84:
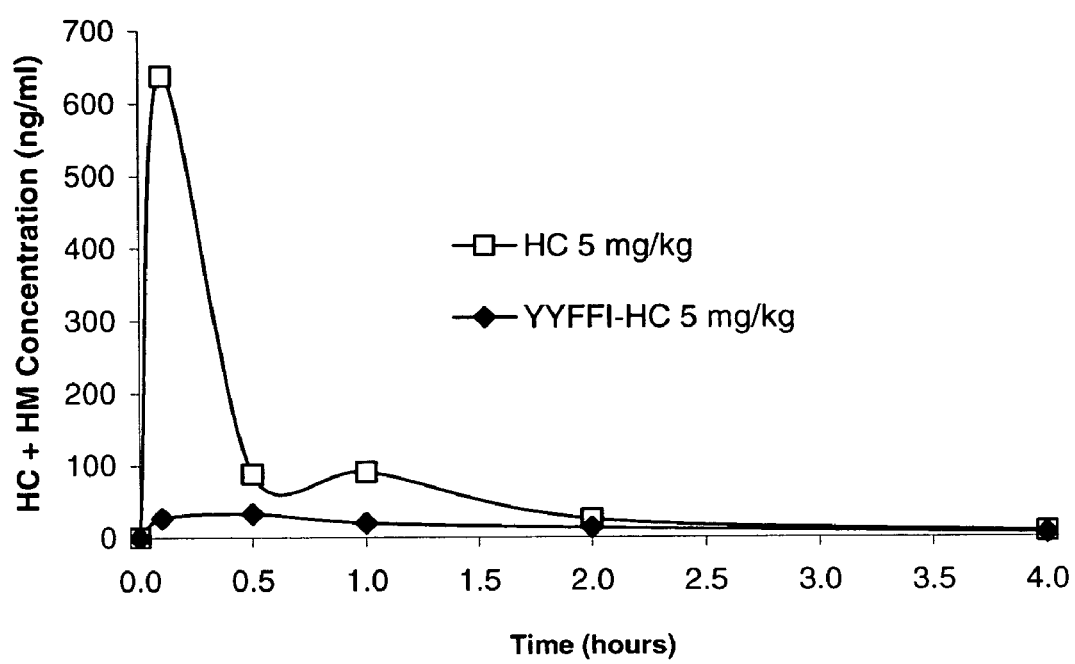
FIG. 84. Oral bioavailability of hydrocodone plus hydromorphone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 85:
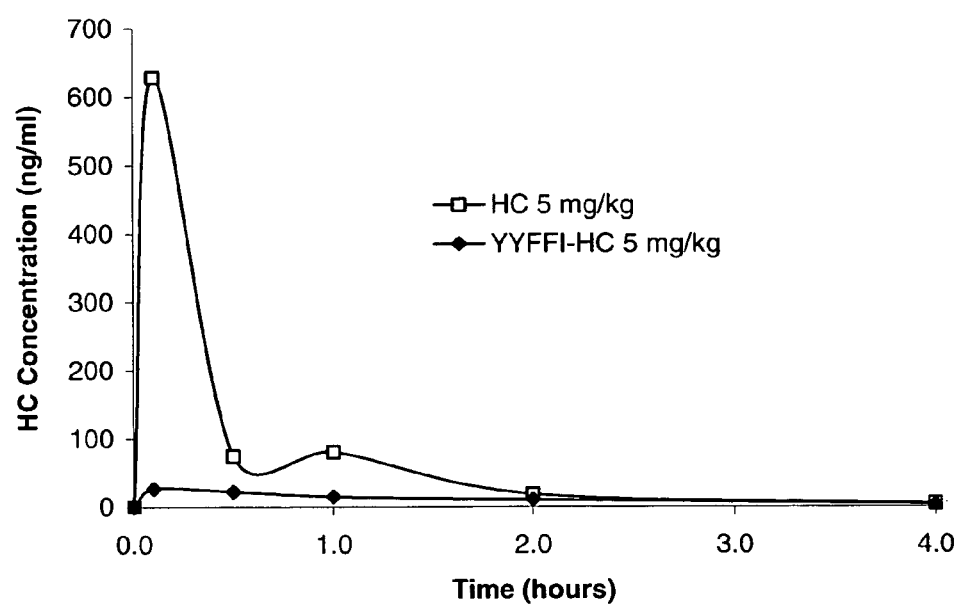
FIG. 85. Oral bioavailability of hydrocodone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 86:
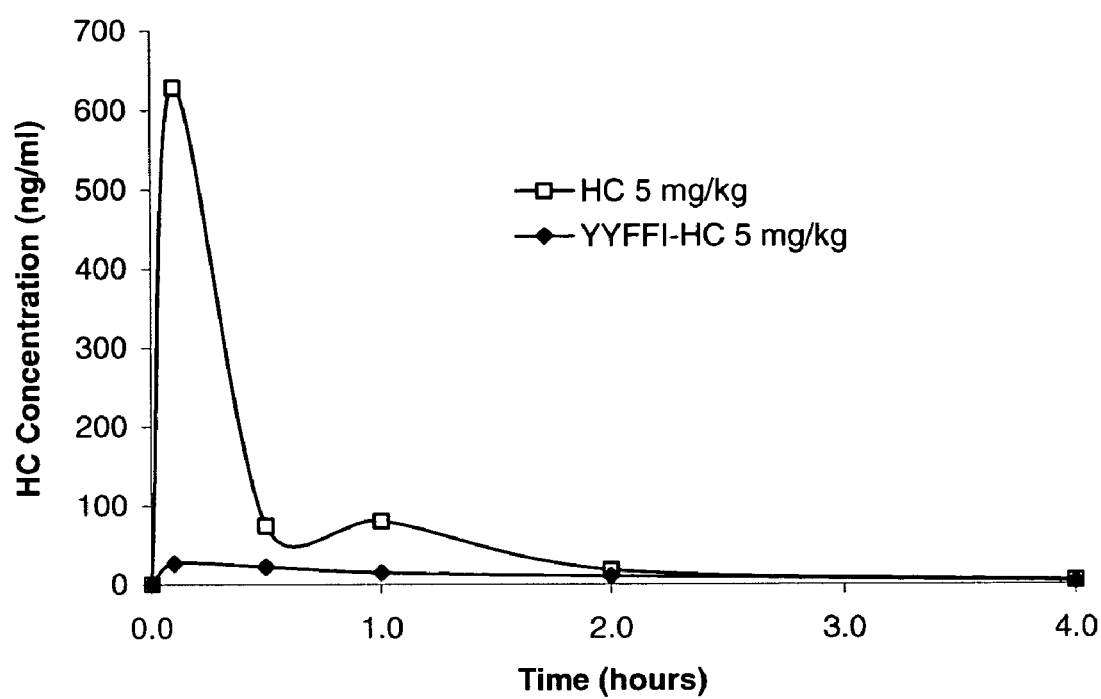
FIG. 86. Oral bioavailability of hydromorphone (concentration vs. time) following administration of hydrocodone bitratrate or YYFFI[SEQ ID NO: 4]-HC at 5 mg/kg (equimolar doses with equivalent content of hydrocodone base) in rats, measured as free hydrocodone.
Figure 87:
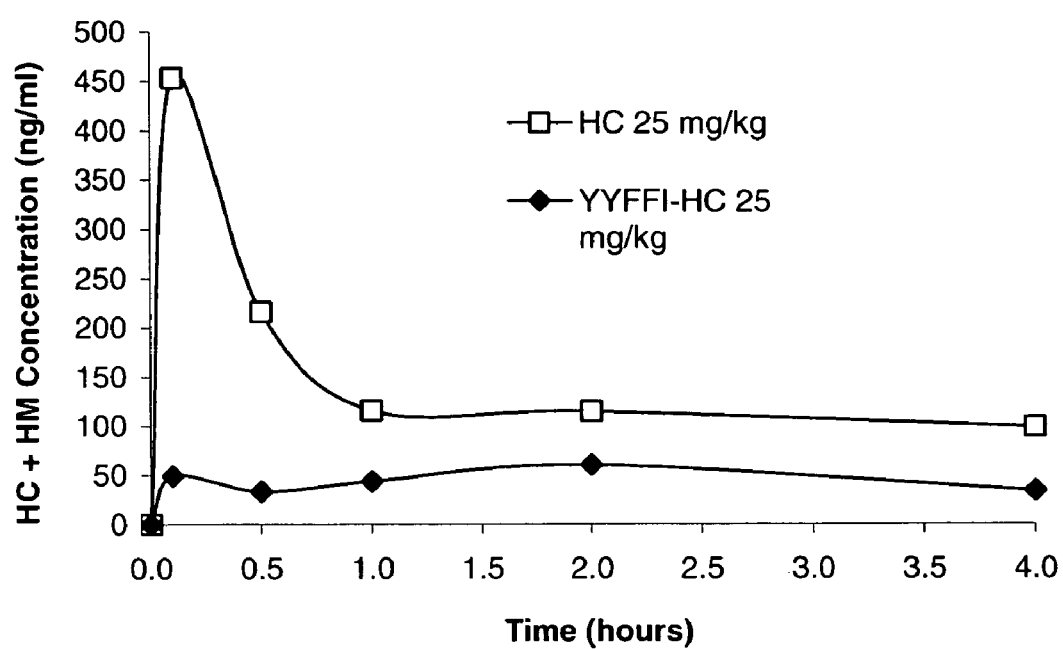
FIG. 87. Oral bioavailability of hydrocodone plus hydromorphone (concentration vs. time) following administration of hydrocodone bitratrate or YYFFI[SEQ ID NO: 4]-HC at 25 mg/kg (equimolar doses with equivalent content of hydrocodone base) in rats, measured as free hydrocodone.
Figure 88:
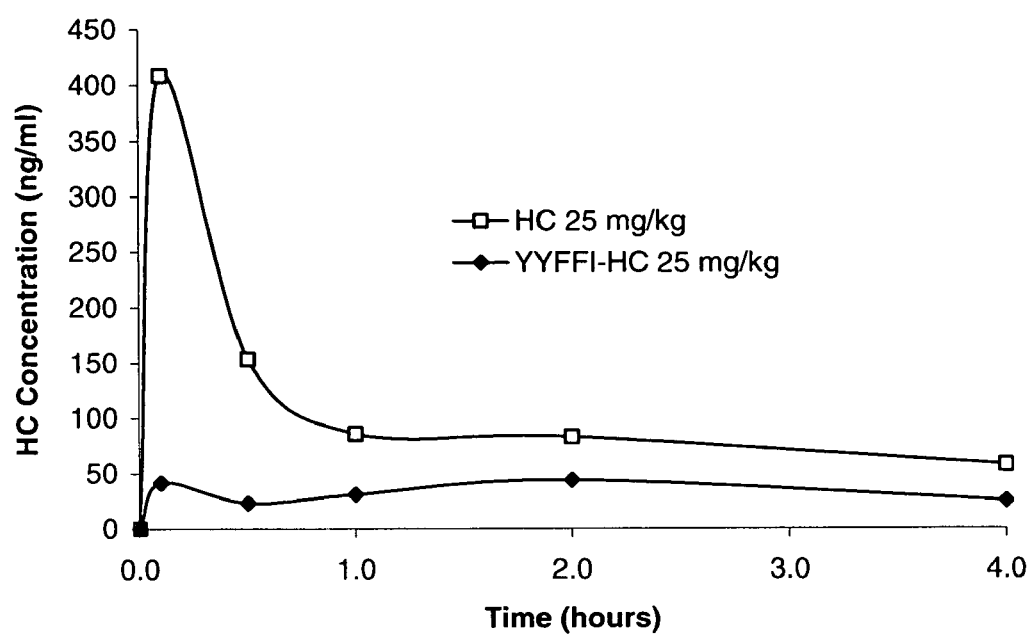
FIG. 88. Oral bioavailability of hydrocodone (concentration vs. time) following administration of hydrocodone FIG. 89. Oral bioavailability of hydromorphone (concentration vs. time) following administration of hydrocodone bitratrate or YYFFI[SEQ ID NO: 4]-HC at 25 mg/kg (equimolar doses with equivalent content of hydrocodone base) in rats, measured as free hydrocodone.
Figure 89:
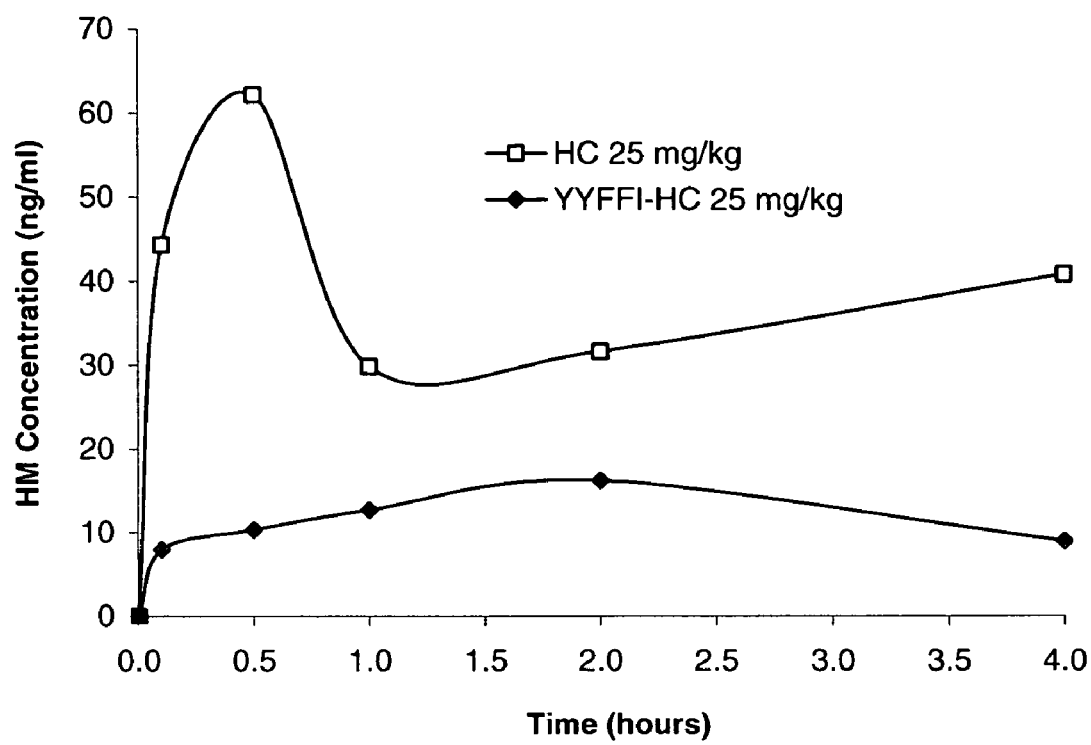
Figure 90:
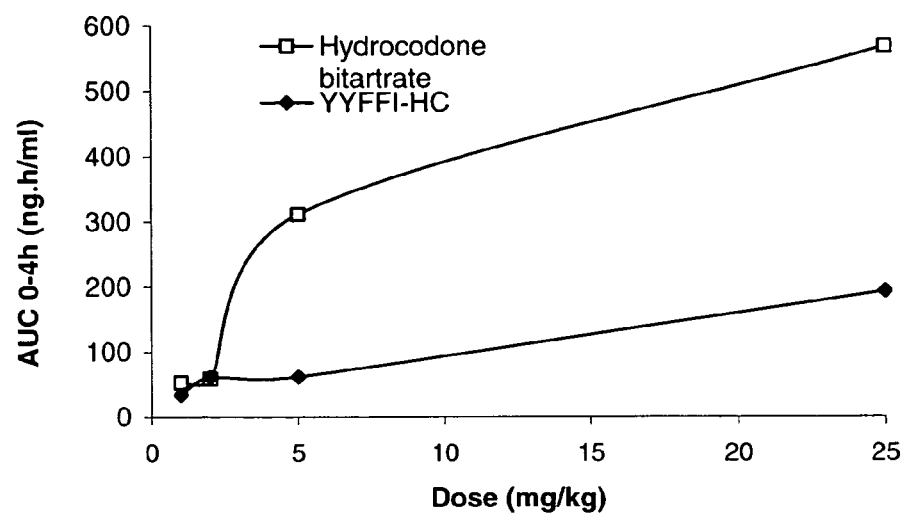
FIG. 90. Oral bioavailability ($AUC_{0-4}$) of hydrocodone plus hydromorphone (concentration vs. dose) in proportion to dose following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 91:
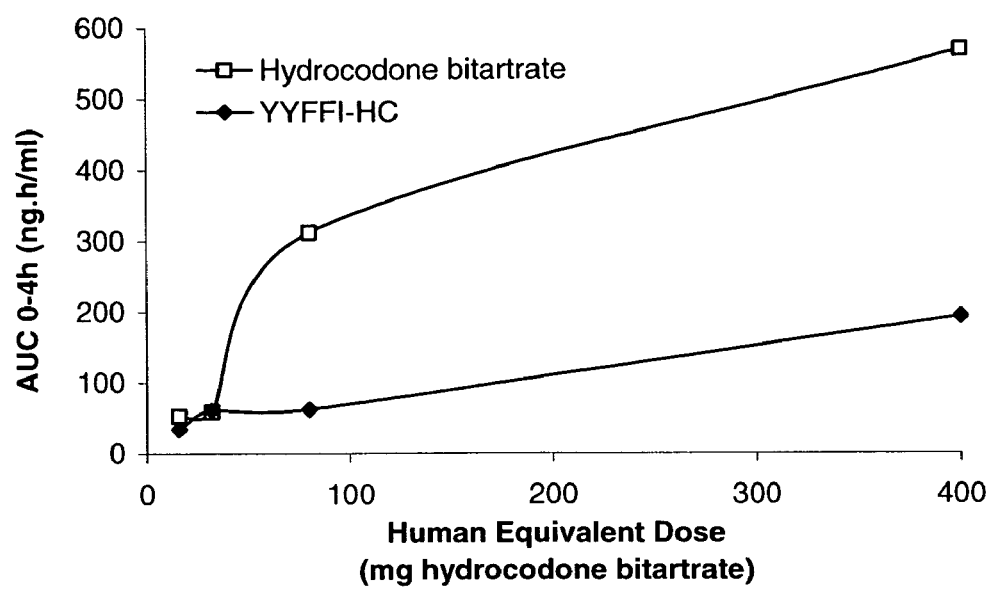
FIG. 91. Oral bioavailability ($AUC_{0-4}$) of hydrocodone plus hydromorphone in proportion to human equivalent doses (HED) following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 92:
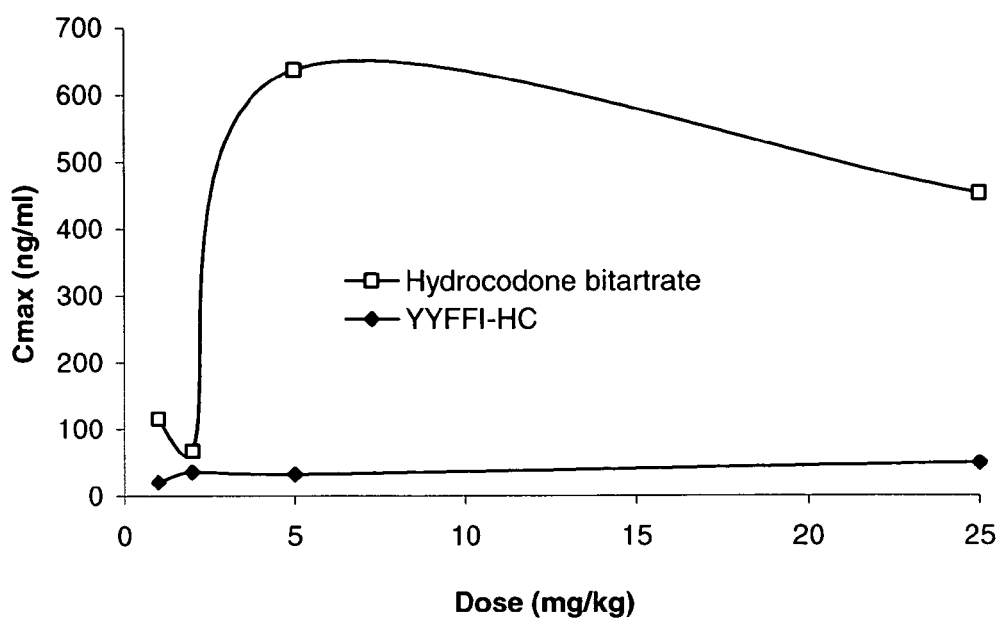
FIG. 92. Oral bioavailability ($C_{max}$) of hydrocodone plus hydromorphone (concentration vs. dose) in proportion to dose following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 93:
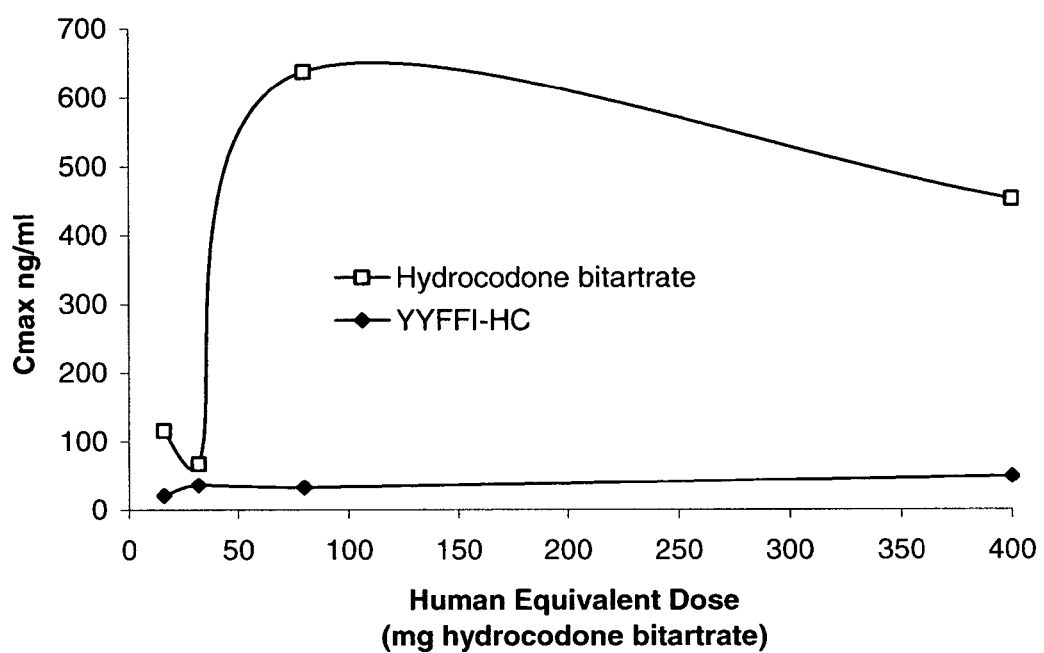
FIG. 93. Oral bioavailability ($C_{max}$) of hydrocodone plus hydromorphone in proportion to human equivalent doses (HED) following administration of hydrocodone bitratrate or YYFFI[SEQ ID NO: 4]-HC at escalating doses (1, 2, 5, and 25 mg/kg—equimolar doses with equivalent content of hydrocodone base) in rats, measured as free hydrocodone.
Figure 94:
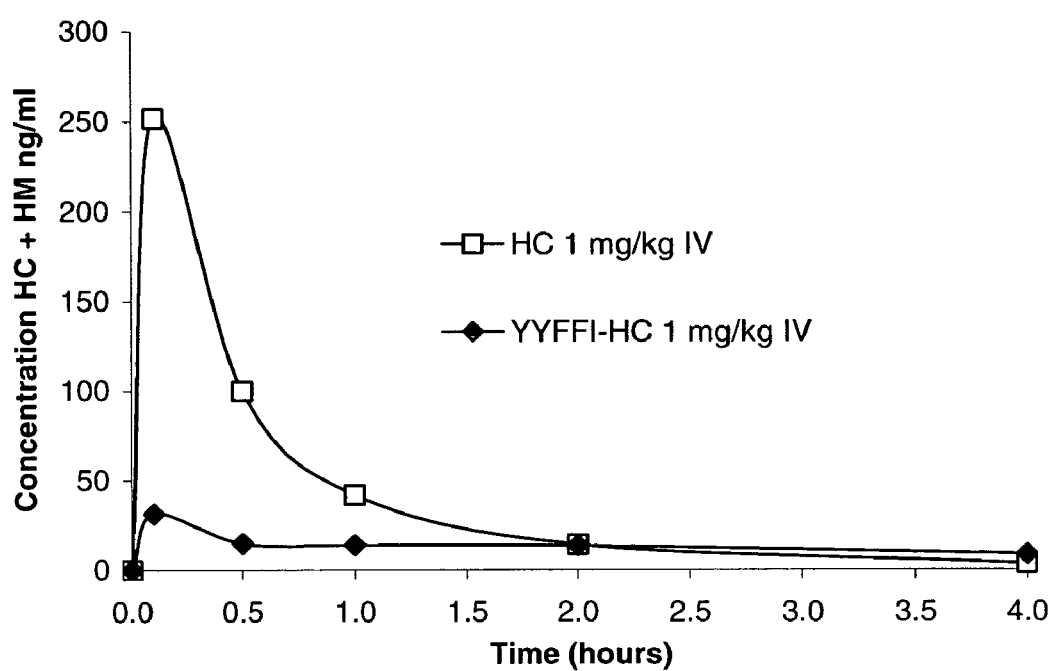
FIG. 94. Intravenous bioavailability of hydrocodone plus hydromorphone and YYFFI[SEQ ID NO: 4]-HC (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 95:
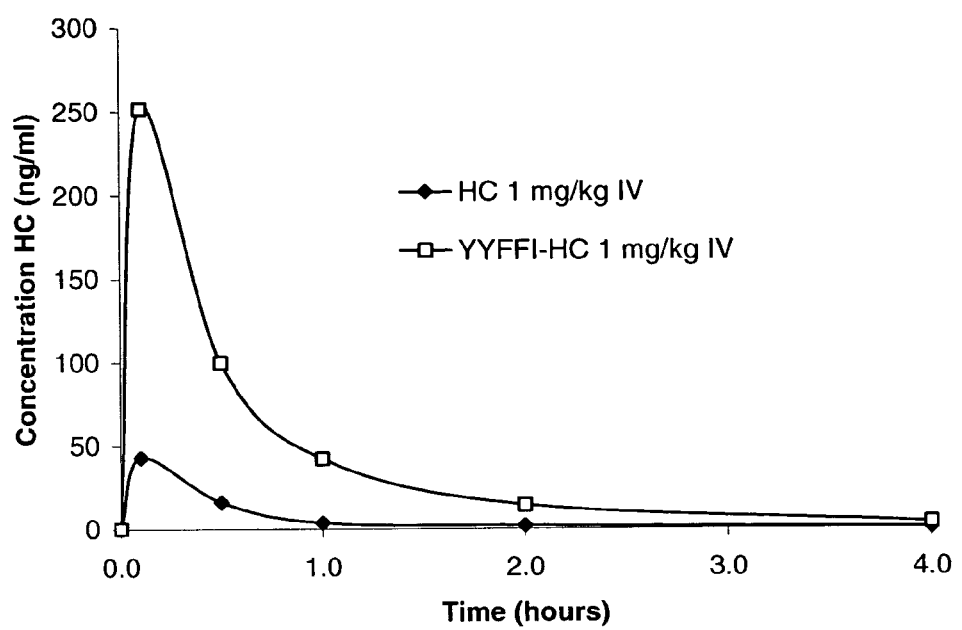
FIG. 95. Intravenous bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 96:
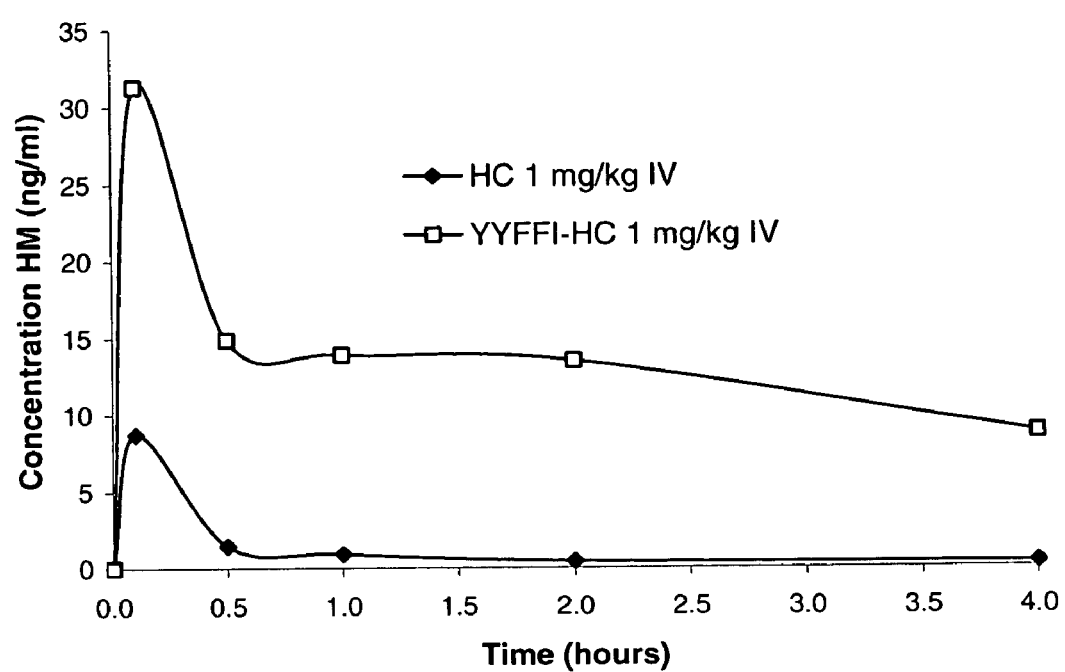
FIG. 96. Intravenous bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 97:
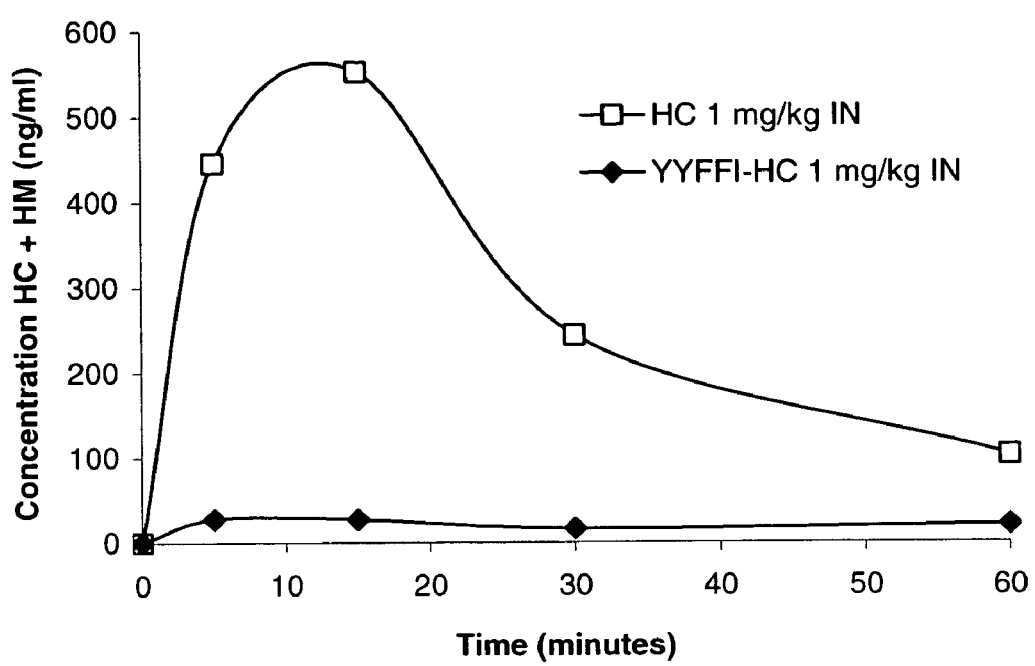
FIG. 97. Intranasal bioavailability of hydrocodone plus hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 98:
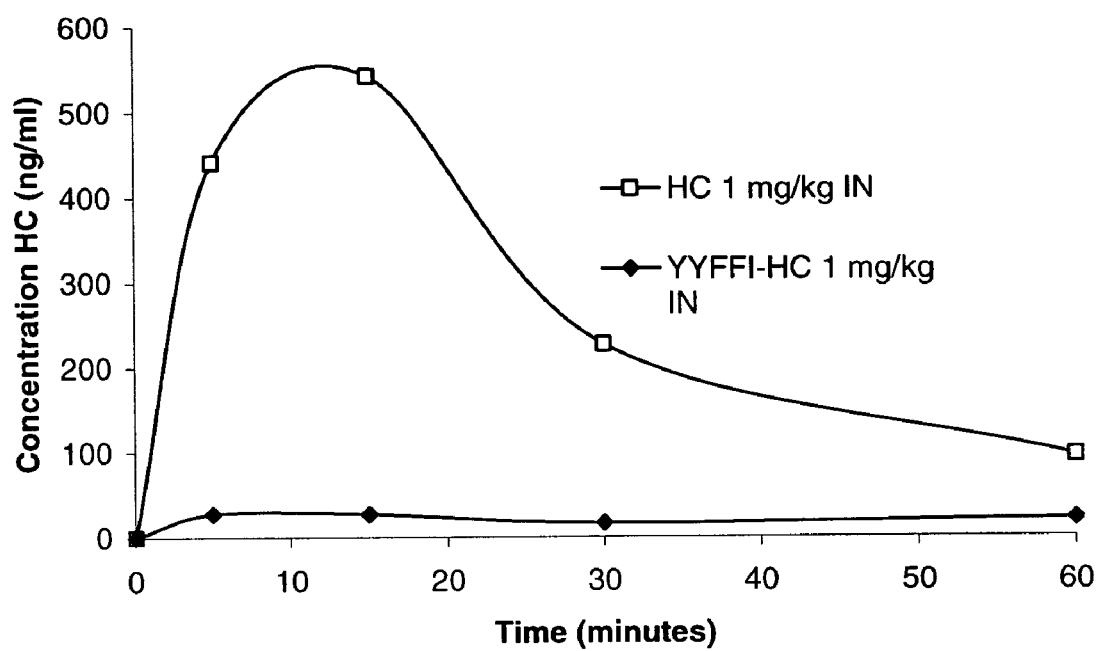
FIG. 98. Intranasal bioavailability of hydrocodone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.
Figure 99:
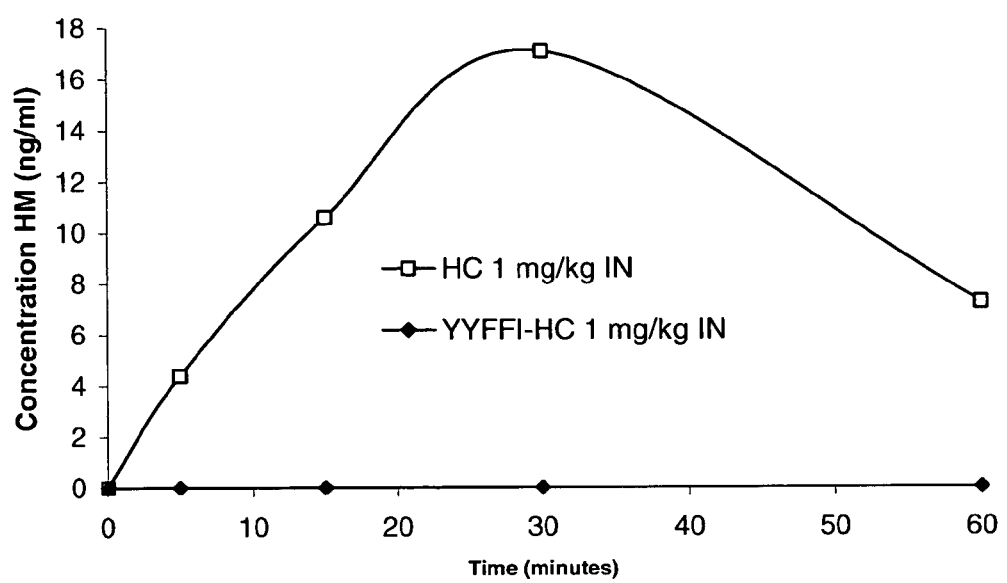
FIG. 99. Intranasal bioavailability of hydromorphone (concentration vs. time) following administration of hydrocodone bitratrate or YYFFI[SEQ ID NO: 4]-HC at 1 mg/kg (equimolar doses with equivalent content of hydrocodone base) in rats, measured as free hydrocodone.

FIG. 38 illustrates nucleosides and conjugation sites. Examples 42 through 51 are also described through FIGS. 39 through 77 (with plasma levels measured by LC/MS/MS).

Example 42

Oral Bioavailability of Peptide-hydrocodone Conjugates at a Dose (1 mg/kg) Approximating a Therapeutic Human Dose and at an Elevated Dose Example 42 illustrates that when the peptides EEFFI [SEQ ID NO: 5] (Table 1, FIG. 39), EEFFF [SEQ ID NO: 3] (Table 2, FIG. 40), YYI (Table 3, FIG. 41), DDI (Table 4, FIG. 42), and YYFFI [SEQ ID NO: 4] (Table 5, FIG. 43) are conjugated to the active agent hydrocodone oral bioavailability is maintained or increased over an equivalent hydrocodone dose when the dose is administered as 1 mg/kg. This dose is the equivalent of a human dose of 10 to 14 mg for an individual weighing 70 kg (148 lbs) according to Chou et al. However, when administered orally at 5 mg/kg peak levels and bioavailability of EEFFI[SEQ ID NO: 5]-HC (Table 6, FIG. 44), YYI-HC (Table 7, FIG. 45), DDI-HC (Table 8, FIG. 46) and YYFFI[SEQ ID NO: 4]-HC (Table 9, FIG. 47) are substantially decreased. A 5 mg/kg dose in rats approximates an 80 mg human equivalent dose (HED) of hydrocodone bitartrate; a dose that would be likely to be harmful to a naïve patient in immediate release form with the potential for fatal overdose. Human equivalent doses are defined as the equivalent dose for a 60 kg person adjusted for the body surface area of the animal model. The adjustment factor for rats is 6.2. The HED for a rat dose of 5 mg/kg of hydrocodone base, for example, is equivalent to 48.39 mg (5/6.2×60) hydrocodone base; which is equivalent to 79.98 (48.39/0.605) mg hydrocodone bitartrate, when adjusted for the salt content.

Thus the peptide-hydrocodone conjugates maintain their therapeutic value at the lower dose (1 mg/kg), whereas when given at a dose above a safe level (5 mg/kg) bioavailability is decreased as compared to hydrocodone, thus diminishing the potential for overdose by oral ingestion. The decrease in bioavailability of hydrocodone from peptide hydrocodone conjugates relative to hydrocodone ranged from 9 to 70 percent (Table 10).

TABLE 1

Oral Pharmacokinetics of Hydrocodone vs. EEFFI[SEQ ID NO: 5]-HC (1 mg/kg dose).

| Drug | Hours | | | | | AUC (ng/ml h) 0-8 h | Percent | Cmax ng/ml | Percent HC |
|---|---|---|---|---|---|---|---|---|---|
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |

TABLE 1-continued

Oral Pharmacokinetics of Hydrocodone vs. EEFFI[SEQ ID NO: 5]-HC (1 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| EEFFI [SEQ ID NO: 5]-HC | 12.9 | 5.2 | 4.2 | 0 | 1.6 | 25.8 | 135 | 12.9 | 136 | hydrocodone plus hydromorphone (ng/ml)

TABLE 2

Oral Pharmacokinetics of Hydrocodone vs. EEFFF[SEQ ID NO: 3]-HC (1 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |
| EEFFF [SEQ ID NO: 3]-HC | 11.3 | 4.1 | 1.2 | 1.2 | 1.2 | 20.7 | 108 | 11.3 | 119 | hydrocodone plus hydromorphone (ng/ml)

TABLE 3

Oral Pharmacokinetics of Hydrocodone vs. YYI-HC (1 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 9.2 | 5.9 | 2.3 | 1.9 | 2 | 26.1 | 100 | 9.2 | 100 |
| YYI-HC | 9.2 | 4.3 | 1.5 | 1.1 | 1.8 | 20.4 | 78 | 9.2 | 100 | hydrocodone plus hydromorphone (ng/ml)

TABLE 4

Oral Pharmacokinetics of Hydrocodone vs. DDI-HC (1 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 8.6 | 3 | 1.1 | 0 | 1.4 | 14 | 100 | 8.6 | 100 |
| DDI-HC | 14.9 | 5 | 0 | 0 | 0 | 17.4 | 124 | 14.9 | 173 | hydrocodone plus hydromorphone (ng/ml)

TABLE 5

Oral Pharmacokinetics of Hydrocodone vs. YYFFI[SEQ ID NO: 4]-HC (1 mg/kg dose).

| Drug | Hours | | | | | | AUC (ng/ml h) 0-8 h | Percent HC | Cmax ng/ml | Percent HC |
|---|---|---|---|---|---|---|---|---|---|---|
| | 0.5 | 1.0 | 1.5 | 3 | 5 | 8 | | | | |
| Hydrocodone Bitartrate | 8.6 | 4.5 | 3 | 1.1 | 0 | 1.4 | 13.6 | 100 | 8.6 | 100 |
| YYFFI [SEQ ID NO: 4]-HC | 7 | 3.7 | 4.3 | 1.4 | 1.1 | 0 | 14.9 | 110 | 7 | 81 | hydrocodone plus hydromorphone (ng/ml)

TABLE 6

Oral Pharmacokinetics of Hydrocodone vs. EEFFI[SEQ ID NO: 5]-HC (5 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 93 | 5.3 | 39 | 5 | 6.5 | 167 | 100 | 93 | 100 |
| EEFFI [SEQ ID NO: 5]-HC | 44 | 6.5 | 5.7 | 4.2 | 4.5 | 68 | 41 | 44 | 47 | hydrocodone plus hydromorphone (ng/ml)

TABLE 7

Oral Pharmacokinetics of Hydrocodone vs. YYI-HC (5 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 37 | 13 | 12 | 3 | 0 | 71 | 100 | 37 | 100 |
| YYI-HC | 15 | 6.3 | 3.3 | 1.6 | 2.7 | 33 | 46 | 15 | 41 | hydrocodone plus hydromorphone (ng/ml)

TABLE 8

Oral Pharmacokinetics of Hydrocodone vs. DDI-HC (5 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 73 | 42 | 6.7 | 1.2 | 3.8 | 128 | 100 | 73 | 100 |
| DDI-HC | 115 | 19 | 11 | 4 | 3.1 | 145 | 113 | 115 | 158 | hydrocodone plus hydromorphone (ng/ml)

TABLE 9

Oral Pharmacokinetics of Hydrocodone vs. YYFFI[SEQ ID NO: 4]-HC (5 mg/kg dose).

| Drug | \multicolumn{6}{c}{Hours} | AUC (ng/ml h) 0-8 h | Percent HC | Cmax ng/ml | Percent HC |
|---|---|---|---|---|---|---|---|---|---|---|
|  | 0.5 | 1.0 | 1.5 | 3 | 5 | 8 |  |  |  |  |
| Hydrocodone Bitartrate | 73 | 62 | 42 | 6.7 | 1.2 | 3.8 | 123 | 100 | 73 | 100 |
| YYFFI [SEQ ID NO: 4]-HC | 46 | 33 | 34 | 13 | 8.3 | 4.5 | 105 | 86 | 46 | 63 | hydrocodone plus hydromorphone (ng/ml)

TABLE 10

Decrease in Oral Bioavailability at 5 mg/kg vs. Therapeutic Dose of 1 mg/kg.

| Drug | Bioavailability 1 mg/kg | | Bioavailability 5 mg/kg | | Percent Decrease 1 mg/kg vs. 5 mg/kg | |
|---|---|---|---|---|---|---|
|  | AUC | Cmax | AUC | Cmax | AUC | Cmax |
| YYI-HC | 78 | 100 | 46 | 40 | 41 | 60 |
| DDI-HC | 124 | 174 | 113 | 158 | 9 | 9 |
| YYFFI [SEQ ID NO: 4]-HC | 109 | 81 | 86 | 62 | 15 | 23 |
| EEFFI-HC [SEQ ID NO: 5] | 135 | 136 | 41 | 47 | 70 | 65 |

Example 43

Bioavailability of Peptide-HC Conjugates by the Intranasal Route

Example 43 illustrates that when the peptides EEFFF [SEQ ID NO: 3] (Table 11, FIG. 48), YYI (Table 12, FIG. 49), DDI (Table 13, FIG. 50) and YYFFI [SEQ ID NO: 4] (Table 14, FIG. 51) are conjugated to the active agent hydrocodone the bioavailability by the intravenous route is substantially decreased thereby diminishing the possibility of overdose when the drug is administered by snorting.

TABLE 11

Intranasal Pharmacokinetics of Hydrocodone vs. EEFFF[SEQ ID NO: 3]-HC (1 mg/kg dose).

| Drug | \multicolumn{4}{c}{Minutes} | AUC (ng/ml h) 0-1 h | Percent HC | Cmax ng/ml | Percent HC |
|---|---|---|---|---|---|---|---|---|
|  | 5 | 15 | 30 | 60 |  |  |  |  |
| Hydrocodone Bitartrate | 262 | 259 | 142 | 47 | 152 | 100 | 262 | 100 |
| EEFFF[SEQ ID NO: 3]-HC | 34 | 21 | 24 | 15 | 21 | 14 | 34 | 13 | hydrocodone plus hydromorphone (ng/ml)

TABLE 12

Intranasal Pharmacokinetics of Hydrocodone vs. YYI-HC (1 mg/kg dose)

| Drug | \multicolumn{4}{c}{Minutes} | AUC (ng/ml h) 0-1 h | Percent HC | Cmax ng/ml | Percent HC |
|---|---|---|---|---|---|---|---|---|
|  | 5 | 15 | 30 | 60 |  |  |  |  |
| Hydrocodone Bitartrate | 446 | 553 | 244 | 103 | 288 | 100 | 553 | 100 |
| YYI-HC | 31 | 17 | 12 | 2 | 12 | 4 | 31 | 6 | hydrocodone plus hydromorphone (ng/ml)

TABLE 13

Intranasal Pharmacokinetics of Hydrocodone vs. DDI-HC (1 mg/kg dose).

| Drug | \multicolumn{4}{c}{Minutes} | AUC (ng/ml h) 0-1 h | Percent HC | Cmax ng/ml | Percent HC |
|---|---|---|---|---|---|---|---|---|
|  | 5 | 15 | 30 | 60 |  |  |  |  |
| Hydrocodone Bitartrate | 446 | 553 | 244 | 103 | 288 | 100 | 553 | 100 |
| DDI-HC | 281 | 121 | 64 | 16 | 88 | 31 | 281 | 51 | hydrocodone plus hydromorphone (ng/ml)

TABLE 14

Intranasal Pharmacokinetics of Hydrocodone vs. YYFFI[SEQ ID NO: 4]-HC (1 mg/kg dose).

| | Minutes | | | | AUC (ng/ml h) | Percent | Cmax | Percent |
|---|---|---|---|---|---|---|---|---|
| Drug | 5 | 15 | 30 | 60 | 0-1 h | HC | ng/ml | HC |
| Hydrocodone Bitartrate | 446 | 553 | 244 | 103 | 288 | 100 | 553 | 100 |
| YYFFI[SEQ ID NO: 4]-HC | 28 | 27 | 16 | 21 | 20 | 100 | 28 | 5 | hydrocodone plus hydromorphone (ng/ml)

Example 44

Bioavailability of Peptide-HC Conjugates by the Intravenous Route

Example 44 illustrates that when the peptides EEFFI [SEQ ID NO: 5] (Table 15, FIG. 52), EEFFF [SEQ ID NO: 3] (Table 16, FIG. 53), YYI (Table 17, FIG. 54) and YYFFI [SEQ ID NO: 4] (Table 18, FIG. 55) are conjugated to the active agent hydrocodone the bioavailability by the intravenous route is substantially decreased thereby diminishing the possibility of overdose when the drug is administered by this unintended route.

TABLE 15

Intravenous Pharmacokinetics of Hydrocodone vs. EEFFI[SEQ ID NO: 5]-HC (1 mg/kg dose).

| | Minutes | | | | AUC (ng/ml h) | Percent | Cmax | Percent |
|---|---|---|---|---|---|---|---|---|
| Drug | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFI[SEQ ID NO: 5]-HC | 89 | 76 | 78 | 66 | 66 | 38 | 89 | 44 | hydrocodone plus hydromorphone (ng/ml)

TABLE 16

Intravenous Pharmacokinetics of Hydrocodone vs. EEFFF[SEQ ID NO: 3]-HC (1 mg/kg dose).

| | Minutes | | | | AUC (ng/ml h) | Percent | Cmax | Percent |
|---|---|---|---|---|---|---|---|---|
| Drug | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFF[SEQ ID NO: 3]-HC | 135 | 77 | 140 | 85 | 107 | 62 | 135 | 75 | hydrocodone plus hydromorphone (ng/ml)

TABLE 17

Intravenous Pharmacokinetics of Hydrocodone vs. YYI-HC (1 mg/kg dose).

| | Minutes | | | | AUC (ng/ml h) | Percent | Cmax | Percent |
|---|---|---|---|---|---|---|---|---|
| Drug | 5 | 15 | 30 | 60 | 0-1 h | HC | ng/ml | HC |
| Hydrocodone Bitartrate | 238 | 182 | 136 | 77 | 138 | 100 | 238 | 100 |
| YYI-HC | 9 | 13 | 13 | 3 | 10 | 7 | 13 | 6 | hydrocodone plus hydromorphone (ng/ml)

TABLE 18

Intravenous Pharmacokinetics of Hydrocodone vs. YYFFI[SEQ ID NO: 4]-HC (1 mg/kg dose).

| Drug | Minutes | | | | AUC (ng/ml h) 0-1 h | Percent HC | Cmax ng/ml | Percent HC |
|---|---|---|---|---|---|---|---|---|
|  | 5 | 15 | 30 | 60 |  |  |  |  |
| Hydrocodone Bitartrate | 238 | 182 | 136 | 77 | 138 | 100 | 238 | 100 |
| YYFFI[SEQ ID NO: 4]-HC | 171 | 28 | 22 | 18 | 40 | 29 | 171 | 72 | hydrocodone plus hydromorphone (ng/ml)

Example 45

Hydrocodone Conjugates

Bioavailability (AUC and Cmax) of various peptide-hydrocodone conjugates relative to that of hydrocodone bitartrate are shown in Table 19. The invention is well illustrated by the in vivo performance of YYFFI[SEQ ID NO: 4]-HC (FIGS. 56 through 77). At the relatively low doses of 1 and 2 mg/kg (human equivalent doses (HEDs) of 16 and 32 mg hydrocodone bitartrate) YYFFI[SEQ ID NO: 4]-HC showed comparable bioavailability to that of hydrocodone bitartrate (Table 20, FIGS. 78 through 83). At the elevated doses of 5 and 25 mg/kg bioavailability of hydrocodone and hydromorphone were substantially decreased as compared to that of hydrocodone (Table 21, FIGS. 84 through 99). These doses (HED of 80 and 400 mg hydrocodone bitartrate) are equivalent to amounts well above the available prescription doses of hydrocodone bitartrate which range from 2.5 to 10 mg. When delivered by the parentaral routes of intravenous and intranasal administration a substantial decrease in bioavailability of hydrocodone and hydromorphone from YYFFI[SEQ ID NO: 4]-HC as compared to hydrocodone bitratrate was observed. These examples establish that covalent modification of an opioid via attachment of a peptide provides a method of delivering bioequivalent doses when given at doses approximating a normal prescribed dose. When administered by parenteral routes or at oral doses in excess of the intended prescription the bioavailability is substantially decreased. Collectively, the examples clearly illustrate the utility of the invention for decreasing the abuse potential of opioids.

TABLE 19

Mean hydrocodone concentrations following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| 0 | 0 | 0 | 0 | 0 | 0 | 0 | 0 | 0 |
| 0.1 | 114.0 | 20.3 | 60.3 | 35.2 | 628.7 | 26.6 | 408.9 | 41.4 |
| 0.5 | 14.3 | 17.9 | 15.6 | 23 | 74.3 | 22.5 | 153.9 | 23.3 |
| 1.0 | 7.0 | 10.4 | 12.9 | 14.4 | 80.8 | 15.1 | 86.2 | 31.0 |
| 2.0 | 2.6 | 2.8 | 3.4 | 9.8 | 18.4 | 10.3 | 83.3 | 43.9 |
| 4.0 | 1.0 | 1.2 | 1.3 | 3.3 | 4.9 | 3.6 | 57.8 | 25.0 |

[1]hydrocodone base content
[2]hydrocodone bitartrate
[3]YYFFI[SEQ ID NO: 4]-HC HCl

TABLE 20

Hydrocodone pharmacokinetic parameters following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| AUC | 45.1 | 26.3 | 38.2 | 48 | 234 | 47 | 419.0 | 135.0 |
| Percent HC + HM[4] | 100 | 58 | 100 | 126 | 100 | 20 | 100 | 32 |

TABLE 20-continued

Hydrocodone pharmacokinetic parameters following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| Cmax | 114.0 | 20.3 | 60.3 | 35.2 | 628.7 | 26.6 | 408.9 | 41.4 |
| Percent HC + HM[4] | 100 | 18 | 100 | 58 | 100 | 4 | 100 | 10 |

[1]hydrocodone base content
[2]hydrocodone bitartrate
[3]YYFFI[SEQ ID NO: 4]-HC HCl
[4]percent relative to parameter following administration of hydrocodone bitartrate

TABLE 21

Mean hydromorphone concentrations following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| 0 | 0 | 0 | 0 | 0 | 0 | 0 | 0 | 0 |
| 0.1 | 1.95 | 0.27 | 7.61 | 1.13 | 9.03 | 0.49 | 44.36 | 8.00 |
| 0.5 | 3.22 | 2.87 | 18.10 | 8.74 | 13.46 | 10.41 | 62.24 | 10.35 |
| 1.0 | 2.69 | 2.39 | 9.23 | 3.63 | 10.36 | 4.82 | 29.89 | 12.70 |
| 2.0 | 2.11 | 2.24 | 2.31 | 3.41 | 6.68 | 3.17 | 31.62 | 16.22 |
| 4.0 | 0.64 | 1.02 | 0.59 | 0.88 | 2.00 | 1.07 | 40.86 | 8.98 |

[1]hydrocodone base content
[2]hydrocodone bitartrate
[3]YYFFI[SEQ ID NO: 4]-HC HCl

TABLE 22

Hydromorphone pharmacokinetic parameters following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| AUC | 7.8 | 7.5 | 21.0 | 12.9 | 28.1 | 14.3 | 149 | 49 |
| Percent HM[4] | 100 | 97 | 100 | 61 | 100 | 51 | 100 | 33 |
| Cmax | 3.2 | 2.9 | 18.1 | 8.7 | 13.5 | 10.4 | 44.4 | 16.2 |
| Percent HM[4] | 100 | 89 | 100 | 48 | 100 | 77 | 100 | 37 |

[1]hydrocodone base content
[2]hydrocodone bitartrate
[3]YYFFI[SEQ ID NO: 4]-HC HCl
[4]percent relative to parameter following administration of hydrocodone bitartrate

TABLE 23

Mean hydrocodone plus hydromorphone concentrations following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| 0 | 0 | 0 | 0 | 0 | 0 | 0 | 0 | 0 |
| 0.1 | 116 | 20.6 | 67.9 | 36.3 | 637.7 | 27.1 | 453.3 | 49.4 |
| 0.5 | 17.5 | 20.;8 | 33.7 | 31.7 | 87.8 | 32.9 | 216.1 | 33.7 |
| 1.0 | 9.7 | 12.8 | 22.1 | 18.0 | 91.2 | 19.9 | 116.1 | 43.7 |
| 2.0 | 4.7 | 5.0 | 5.7 | 13.2 | 25.1 | 13.5 | 114.9 | 60.1 |
| 4.0 | 1.6 | 2.2 | 1.9 | 4.2 | 6.9 | 4.7 | 98.7 | 34.0 |

[1]hydrocodone base content
[2]hydrocodone bitartrate
[3]YYFFI[SEQ ID NO: 4]-HC HCl

TABLE 24

Hydrocodone plus hydromorphone pharmacokinetic parameters following oral administration of hydrocodone bitartrate or YYFFI[SEQ ID NO: 4]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] | HC[2] | YYFFI[SEQ ID NO: 4]-HC[3] |
| AUC | 53 | 34 | 59 | 61 | 312 | 62 | 569 | 193 |
| Percent HC[4] | 100 | 64 | 100 | 103 | 100 | 20 | 100 | 34 |
| Cmax | 116 | 20.8 | 67.9 | 36.3 | 638 | 32.9 | 453 | 49.4 |
| Percent HC[4] | 100 | 18 | 100 | 53 | 100 | 5 | 100 | 11 |

[1]hydrocodone base content
[2]hydrocodone bitartrate
[3]YYFFI[SEQ ID NO: 4]-HC HCl
[4]percent relative to parameter following administration of hydrocodone bitartrate

TABLE 25

Mean hydrocodone plus hydromorphone, hydrocodone, and hydromorphone, concentrations following intravenous administration of hydrocodone bitartrate or YYFFI[SEQ ID NO: 4]-HC at 1 mg/kg (hydrocodone base content).

| | Concentration (ng/ml) | | | | | |
|---|---|---|---|---|---|---|
| | HC + HM | | HC | | HM | |
| Hours | HC[1] | YYFFI[SEQ ID NO: 4]-HC[2] | HC[1] | YYFFI[SEQ ID NO: 4]-HC[2] | HC[1] | YYFFI[SEQ ID NO: 4]-HC[2] |
| 0 | 0 | 0 | 0 | 0 | 0 | 0 |
| 0.1 | 208.9 | 22.6 | 42.97 | 8.75 | 251.9 | 31.3 |
| 0.5 | 83.7 | 13.5 | 16.09 | 1.44 | 99.8 | 14.9 |
| 1.0 | 38.4 | 13.0 | 3.65 | 0.92 | 42.1 | 13.9 |
| 2.0 | 12.4 | 13.1 | 1.77 | 0.41 | 14.2 | 13.5 |
| 4.0 | 2.9 | 8.5 | 0.70 | 0.33 | 3.6 | 8.8 |

[1]hydrocodone bitartrate
[2]YYFFI[SEQ ID NO: 4]-HC HCl

TABLE 26

Hydrocodone plus hydromorphone, hydrocodone, and hydromorphone pharmacokinetic parameters following intravenous administration of hydrocodone bitartrate or YYFFI[SEQ ID NO: 4]-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI[SEQ ID NO: 4]-HC[2] | HC[1] | YYFFI[SEQ ID NO: 4]-HC[2] | HC[1] | YYFFI[SEQ ID NO: 4]-HC[2] |
| AUC | 140.0 | 50.0 | 24.10 | 4.50 | 164 | 54 |
| Percent[3] | 100 | 36 | 100 | 19 | 100 | 33 |
| Cmax | 208.9 | 22.6 | 43.0 | 8.7 | 252 | 31.3 |
| Percent[3] | 100 | 10.8 | 100 | 20.2 | 100 | 12.4 |

[1]hydrocodone bitartrate
[2]YYFFI[SEQ ID NO: 4]-HC HCl
[3]percent relative to parameter following administration of hydrocodone bitartrate

TABLE 27

Mean hydrocodone plus hydromorphone, hydrocodone, and hydromorphone, concentrations following intranasal administration of hydrocodone bitartrate or YYFFI[SEQ ID NO: 4]-HC at 1 mg/kg.

| | Concentration (ng/ml) | | | | | |
|---|---|---|---|---|---|---|
| | HC + HM | | HC | | HM | |
| Minutes | HC[1] | YYFFI[SEQ ID NO: 4]-HC[2] | HC[1] | YYFFI[SEQ ID NO: 4]-HC[2] | HC[1] | YYFFI[SEQ ID NO: 4]-HC[2] |
| 0 | 0 | 0 | 0 | 0 | 0 | 0 |
| 5 | 446 | 28 | 441 | 28 | 4.4 | bql[3] |
| 15 | 553 | 27 | 543 | 27 | 10.6 | bql[4] |
| 30 | 244 | 16 | 227 | 16 | 17.1 | bql[5] |
| 60 | 103 | 21 | 96 | 21 | 7.2 | bql[6] |

[1]hydrocodone bitartrate
[2]YYFFI[SEQ ID NO: 4]-HC HCl

TABLE 28

Hydrocodone plus hydromorphone, hydrocodone, and hydromorphone pharmacokinetic parameters following intravenous administration of hydrocodone bitartrate or YYFFI[SEQ ID NO: 4]-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI [SEQ ID NO: 4]-HC[2] | HC[1] | YYFFI [SEQ ID NO: 4]-HC[2] | HC[1] | YYFFI [SEQ ID NO: 4]-HC[2] |
| AUC | 288.0 | 20.0 | 74.70 | 10.30 | 7.0 | NA |
| Percent[3] | 100 | 6.9 | 100 | 13.8 | 100 | NA |
| Cmax | 553.0 | 28.0 | 543.0 | 28.0 | 17 | NA |
| Percent[3] | 100 | 5.1 | 100 | 5.2 | 100 | NA |

[1]hydrocodone bitartrate
[2]YYFFI[SEQ ID NO: 4]-HC HCl
[3]percent relative to parameter following administration of hydrocodone bitartrate Summary of in vivo testing of abuse resistant hydrocodone conjugates. In vivo testing of hydrocodone conjugates demonstrates for instance decreased intranasal analgesic response, decreased intravenous analgesic response, decreased subcutaneous analgesic response, decreased oral $C_{max}$, decreased intranasal bioavailability (AUC and $C_{max}$), and decreased intravenous bioavailability (AUC and $C_{max}$) of hydrocodone conjugates and is described in further detail below.

Example 46

Decreased Intranasal Analgesic Response to Hydrocodone Conjugates

Male Sprague-Dawley rats were dosed by placing 0.02 ml of water containing hydrocodone conjugate or hydrocodone bitartrate into the nasal flares. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curves shown in FIGS. 61 and 63 indicate the decrease in analgesia produced by the hydrocodone conjugates as compared to an equimolar (hydrocodone base) dose of hydrocodone bitartrate. The analgesic response as determined by the hot plate test is a pharmacodynamic measurement of the pharmacological effect of hydrocodone. These examples illustrate that hydrocodone conjugates decrease the analgesic effect by the intranasal route of administration as compared to hydrodone bitartrate.

Example 47

Decreased Intravenous Analgesic Response to Hydrocodone Conjugates

Male Sprague-Dawley rats were dosed by tail vein injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 16 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the intravenous route of administration as compared to hydrocodone bitartrate.

Example 48

Decreased Subcutaneous Analgesic Response to Hydrocodone Conjugates

Male Sprague-Dawley rats were dosed by subcutatenous injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 11 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the subcutaneous route of administration as compared to hydrocodone bitartrate.

Example 49

Decreased Oral $C_{max}$ of Hydrocodone Conjugates

Male Sprague-Dawley rats were provided water ad libitum, fasted overnight and dosed by oral gavage with hydrocodone conjugates or hydrocodone bitartrate. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitratrate are shown in FIGS. 2, 25, 33 and 34. These examples illustrate that hydrocodone conjugates decrease the peak level ($C_{max}$) of hydrocodone plus hydromorphone as compared to that produced by equimolar (hydrocodone base) doses of hydrocodone bitartrate when given by the oral route of administration.

Example 50

Decreased Intranasal Bioavailability (AUC and $C_{max}$) Hydrocodone Conjugates

Male Sprague-Dawley rats were provided water ad libitum and doses were administered by placing 0.02 ml of water containing hydrocodone conjugates or hydrocodone bitartrate into the nasal flares. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitartrate are shown in FIGS. 4, 5, 13-15, 18-22, 24, and 26-34. These examples illustrate that hydrocodone conjugates decrease the peak level ($C_{max}$) and total absorption (AUC) of hydrocodone plus hydromorphone as compared to those produced by equimolar (hydrocodone base) doses of hydrocodone bitartrate when given by the intranasal route of administration.

Example 51

Figure 17:
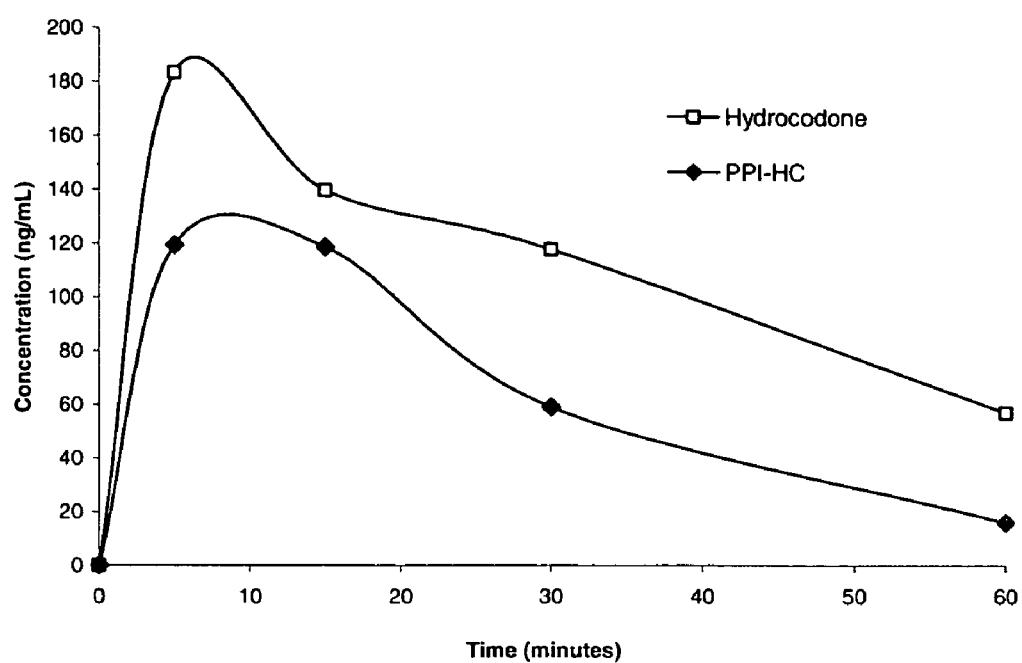
FIG. 17. Intranasal bioavailability of an abuse-resistant hydrocodone tri-peptide conjugate, measured as free hydrocodone.
Figure 18:
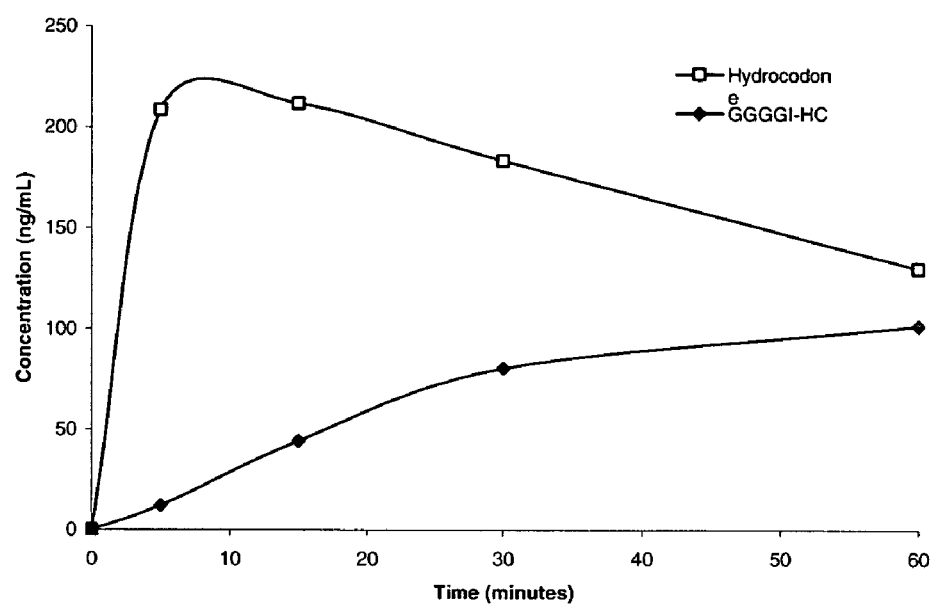
FIG. 18. Intranasal bioavailability of an abuse-resistant hydrocodone penta-peptide conjugate, measured as free hydrocodone.
Figure 19:
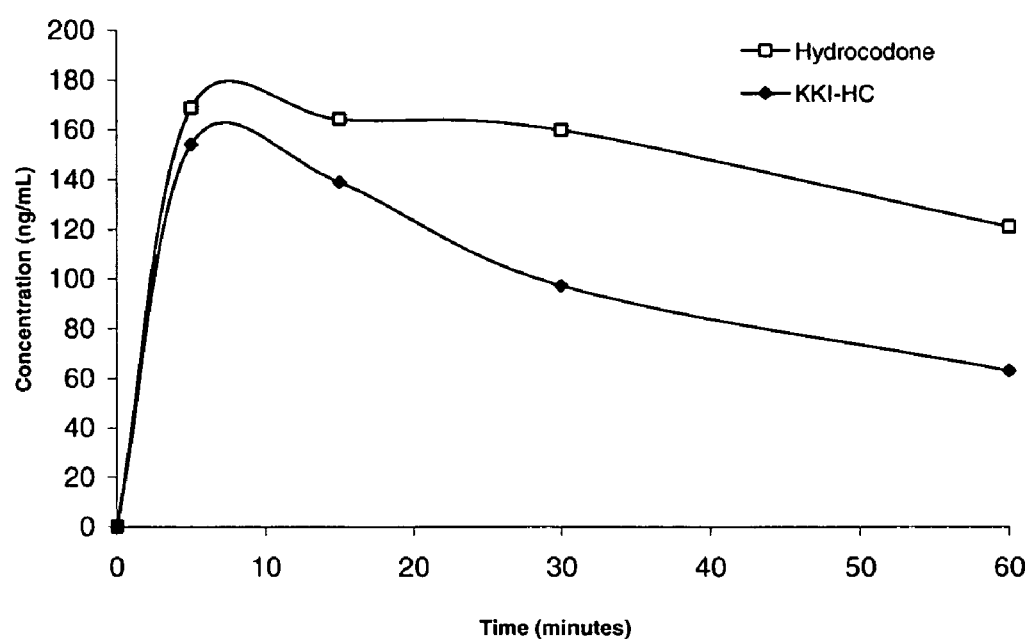
FIG. 19. Intranasal bioavailability of an abuse-resistant hydrocodone tri-peptide conjugate, measured as free hydrocodone.
Figure 20:
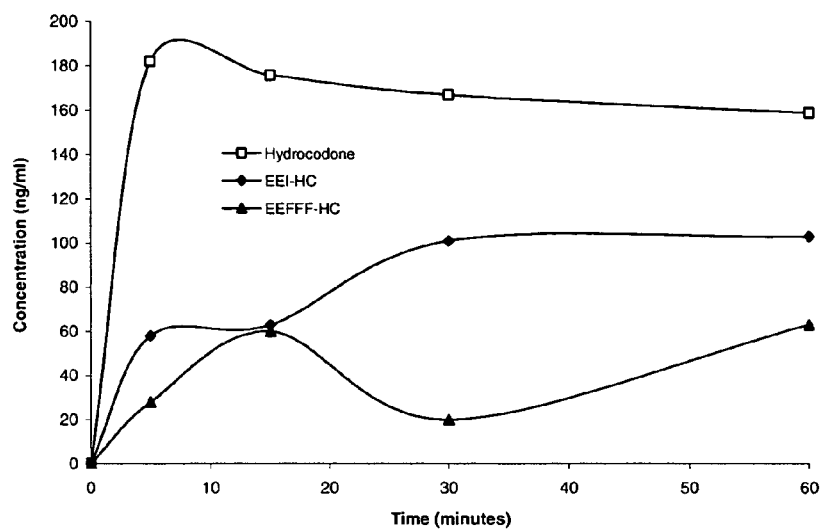
FIG. 20. Intranasal bioavailability of abuse-resistant hydrocodone tri- and penta-peptide conjugates, measured as free hydrocodone.
Figure 21:
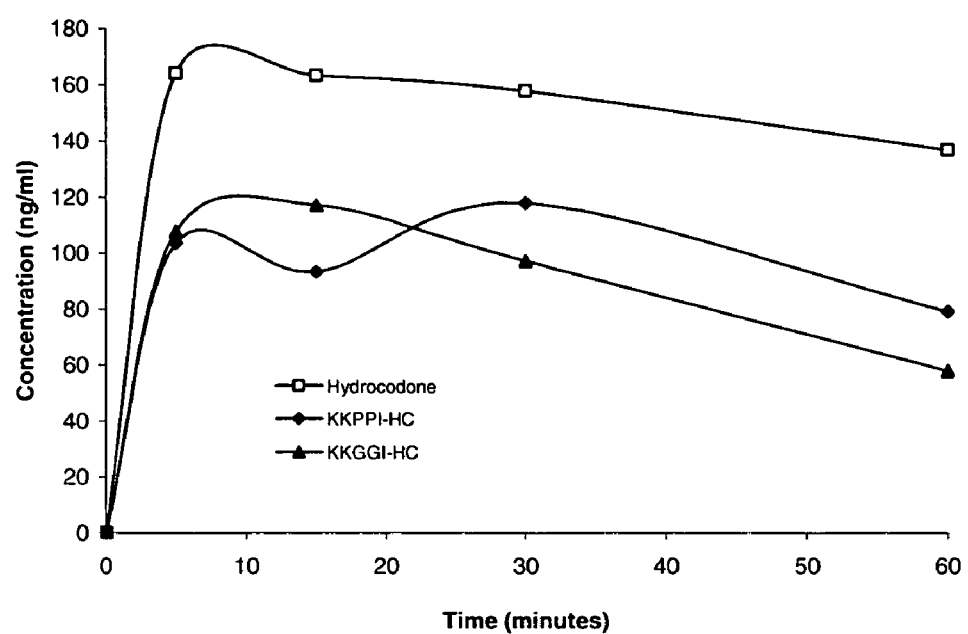
FIG. 21. Intranasal bioavailability of abuse-resistant hydrocodone penta-peptide conjugates, measured as free hydrocodone.
Figure 22:
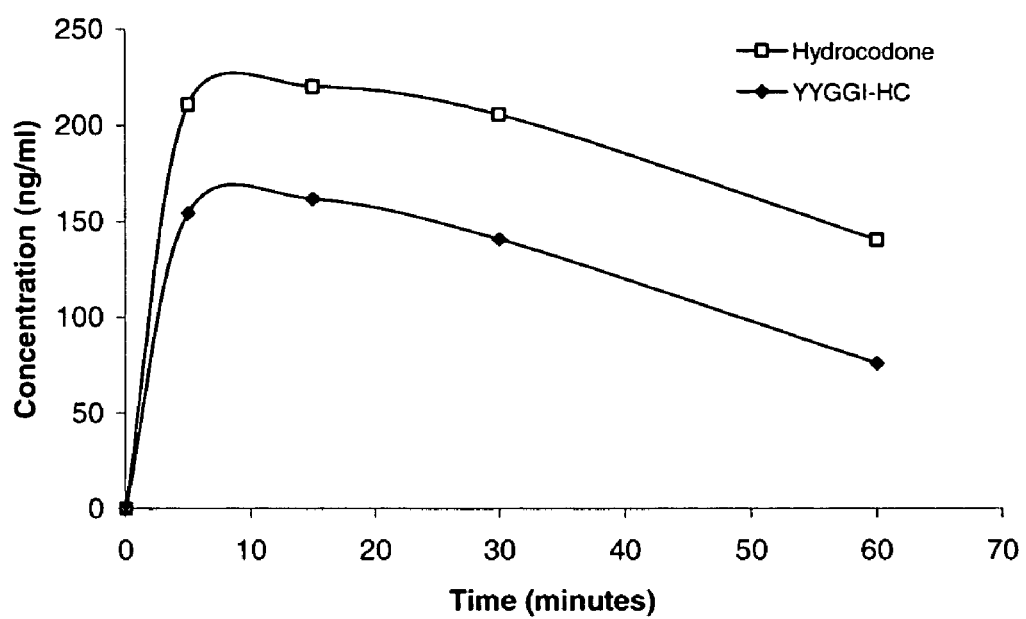
FIG. 22. Intranasal bioavailability of an abuse-resistant hydrocodone penta-peptide conjugate, measured as free hydrocodone.
Figure 23:
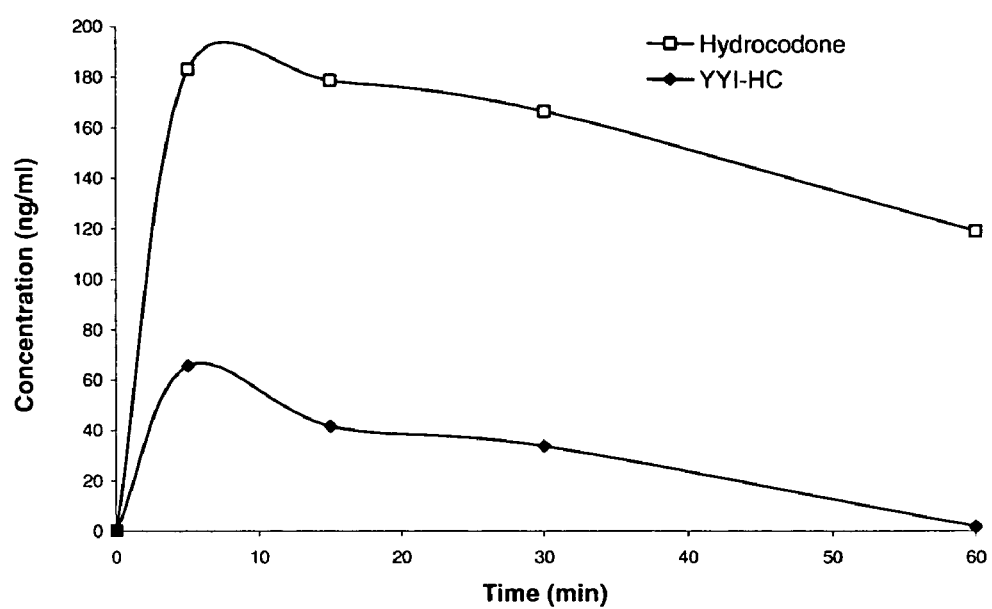
FIG. 23. Intravenous bioavailability of an abuse-resistant hydrocodone tri-peptide conjugate, measured as free hydrocodone.
Figure 24:
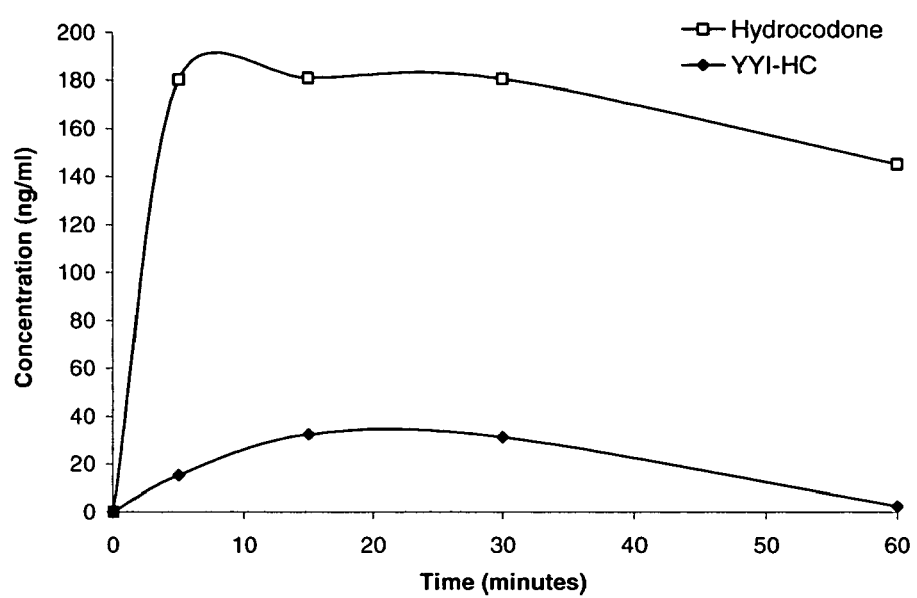
FIG. 24. Intranasal bioavailability of an abuse-resistant hydrocodone tri-peptide conjugate, measured as free hydrocodone.
Figure 25:
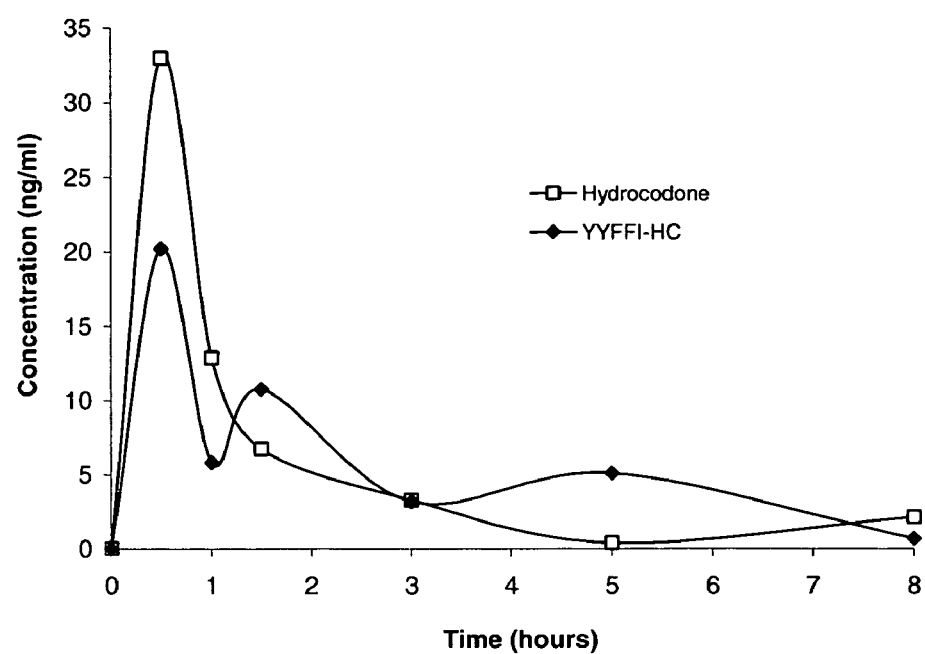
FIG. 25. Oral bioavailability of an abuse-resistant hydrocodone penta-peptide conjugate, measured as free hydrocodone.
Figure 26:
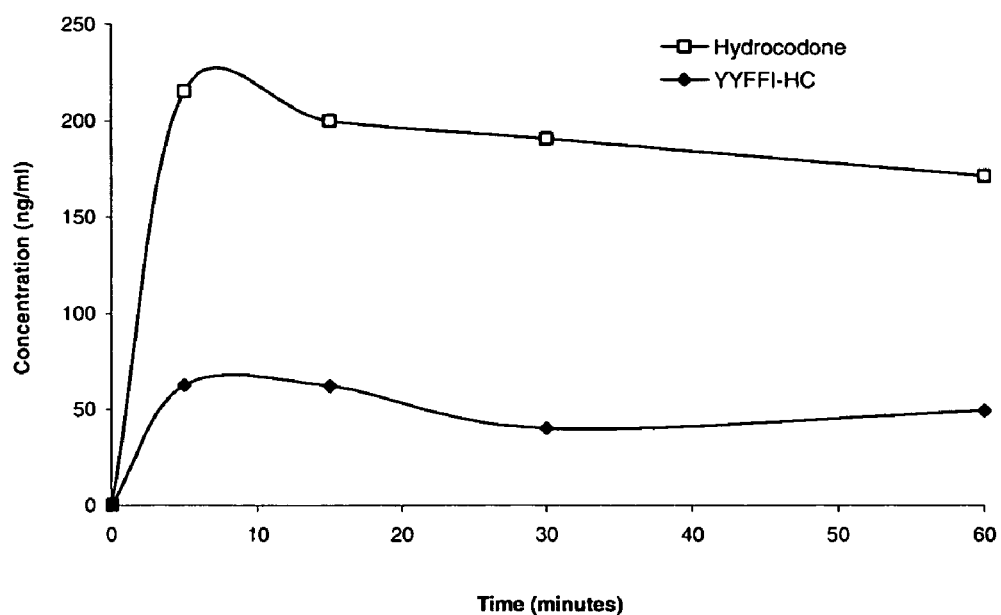
FIG. 26. Intranasal bioavailability of an abuse-resistant hydrocodone tri-penta-peptide conjugate, measured as free hydrocodone.
Figure 27:
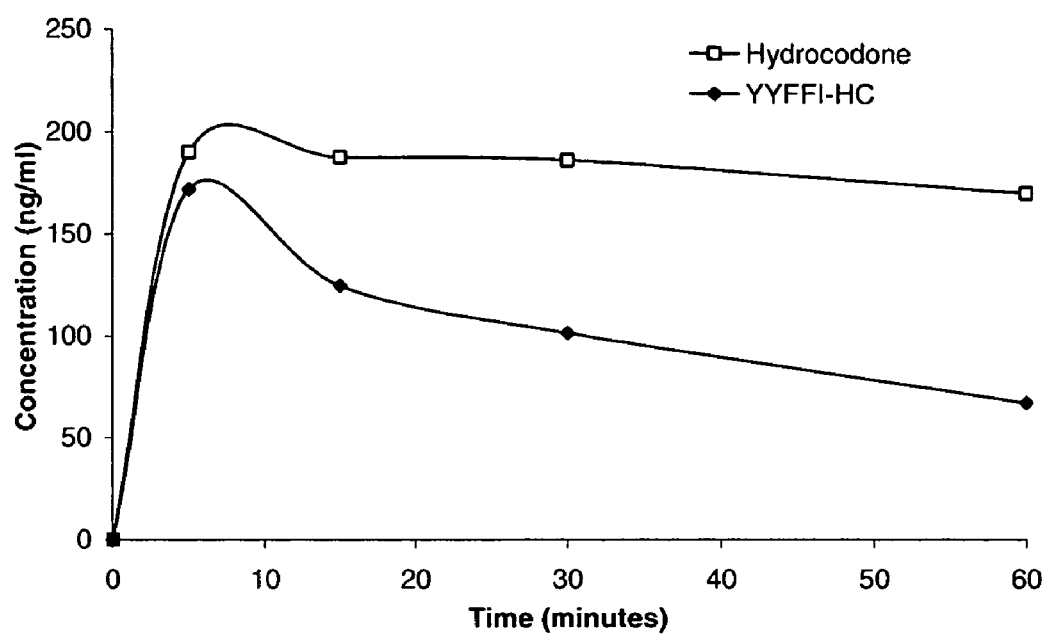
FIG. 27. Intranasal bioavailability of an abuse-resistant hydrocodone penta-peptide conjugate, measured as free hydrocodone.
Figure 28:
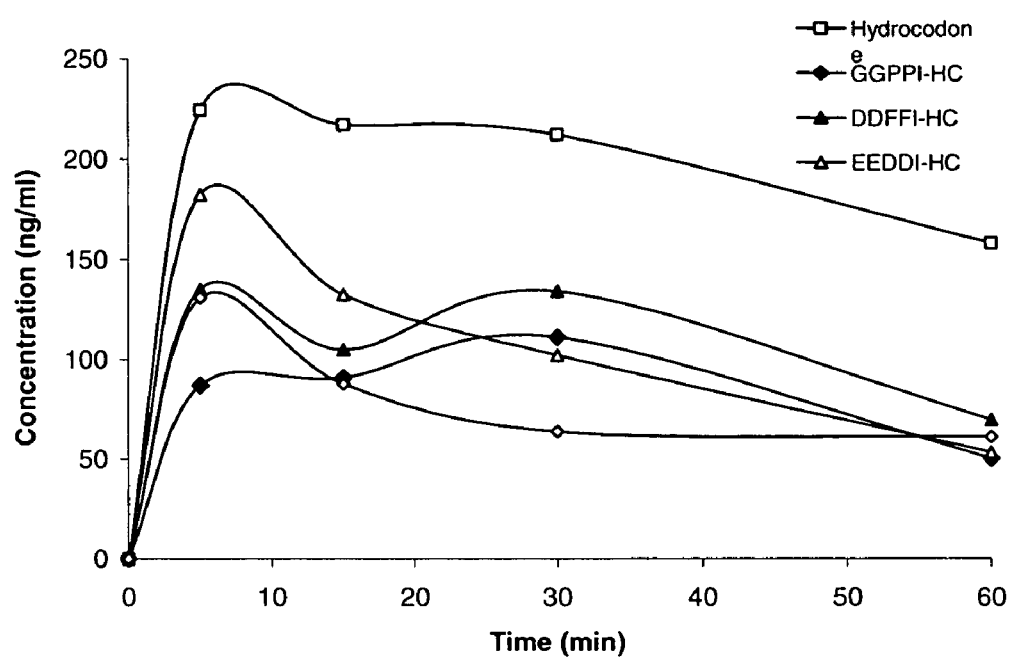
FIG. 28. Intranasal bioavailability of abuse-resistant hydrocodone penta-peptide conjugates, measured as free hydrocodone.
Figure 29:
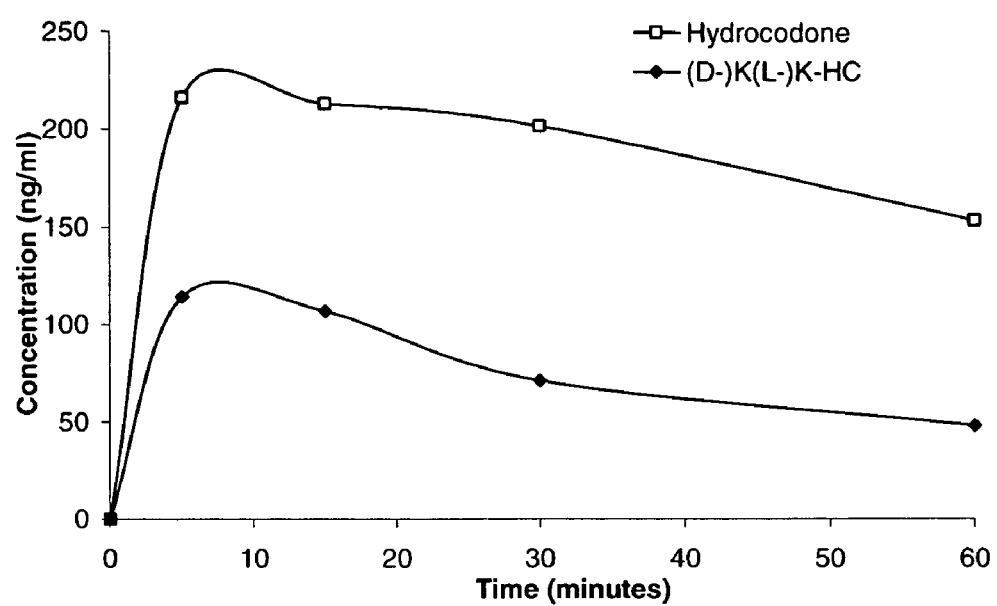
FIG. 29. Intranasal bioavailability of an abuse-resistant hydrocodone tri-peptide conjugate containing D-and L-isomers, measured as free hydrocodone.
Figure 30:
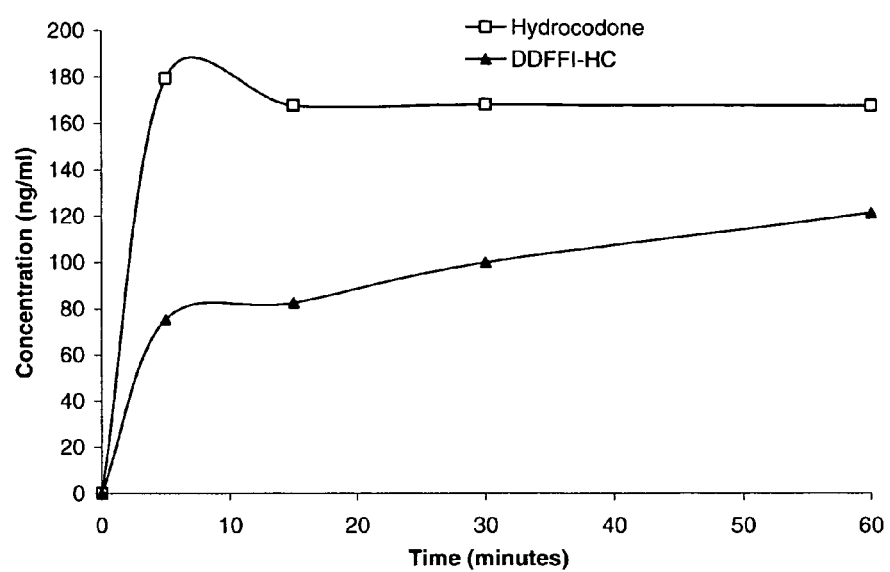
FIG. 30. Intranasal bioavailability of an abuse-resistant hydrocodone penta-peptide conjugate, measured as free hydrocodone.
Figure 31:
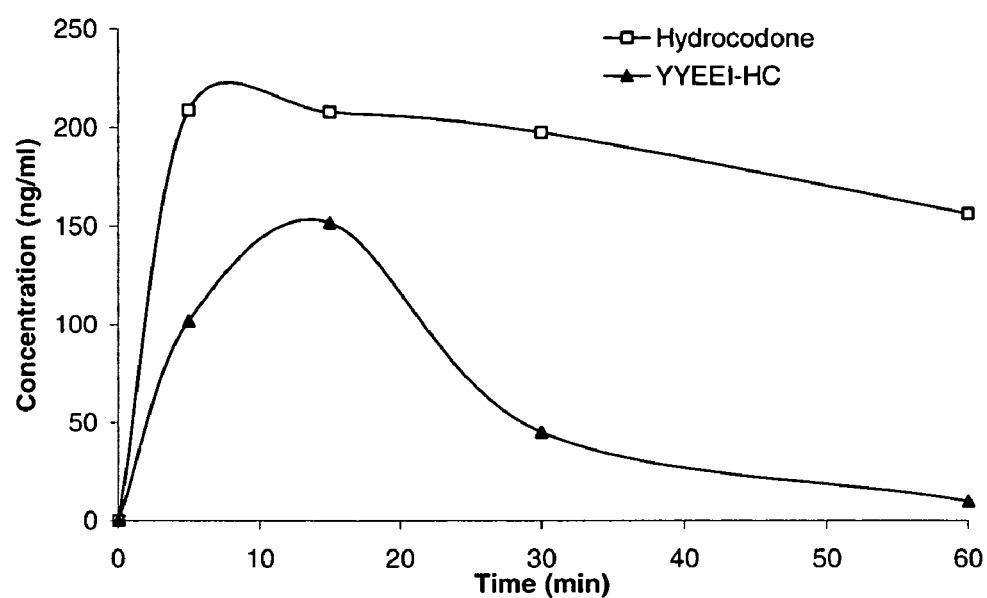
FIG. 31. Intranasal bioavailability of an abuse-resistant hydrocodone penta-peptide conjugate, measured as free hydrocodone.
Figure 32:
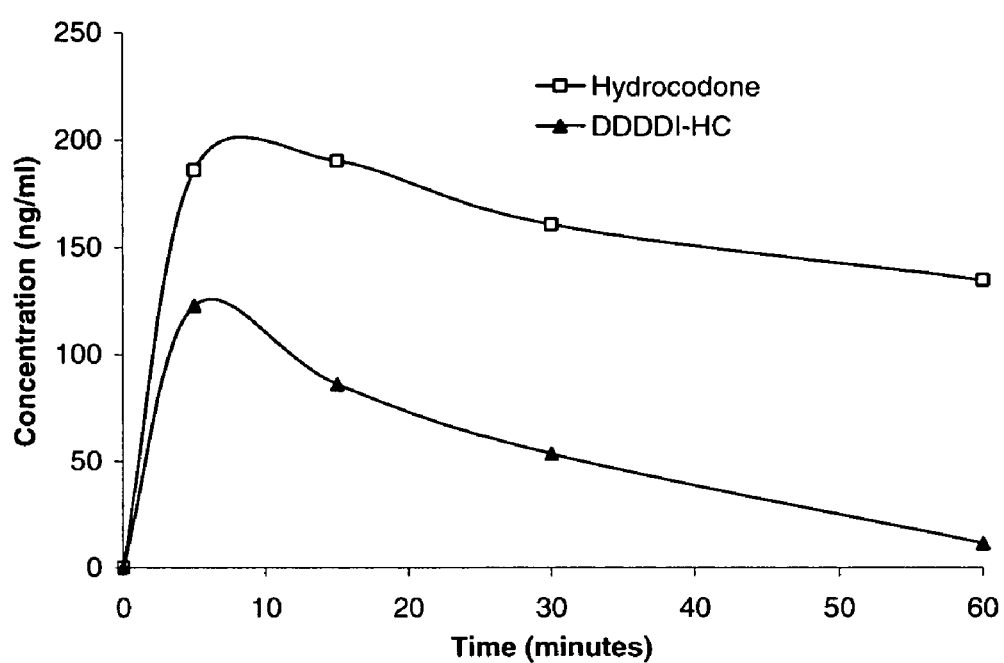
FIG. 32. Intranasal bioavailability of an abuse-resistant hydrocodone penta-peptide conjugate, measured as free hydrocodone.
Figure 33:
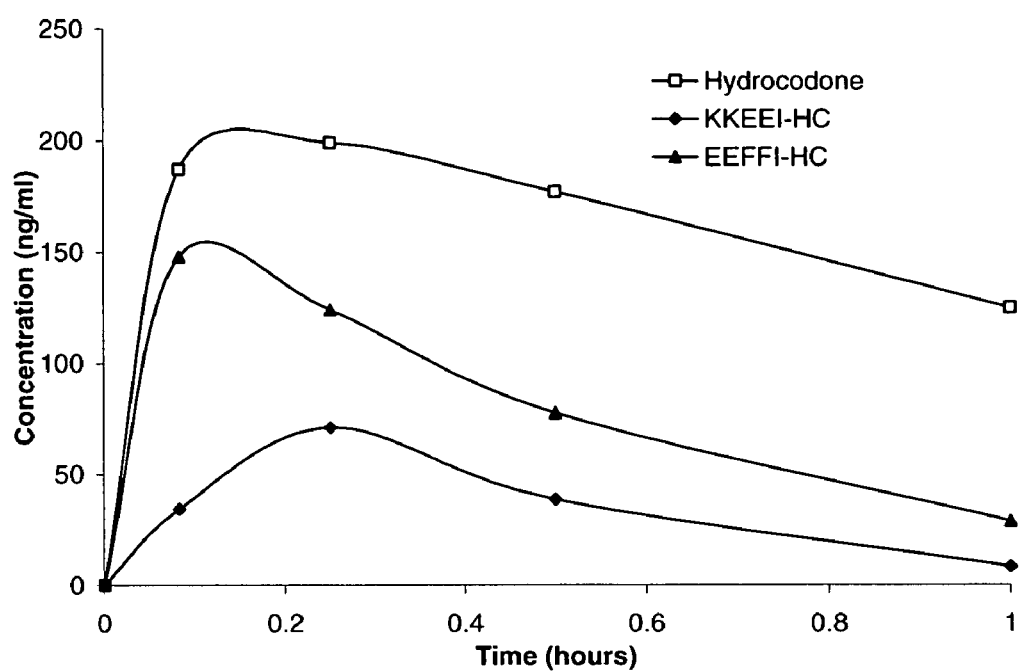
FIG. 33. Intranasal bioavailability of abuse-resistant hydrocodone penta-peptide conjugates, measured as free hydrocodone.
Figure 34:
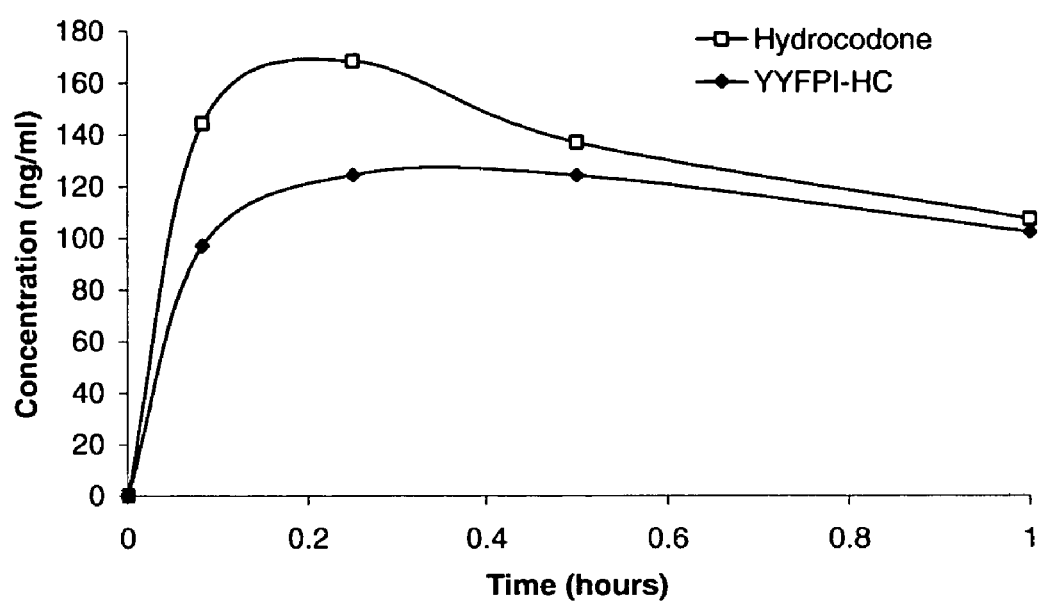
FIG. 34. Intranasal bioavailability of an abuse-resistant hydrocodone penta-peptide conjugate, measured as free hydrocodone.

Decreased Intravenous Bioavailability (AUC and $C_{max}$) Hydrocodone Conjugates Male Sprague-Dawley rats were provided water ad libitum and doses were administered by intravenous tail vein injection of 0.1 ml of water containing hydrocodone conjugates or hydrocodone bitartrate. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of a hydrocodone conjugate vs. hydrocodone bitartrate is shown in FIG. 17. This example illustrates that a dose of hydrocodone conjugate decreases the peak level ($C_{max}$) and total absorption (AUC) of hydrocodone plus hydromorphone as compared to those produced by an equimolar (hydrocodone base) dose of hydrocodone bitartrate when given by the intranasal route of administration.

The invention claimed is:

1. A composition comprising hydrocodone covalently bound at the 6' position to a single amino acid or an oligopeptide of 15 or fewer amino acids through the N-terminus or side chain of said oligopeptide or said amino acid, or a pharmaceutically acceptable salt thereof, and a pharmaceutically acceptable additive in a form suitable for oral administration.

2. The composition of claim 1, wherein said oligopeptide comprises fewer than 10 amino acids.

3. The composition of claim 1, wherein said oligopeptide comprises fewer than 6 amino acids.

4. The composition of claim 1, wherein the oligopeptide is selected from a dipeptide, a tripeptide, a tetrapeptide, a pentapeptide, and a hexapeptide.

5. The composition of claim 1, wherein the oligopeptide is a pentapeptide.

6. The composition of claim 5, wherein said pentapeptide consists essentially of naturally occurring amino acids.

7. The composition of claim 1 wherein said hydrocodone is resistant to release from said amino acid or said oligopeptide when the composition is manipulated for parenteral administration.

8. The composition of claim 1, wherein said form suitable for oral administration is a tablet, a capsule, a caplet, an oral solution, or an oral suspension.

9. The composition of claim 6, wherein said form suitable for oral administration is a tablet, a capsule, a caplet, an oral solution, or an oral suspension.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: artificial sequence
<220> FEATURE:
<223> OTHER INFORMATION: synthetic carrier

<400> SEQUENCE: 1

Gly Gly Gly Gly Leu
1               5

<210> SEQ ID NO 2
<211> LENGTH: 6
<212> TYPE: PRT
<213> ORGANISM: artificial sequence
<220> FEATURE:
<223> OTHER INFORMATION: synthetic carrier

<400> SEQUENCE: 2

Glu Glu Phe Phe Phe Ile
1               5

<210> SEQ ID NO 3
<211> LENGTH: 5
<212> TYPE: PRT
<213> ORGANISM: artificial sequence
<220> FEATURE:
<223> OTHER INFORMATION: synthetic carrier

<400> SEQUENCE: 3

Glu Glu Phe Phe Phe
```

```
1               5

<210> SEQ ID NO 4
<211> LENGTH: 5
<212> TYPE: PRT
<213> ORGANISM: artificial sequence
<220> FEATURE:
<223> OTHER INFORMATION: synthetic carrier

<400> SEQUENCE: 4

Tyr Tyr Phe Phe Ile
1               5

<210> SEQ ID NO 5
<211> LENGTH: 5
<212> TYPE: PRT
<213> ORGANISM: artificial sequence
<220> FEATURE:
<223> OTHER INFORMATION: synthetic carrier

<400> SEQUENCE: 5

Glu Glu Phe Phe Ile
1               5

<210> SEQ ID NO 6
<211> LENGTH: 5
<212> TYPE: PRT
<213> ORGANISM: artificial sequence
<220> FEATURE:
<223> OTHER INFORMATION: synthetic carrier

<400> SEQUENCE: 6

Lys Lys Pro Pro Ile
1               5

<210> SEQ ID NO 7
<211> LENGTH: 5
<212> TYPE: PRT
<213> ORGANISM: artificial sequence
<220> FEATURE:
<223> OTHER INFORMATION: synthetic carrier

<400> SEQUENCE: 7

Tyr Tyr Phe Pro Ile
1               5

<210> SEQ ID NO 8
<211> LENGTH: 5
<212> TYPE: PRT
<213> ORGANISM: artificial sequence
<220> FEATURE:
<223> OTHER INFORMATION: synthetic carrier

<400> SEQUENCE: 8

Gly Gly Gly Gly Leu
1               5

<210> SEQ ID NO 9
<211> LENGTH: 5
<212> TYPE: PRT
<213> ORGANISM: artificial sequence
<220> FEATURE:
<223> OTHER INFORMATION: synthetic carrier

<400> SEQUENCE: 9

Glu Glu Glu Glu Glu
1               5
```

```
<210> SEQ ID NO 10
<211> LENGTH: 5
<212> TYPE: PRT
<213> ORGANISM: artificial sequence
<220> FEATURE:
<223> OTHER INFORMATION: synthetic carrier

<400> SEQUENCE: 10

Glu Glu Gly Gly Ile
1               5

<210> SEQ ID NO 11
<211> LENGTH: 5
<212> TYPE: PRT
<213> ORGANISM: artificial sequence
<220> FEATURE:
<223> OTHER INFORMATION: synthetic carrir

<400> SEQUENCE: 11

Glu Glu Gly Gly Leu
1               5

<210> SEQ ID NO 12
<211> LENGTH: 5
<212> TYPE: PRT
<213> ORGANISM: artificial sequence
<220> FEATURE:
<223> OTHER INFORMATION: synthetic carrier

<400> SEQUENCE: 12

Gly Gly Gly Gly Ile
1               5

<210> SEQ ID NO 13
<211> LENGTH: 5
<212> TYPE: PRT
<213> ORGANISM: artificial sequence
<220> FEATURE:
<223> OTHER INFORMATION: synthetic carrier

<400> SEQUENCE: 13

Lys Lys Gly Gly Ile
1               5

<210> SEQ ID NO 14
<211> LENGTH: 5
<212> TYPE: PRT
<213> ORGANISM: artificial sequence
<220> FEATURE:
<223> OTHER INFORMATION: synthetic carrier

<400> SEQUENCE: 14

Tyr Tyr Gly Gly Ile
1               5

<210> SEQ ID NO 15
<211> LENGTH: 5
<212> TYPE: PRT
<213> ORGANISM: artificial sequence
<220> FEATURE:
<223> OTHER INFORMATION: synthetic carrier

<400> SEQUENCE: 15

Gly Gly Pro Pro Ile
1               5
```

```
<210> SEQ ID NO 16
<211> LENGTH: 5
<212> TYPE: PRT
<213> ORGANISM: artificial sequence
<220> FEATURE:
<223> OTHER INFORMATION: synthetic carrier

<400> SEQUENCE: 16

Asp Asp Phe Phe Ile
1               5

<210> SEQ ID NO 17
<211> LENGTH: 5
<212> TYPE: PRT
<213> ORGANISM: artificial sequence
<220> FEATURE:
<223> OTHER INFORMATION: synthetic carrier

<400> SEQUENCE: 17

Glu Glu Asp Asp Ile
1               5

<210> SEQ ID NO 18
<211> LENGTH: 5
<212> TYPE: PRT
<213> ORGANISM: artificial sequence
<220> FEATURE:
<223> OTHER INFORMATION: synthetic carrier

<400> SEQUENCE: 18

Lys Lys Asp Asp Ile
1               5

<210> SEQ ID NO 19
<211> LENGTH: 5
<212> TYPE: PRT
<213> ORGANISM: artificial sequence
<220> FEATURE:
<223> OTHER INFORMATION: synthetic carrier

<400> SEQUENCE: 19

Tyr Tyr Glu Glu Ile
1               5

<210> SEQ ID NO 20
<211> LENGTH: 5
<212> TYPE: PRT
<213> ORGANISM: artificial sequence
<220> FEATURE:
<223> OTHER INFORMATION: synthetic carrier

<400> SEQUENCE: 20

Asp Asp Asp Asp Ile
1               5

<210> SEQ ID NO 21
<211> LENGTH: 5
<212> TYPE: PRT
<213> ORGANISM: artificial sequence
<220> FEATURE:
<223> OTHER INFORMATION: synthetic carrier

<400> SEQUENCE: 21

Lys Lys Glu Glu Ile
1               5
```